United States Patent
Freeman et al.

(10) Patent No.: US 10,583,205 B2
(45) Date of Patent: Mar. 10, 2020

(54) HYPERPOLARIZED NOBLE GAS PRODUCTION SYSTEMS WITH NANOCLUSTER SUPPRESSION, DETECTION AND/OR FILTERING AND RELATED METHODS AND DEVICES

(71) Applicant: Duke University, Durham, NC (US)

(72) Inventors: Matthew S. Freeman, Cincinnati, OH (US); Bastiaan Driehuys, Chapel Hill, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 16/653,082

(22) Filed: Oct. 15, 2019

(65) Prior Publication Data

US 2020/0046858 A1 Feb. 13, 2020

Related U.S. Application Data

(60) Continuation of application No. 16/113,607, filed on Aug. 27, 2018, which is a division of application No. 15/120,013, filed as application No. PCT/US2015/016827 on Feb. 20, 2015, now Pat. No. 10,086,092.

(60) Provisional application No. 61/942,836, filed on Feb. 21, 2014.

(51) Int. Cl.
*A61K 49/06* (2006.01)
*A61K 49/18* (2006.01)
*C01B 23/00* (2006.01)
*G01R 33/28* (2006.01)

(52) U.S. Cl.
CPC ............ *A61K 49/06* (2013.01); *A61K 49/18* (2013.01); *C01B 23/00* (2013.01); *C01B 23/0036* (2013.01); *G01R 33/282* (2013.01)

(58) Field of Classification Search
CPC ........ A61K 49/06; A61K 49/18; C01B 23/00; C01B 23/0036; G01R 33/282
See application file for complete search history.

(56) References Cited

U.S. PATENT DOCUMENTS

| 5,545,396 A | 8/1996 | Albert et al. |
| 5,612,103 A | 3/1997 | Driehuys et al. |
| 5,642,625 A | 7/1997 | Cates, Jr. et al. |
| 5,809,801 A | 9/1998 | Cates, Jr. et al. |
| 5,860,295 A | 1/1999 | Cates, Jr. et al. |
| 6,079,213 A | 6/2000 | Driehuys et al. |

(Continued)

FOREIGN PATENT DOCUMENTS

| CN | 200965510 | 10/2007 |
| EP | 1588178 | 10/2011 |

(Continued)

OTHER PUBLICATIONS

"3mm High Quality Silica Wick 30' Feet Length" Amazon.com Product overview (2 pages) (accessed Feb. 19, 2015).

(Continued)

*Primary Examiner* — Daniel C. McCracken
(74) *Attorney, Agent, or Firm* — Myers Bigel, P.A.

(57) ABSTRACT

Systems, methods and related devices used to produce and collect polarized noble gas to inhibit, suppress, detect or filter alkali metal nanoclusters to preserve or increase a polarization level thereof. The systems can include a pre-sat chamber that has an Area Ratio between 20 and 500.

30 Claims, 23 Drawing Sheets

(56) References Cited

U.S. PATENT DOCUMENTS

| | | | |
|---|---|---|---|
| 6,295,834 | B1 | 10/2001 | Driehuys |
| 6,318,092 | B1 | 11/2001 | Harper et al. |
| 6,949,169 | B2 | 9/2005 | Hersman et al. |
| 7,281,393 | B2 | 10/2007 | Hersman |
| 7,719,268 | B2 | 5/2010 | Hersman et al. |
| 7,769,068 | B2 | 8/2010 | Hersman et al. |
| 7,928,359 | B2 | 4/2011 | Hersman |
| 2004/0223522 | A1 | 11/2004 | Hersman |
| 2006/0269614 | A1* | 11/2006 | Nelson ............... A61K 33/00 424/600 |
| 2007/0120563 | A1 | 5/2007 | Kawabata et al. |
| 2011/0128002 | A1 | 6/2011 | Fujiwara et al. |

FOREIGN PATENT DOCUMENTS

| | | |
|---|---|---|
| WO | 199640585 | 12/1996 |
| WO | 2013068448 | 5/2013 |

OTHER PUBLICATIONS

Atutov et al. "Explosive evaporation of Rb or K fractal clusters by low power CW radiation in the presence of excited atoms". The European Physical Journal D 66(140):1-6 (2012)

Bhaskar et al. "Efficiency of Spin Exchange between Rubidium Spins and 129Xe Nuclei in a Gas" Physical Review Letters 49(1):25-28 (1982).

Couture et al. "Pressure shifts and broadening of the Cs D1 and D2 lines by He, N2, and Xe at densities used for optical pumping and spin exchange polarization" Journal of Applied Physics 104:094912-1-094912-6 (2008).

Driehuys et al. "High volume production of laser-polarized 129Xe" Applied Physics Letters 69(12):1668-1670 (1996).

Driehuys et al. "In Vivo MRI Using Real-Time Production of Hyperpolarized 129Xe" Magnetic Resonance in Medicine 60(1):14-20 (2008).

Extended European Search Report corresponding to European Patent Application No. 15751691.5 (8 pages) (dated Jul. 7, 2017).

Freeman et al. "Characterizing and modeling the efficiency limits in large-scale production of hyperpolarized 129Xe" Physical Review A 90:023406-1-023406-14 (2014).

Goodson, Boyd M. "Nuclear Magnetic Resonance of Laser-Polarized Noble Gases in Molecules, Materials, and Organisms" Journal of Magnetic Resonance 155:157-216 (2002).

Hersman et al. "Large Production System for Hyperpolarized 129Xe for Human Lung Imaging Studies" Academic Radiology 15(6):683-692 (2008).

Imai et al. "Effect of Reduced Pressure on the Polarization of 129Xe in the Production of Hyperpolarized 129Xe Gas: Development of a Simple Continuous Flow Mode Hyperpolarizing System Working at Pressures as Low as 0.15 atm" Concepts in Magnetic Resonance Part B (Magnetic Resonance Engineering) 33B(3):192-200 (2008).

International Preliminary Report on Patentability corresponding to International Patent Application No. PCT/US2015/016827 (dated Aug. 23, 2016) (10 pages).

International Search Report and the Written Opinion of the International Searching Authority corresponding to International Patent Application No. PCT/US2015/016827 (14 pages) (dated Apr. 29, 2015).

Korchak et al. "Configuration and Performance of a Mobile 129Xe Polarizer" Applied Magnetic Resonance 44:65-80 (2013).

Lowery et al. "Applications of laser-polarized 129Xe to biomolecular assays" Magnetic Resonance Imaging 21:1235-1239 (2003).

Mortuza et al. "Spin-exchange optical pumping of high-density xenon-129" Journal of Chemical Physics 118(4):1581-1584 (2003).

Mugler et al. "Hyperpolarized 129Xe MRI of the Human Lung" Journal of Magnetic Resonance Imaging 37 (2):313-331 (2013).

Navon et al. "Enhancement of Solution NMR and MRI with Laser-Polarized Xenon" Science 271:1848-1851 (1996).

Nelson et al. "Rb-Xe spin relaxation in dilute Xe mixtures" Physical Review A 65:012712-1-012712-6 (2001).

Nikolaou et al. "Generation of laser-polarized xenon using fiber-coupled laser-diode arrays narrowed with integrated volume holographic gratings" Journal of Magnetic Resonance 197:249-254 (2009).

Norquay et al. "Optimized production of hyperpolarized 129Xe at 2 bars for in vivo lung magnetic resonance imaging" Journal of Applied Physics 113:044908-2-044908-9 (2013).

Office Action corresponding to related Chinese Patent Application No. 201580020817.8 (19 pages) (dated Oct. 31, 2018).

Romalis et al. "Transverse Spin Relaxation in Liquid 129Xe in the Presence of Large Dipolar Fields" Physical Review Letters 87(6):067601-1-067601-4 (2001).

Rosen et al. "Polarized 129Xe optical pumping/spin exchange and delivery system for magnetic resonance spectroscopy and imaging studies" Review of Scientific Instruments 70(2):1546-1552 (1999).

Ruset et al. "Optical Pumping System Design for Large Production of Hyperpolarized 129Xe" Physical Review Letters 96(5):053002-1-053002-4 (2006).

Schrank et al. "Characterization of a low-pressure high-capacity 129Xe flow-through polarizer" Physical Review A 80:063424-1-063424-10 (2009).

Schröder et al. "Molecular Imaging Using a Targeted Magnetic Resonance Hyperpolarized Biosensor" Science, New Series 314(5798):446-449 (2006).

Shukla et al. "Hyperpolarized 129Xe Magnetic Resonance Imaging: Tolerability in Healthy Volunteers and Subjects with Pulmonary Disease" Academic Radiology 19(8):941-951 (2012).

Spence et al. "Functionalized xenon as a biosensor" Proceedings of the National Academy of Sciences 98(19):10654-10657 (2001).

Springuel-Huet et al. "129Xe NMR overview of xenon physisorbed in porous solids" Magnetic Resonance in Chemistry 37:S1-S13 (1999).

Wagshul et al. "Optical pumping of high-density Rb with a broadband dye laser and GaAIAs diode laser arrays: Application to 3He polarization" Physical Review A 40(8):4447-4454 (1989).

Walker et al. "Spin-exchange optical pumping of noble-gas nuclei" Reviews of Modern Physics 69(2):629-642 (1997).

Walter et al. "Energy Transport in High-Density Spin-Exchange Optical Pumping Cells" Physical Review Letters 86(15):3264-3267 (2001).

Wolber et al. "Hyperpolarized 129Xe NMR as a Probe for Blood Oxygenation" Magnetic Resonance in Medicine 43:491-496 (2000).

Zook et al. "High capacity production of >65% spin polarized xenon-129 for NMR spectroscopy and imaging" Journal of Magnetic Resonance 159:175-182 (2002).

* cited by examiner

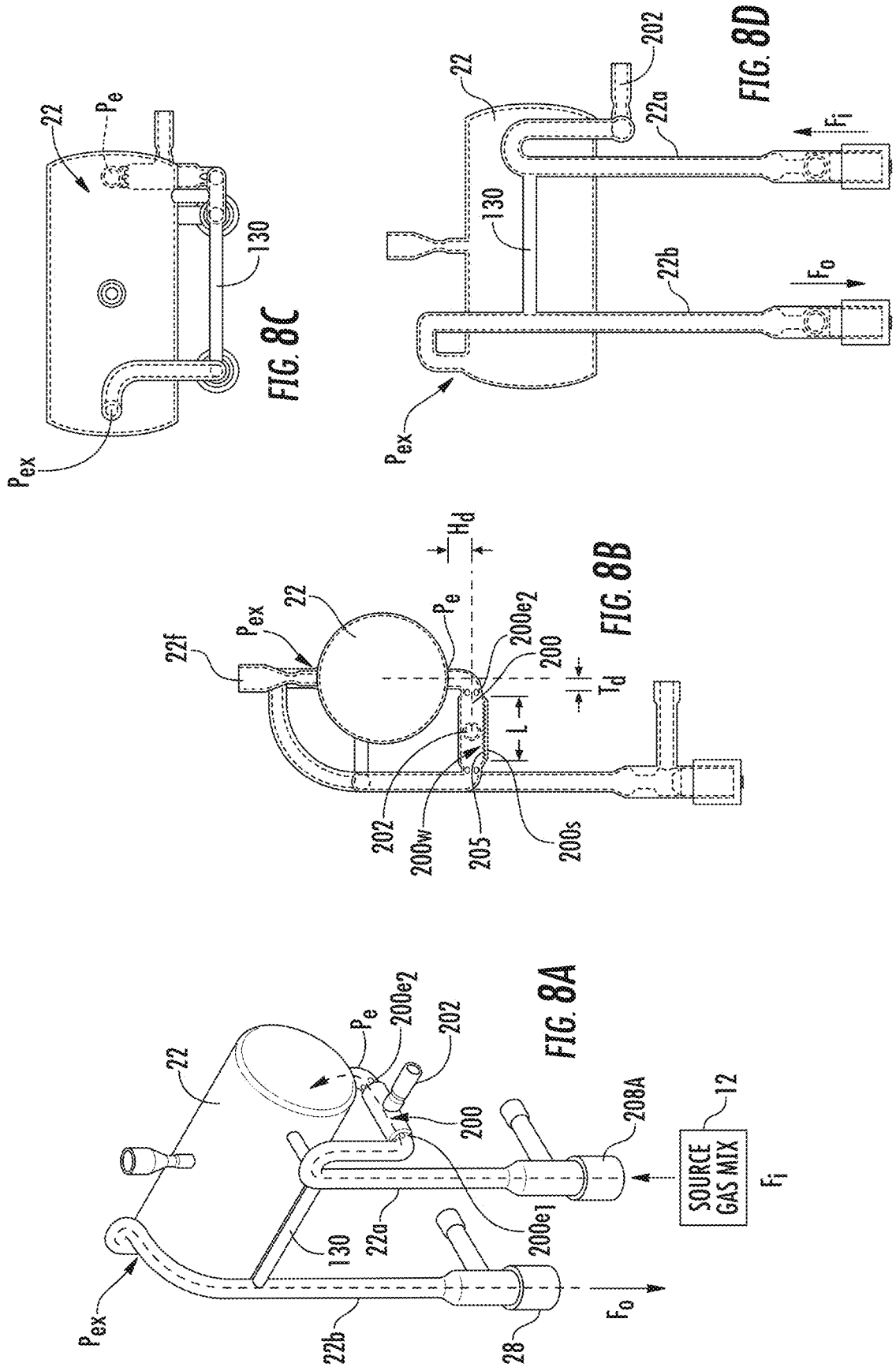

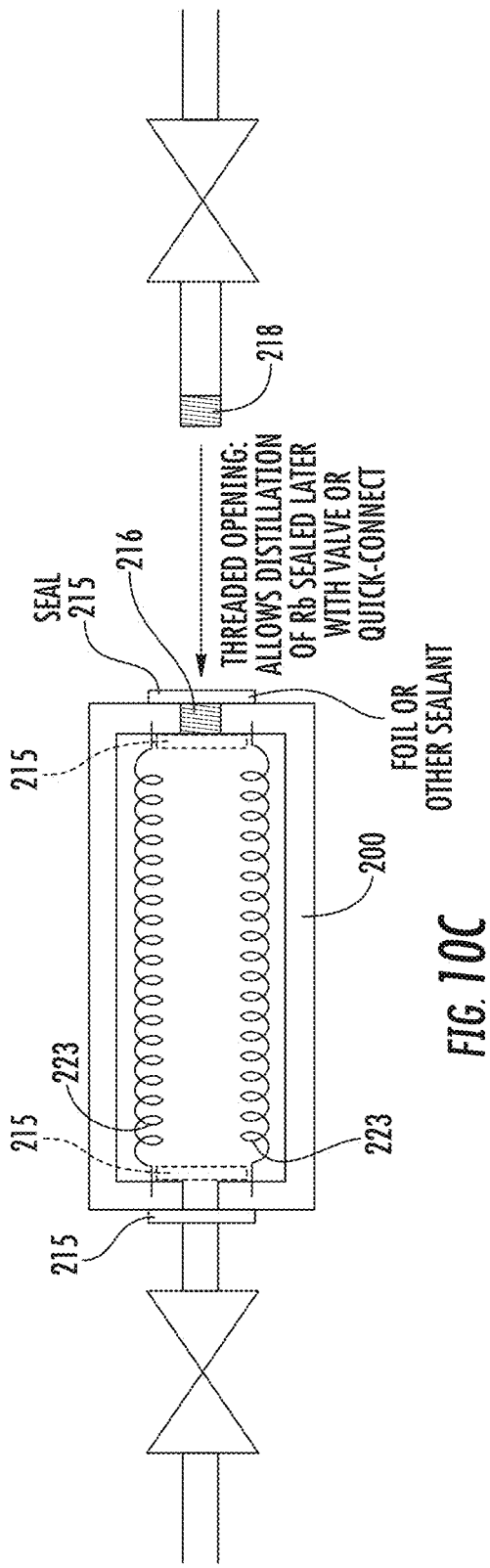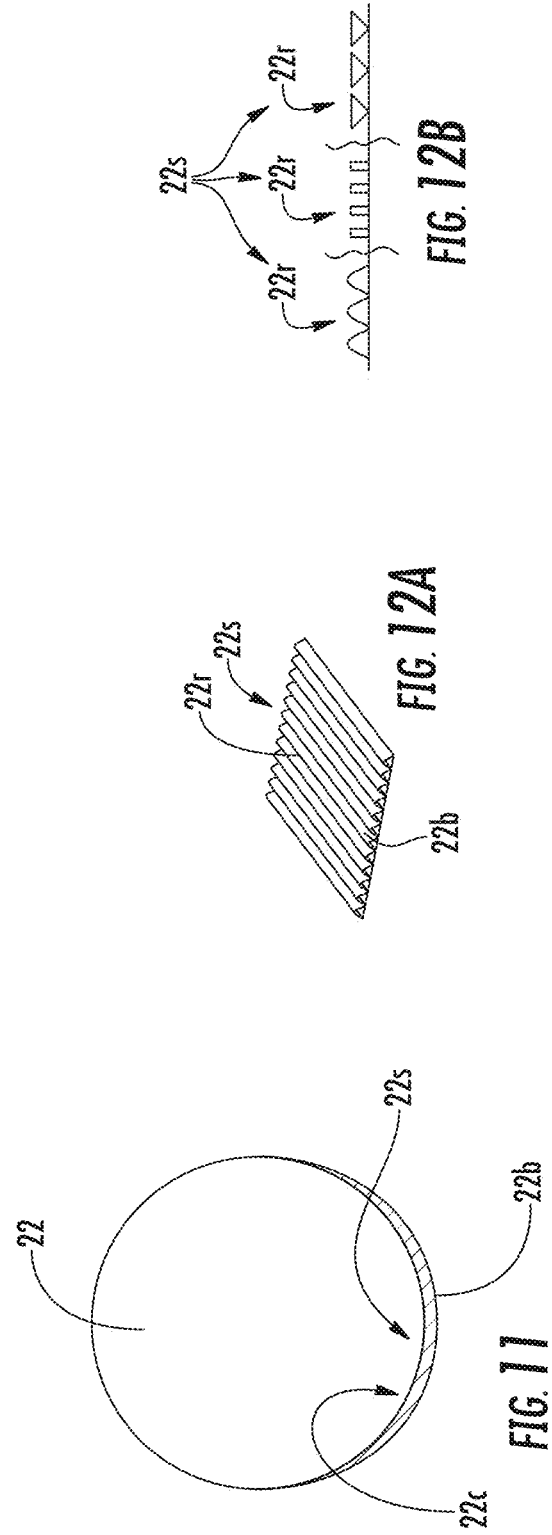

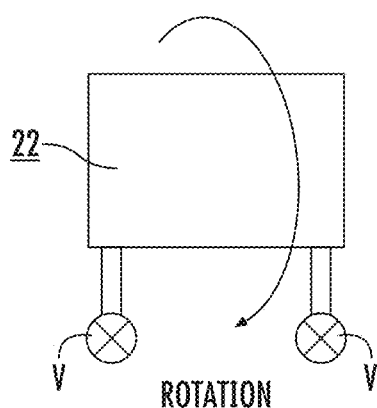
FIG. 15A
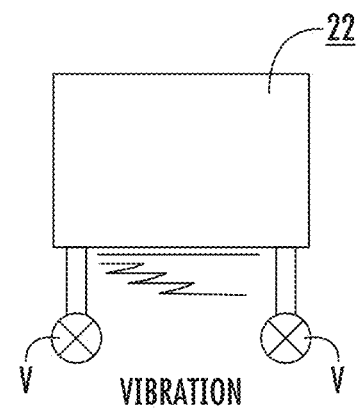
FIG. 15B
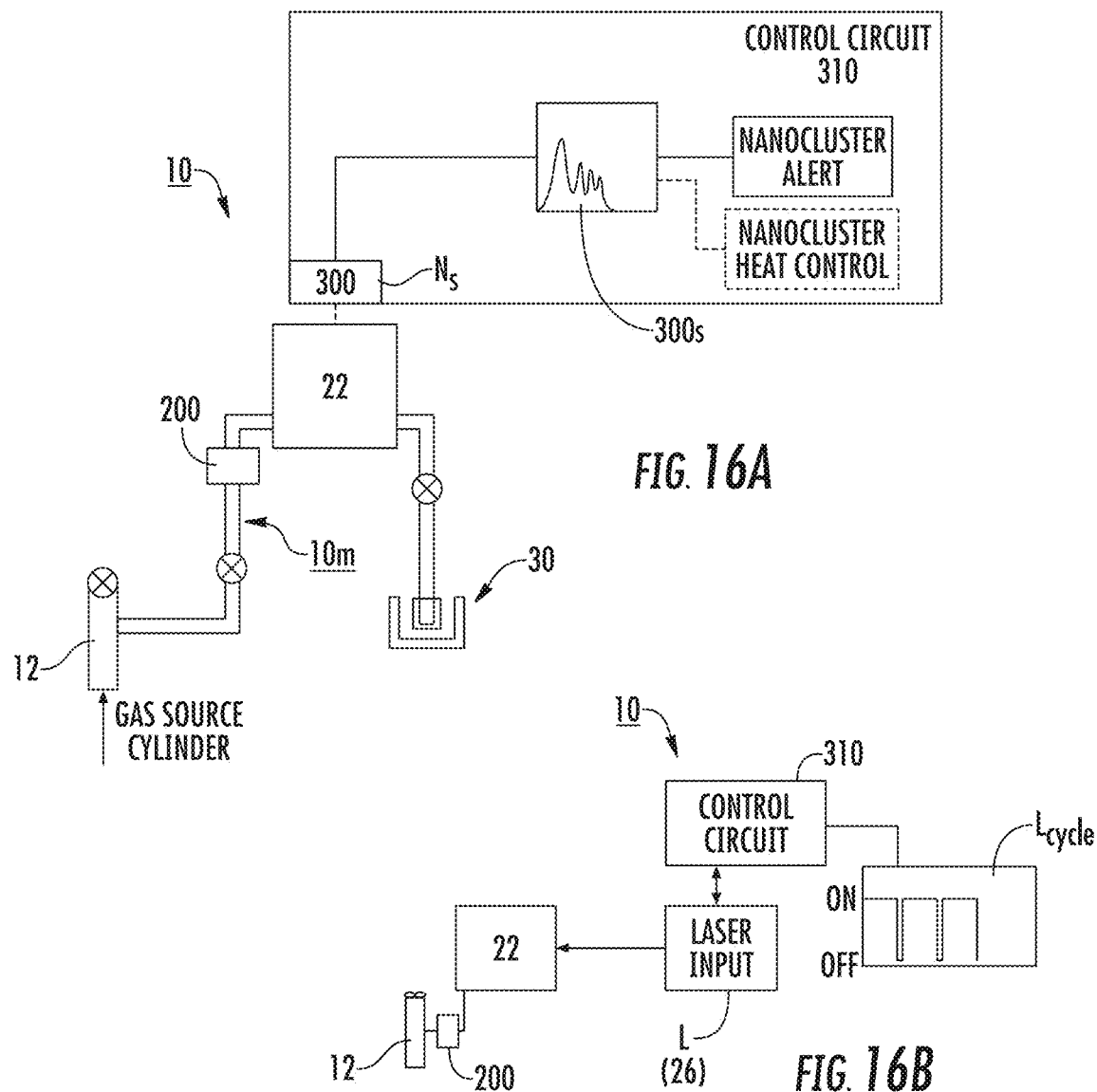
FIG. 16A
FIG. 16B

HYPERPOLARIZED NOBLE GAS PRODUCTION SYSTEMS WITH NANOCLUSTER SUPPRESSION, DETECTION AND/OR FILTERING AND RELATED METHODS AND DEVICES

RELATED APPLICATIONS

This application is a continuation application of U.S. application Ser. No. 16/113,607, filed Aug. 27, 2018, which is a divisional application of U.S. application Ser. No. 15/120,013, filed Aug. 18, 2016, now U.S. Pat. No. 10,086, 092, issued Oct. 2, 2018, which is a 35 USC § 371 national phase application of PCT/US2015/016827, International Filing Date Feb. 20, 2015, which claims the benefit of and priority to U.S. Provisional Application Ser. No. 61/942,836, filed Feb. 21, 2014, the contents of which are hereby incorporated by reference as if recited in full herein.

GOVERNMENT RIGHTS

This invention was made with Government support under NIBIB Grant number P41 EB015897 and NHLBI Grant number R01HL105643. The United States Government has certain rights in the invention.

FIELD OF THE INVENTION

The present invention relates to the production of hyperpolarized gases for use in magnetic resonance imaging ("MRI") applications.

BACKGROUND OF THE INVENTION

Conventionally, MRI has been used to produce images by exciting the nuclei of hydrogen atoms (present in water molecules) in the human body. MRI imaging with polarized noble gases can produce improved images of certain areas and regions of the body. Polarized Helium-3 ("$^3$He") and Xenon-129 ("$^{129}$Xe") have been found to be particularly suited for this purpose.

Hyperpolarizers are used to produce and accumulate polarized noble gases. Hyperpolarizes artificially enhance the polarization of certain noble gas nuclei (such as $^{129}$Xe or $^3$He) over the natural or equilibrium levels, i.e., the Boltzmann polarization. Such an increase is desirable because it enhances and increases the Magnetic Resonance Imaging ("MRI") signal intensity, allowing physicians to obtain better images of the substance in the body. See U.S. Pat. No. 5,642,625 to Cates et al. and U.S. Pat. No. 5,545,396 to Albert et al., the contents of which are hereby incorporated herein by reference as if recited in full herein.

In order to produce the hyperpolarized gas, the noble gas is typically blended with optically pumped alkali metal vapors such as rubidium ("Rb"). These optically pumped metal vapors collide with the nuclei of the noble gas and hyperpolarize the noble gas through a phenomenon known as "spin-exchange." The "optical pumping" of the alkali metal vapor is produced by irradiating the alkali-metal vapor with circularly polarized light at the wavelength of the first principal resonance for the alkali metal (e.g., 795 nm for Rb). Generally stated, the ground state atoms become excited, then subsequently decay back to the ground state. Under a modest magnetic field (10 Gauss), the cycling of atoms between the ground and excited states can yield nearly 100% polarization of the atoms in a few microseconds. This polarization is generally carried by the lone valence electron characteristics of the alkali metal. In the presence of non-zero nuclear spin noble gases, the alkali-metal vapor atoms can collide with the noble gas atoms in a manner in which the polarization of the valence electrons is transferred to the noble-gas nuclei through a mutual spin flip "spin-exchange."

Conventionally, lasers have been used to optically pump the alkali metals. Various lasers emit light signals over various wavelength bands. In order to improve the optical pumping process for certain types of lasers (particularly those with broader bandwidth emissions), the absorption or resonance line width of the alkali metal can be made broader to more closely correspond with the particular laser emission bandwidth of the selected laser. This broadening can be achieved by pressure broadening, i.e., by using a buffer gas in the optical pumping chamber. Collisions of the alkali metal vapor with a buffer gas will lead to a broadening of the alkali's absorption bandwidth.

However, since large-scale continuous flow polarizers were first introduced, their performance levels, as measured by both polarization and production rate, have fallen far short of theoretical predictions (Driehuys '08, Mortuza '03, Norquay '13). The first continuous-flow $^{129}$Xe polarizer achieved just 2-5% polarization at production rates of 1 liter/hr, while using 140 W of laser light (Driehuys '96). This stood in stark contrast to predicted polarization levels of 60-80% and production rates of 2.5 L/hr.

SUMMARY OF EMBODIMENTS OF THE INVENTION

In view of the foregoing, it is therefore an object of the present invention to provide polarization systems, methods, circuits and/or devices that reduce, suppress, eliminate and/or filter nanoclusters that can impede polarization, reduce polarization levels and/or reduce polarization life.

Embodiments of the invention are directed to flow-through optical spin exchange hyperpolarized gas production systems for producing hyperpolarized gas. The systems include a pre-saturation chamber comprising an Area Ratio (AR) of between 20 and 500, more typically between 20 and 200. The pre-saturation chamber has alkali metal therein. The systems also include a heat source in communication with the pre-saturation chamber configured to heat the pre-saturation chamber to between 140 Celsius and 300 Celsius (typically between 140 C and 250 C) and a flow-through optical pumping cell in fluid communication with the pre-saturation chamber.

The pre-saturation chamber can have an AR that is about 100.

A new and/or previously unused pre-saturation chamber can include rubidium (Rb) in an amount between 0.5 and 5 grams.

The pre-saturation chamber can be replaceably and interchangeably detachable from the hyperpolarized gas production system for another pre-saturation chamber having a common size and shape and pre-filled with the alkali metal to thereby allow for a plurality of pre-saturation chambers to be used with the same optical pumping cell over production cycles.

The system can include a pressurized flow manifold that resides upstream of the optical pumping cell and maintains a gas flow path into the optical pumping cell at a defined pressure. The pre-saturation chamber can be a detachable pre-saturation chamber that is interchangeably, sealably attached to the pressurized flow manifold to allow a first used pre-saturation chamber to be replaced with a factory-sealed pre-saturation chamber comprising the alkali metal.

The optical pumping cell can include an electrical field between about 2 kV/cm to about 20 kV/cm that is configured to attract charged nanoclusters.

The pre-saturation chamber can include a silica wick.

The system can include a control circuit with a nanocluster detection and/or suppression module configured to control operation of the system so that generation of alkali nanoclusters is suppressed to below a value of $1 \times 10^9$ per cm$^3$ over at least a 45 minute operating period.

The system can include a control circuit in communication with the optical pumping cell; a probe laser configured to project an off-resonance probe beam across the optical pumping cell; and a detector in communication with the probe laser and control circuit, positioned across from the probe laser on an opposing side of the optical pumping cell. Attenuation of a signal from the probe beam can be associated with production of nanoclusters in the gas flow stream in the optical pumping cell.

The probe laser can have a wavelength that generates a blue laser beam, optionally at a wavelength of 450 nm.

The system can include an optical pumping laser in communication with the optical pumping cell. The control circuit can direct the optical pumping laser to turn OFF and/or a heat source associated with the optical pumping cell to decrease heat output or turn OFF when nanoclusters are detected.

The probe laser can reside along one long side of the optical pumping cell and can direct the probe beam across the optical cell in a direction that is orthogonal to a direction of a spin-exchange optical pumping laser beam.

The optical pumping cell can include regional heat sources for defining an optical window on each side of the optical pumping cell for a probe laser to project across without attenuation due to alkali metal deposited onto an inner surface of the cell under the optical window.

The system can include an optical pumping laser having a wattage rating of between 200 W to 500 W.

Other embodiments are directed to optical spin exchange hyperpolarized gas production systems for producing hyperpolarized gas. The systems include a pre-saturation chamber with alkali metal; a heat source in communication with the pre-saturation chamber configured to heat the pre-saturation chamber to between 140 Celsius and 300 Celsius; an optical pumping cell in fluid communication with the pre-saturation chamber; and a nanocluster detection system in communication with the optical pumping cell.

The system may include a control circuit that includes and/or is in communication with the nanocluster suppression module that includes and/or is in communication with the nanocluster detection system.

The nanocluster detection system can include one or more of: (i) a fluorescence spectroscopy detector, (ii) an IR (infrared) camera to observe plumes, or (iii) a probe laser and associated detector.

Yet other embodiments are directed to methods of producing hyperpolarized $^{129}$Xe. The methods include electronically detecting and/or monitoring for a presence of alkali nanoclusters within a flow optical cell.

Embodiments of the invention are directed to methods for producing hyperpolarized $^{129}$Xe. The methods can include: generating hyperpolarized $^{129}$Xe gas using spin-exchange optical pumping with a continuous flow through an optical pumping cell over a defined production period; and suppressing generation of alkali nanoclusters below $1 \times 10^9$ per cm$^3$. The defined production period can be between 10-60 minutes, such as about 10 minutes, about 30 minutes, about 45 minutes or about 60 minutes.

The alkali nanocluster suppression is carried out to suppress at least one of Rb, Cs, Na, and K nanoclusters, and/or any combination thereof.

The method can include pre-saturating a noble gas mixture with vaporized alkali metal in a pre-saturation chamber having an Area Ratio (AR) of between about 20 and about 500, typically between 20 and 200, residing outside a laser exposure region of an optical pumping laser associated with the optical pumping cell.

The pre-saturation chamber can hold a silica wick.

The method can include allowing a user to interchanbeably sealably attach a new (previously unused) pre-saturation chamber with alkali metal in an amount between 0.5 grams and 5 grams, to a manifold upstream of the optical pumping cell to replace a used pre-saturation chamber having reduced amount of alkali metal therein relative to the new pre-saturation chamber.

The method can include during the generating step, electronically monitoring for nanocluster generation in the optical pumping cell.

The method can include filtering nanoclusters from the generated hyperpolarized gas.

Other embodiments are directed to pre-saturation devices for a (continuous) flow spin-exchange hyperpolarizer. The pre-saturation devices can include a pre-saturation member having an internal pre-saturation chamber, the pre-saturation member is sealably attachable to a manifold of a spin-exchange hyperpolarizer upstream of an optical pumping cell. The pre-saturation member has opposing first and second ends and alkali metal held in the pre-saturation chamber (prior to first use and/or prior to attachment to the manifold), in an amount between 0.5 grams and 5 grams.

The alkali metal can include at least one of Rb, Cs, Na, and K and/or any combination thereof with a cumulative amount, for a new and/or unused pre-saturation member, being between 1-3 grams.

The pre-saturation member can be configured for attachment to a hyperpolarizer in a sealed state to inhibit the alkali metal from being exposed to air.

The pre-saturation member can have longitudinally spaced apart end portions comprising metal seals for attaching to a pressurized fluid flow manifold on the hyperpolarizer.

The pre-saturation chamber can have an Area Ratio of between 20 and 200.

The AR can be about 100 in some embodiments.

The pre-saturation chamber can include a silica wick.

The pre-saturation member can have longitudinally spaced apart end portions comprising one or more of: (i) metal seals, (ii) valves, and/or (iii) threaded attachment segments for attaching to a pressurized fluid flow manifold on the hyperpolarizer.

Still other embodiments are directed to optical pumping cells that have an internal coating that includes one or more of polydimethylsiloxanes, paraffins, or a coating selected to hold up to alkalis metals and provide ballistic impact reduction or control to suppress cluster formation, wherein the coating comprises one or more of: a siloxane, a fluorinated and/or deuterated siloxane, a silane, a fluorinated and/or deuterated silane, a polydialkylsiloxane, a fluorinated and/or deuterated polydialkylsiloxane, a polyalkylarylsiloxane, a fluorinated and/or deuterated polyalkylarylsiloxane, polydiarylsiloxane, a fluorinated and/or deuterated polydiarylsiloxane, a polyheteroorganosiloxane, a fluorinated and/or deuterated polyheteroorganosiloxane, a paraffin, a deuterated and/or fluorinated paraffin, a hydrocarbon wax, a deuterated and/or fluorinated hydrocarbon wax, and any combination thereof.

Other embodiments are directed to methods of suppressing alkali clusters by applying electrostatic potentials to attract alkali clusters and remove them from a gas stream comprising hyperpolarized noble gas.

Some embodiments are directed to methods of suppressing alkali nanoclusters by applying electrostatic potentials to attract alkali nanoclusters to an optical pumping cell to remove alkali nanoclusters from noble gas during optical spin-exchange used to produce hyperpolarized gas.

Some embodiments are directed to methods of increasing hyperpolarized gas yields comprising: detecting and/or monitoring for the presence of alkali nanoclusters within a continuous flow optical pumping cell.

The detecting can be carried out using (a) fluorescence spectroscopy, (b) imaging with an IR camera to observe plumes, or (c) a probe beam that is attenuated by the nanoclusters but not by atomic rubidium.

The method can include using a nanocluster filter in fluid communication with the optical pumping cell to filter nanoclusters from a polarized gas flow.

Still other embodiments are directed to a hyperpolarizer with a pressurized gas flow manifold in communication with an optical pumping cell; and a voltage source configured to apply an electric field of between about 2 kV/cm to about 20 kV/cm to the optical pumping cell to thereby attract alkali nanoclusters.

As will be appreciated by those of skill in the art in light of the above discussion, the present invention may be embodied as methods, systems and/or computer program products or combinations of same. In addition, it is noted that aspects of the invention described with respect to one embodiment, may be incorporated in a different embodiment although not specifically described relative thereto. That is, all embodiments and/or features of any embodiment can be combined in any way and/or combination for any number of desired activities and/or any degree of activity performance complexity or variability. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

The foregoing and other objects and aspects of the present invention are explained in detail herein.

BRIEF DESCRIPTION OF THE DRAWINGS

Other features of the present invention will be more readily understood from the following detailed description of exemplary embodiments thereof when read in conjunction with the accompanying drawings.

FIG. 8A is a side perspective view of an exemplary optical pumping cell with a pre-saturation chamber according to embodiments of the present invention.

FIG. 8B is an end view of the device shown in FIG. 8A.

FIG. 8C is a top view of the device shown in FIG. 8A.

FIG. 8D is a back view of the device shown in FIG. 8A.

FIG. 10C is a schematic illustration of a detachable pre-saturation chamber according to embodiments of the present invention.

FIG. 11 is a schematic illustration of a cross-section of a spin-exchange optical pumping cell according to embodiments of the present invention.

FIGS. 12A and 12B are schematic illustrations of exemplary surface features of an optical pumping cell, filter, and/or polarizer flow path according to embodiments of the present invention.

FIG. 15A is a schematic illustration of a hyperpolarizer that can be configured to rotate the optical pumping cell to inhibit cluster formation or deposition according to embodiments of the present invention.

FIG. 15B is a schematic illustration of a hyperpolarizer that can be configured to vibrate the optical pumping cell to inhibit cluster formation or deposition according to embodiments of the present invention.

FIG. 16A is a schematic illustration of a hyperpolarizer with a nanocluster detection and optional optical pumping cell heat control circuit according to embodiments of the present invention.

FIG. 16B is a schematic illustration of a hyperpolarizer with a control circuit that can direct the optical pumping cell laser to have an adjustable duty cycle and/or "on" versus "off" period based on detection of or predictive formation of nanoclusters in the optical pumping cell over a production cycle/time, according to embodiments of the present invention.

DETAILED DESCRIPTION

Figure 1A:
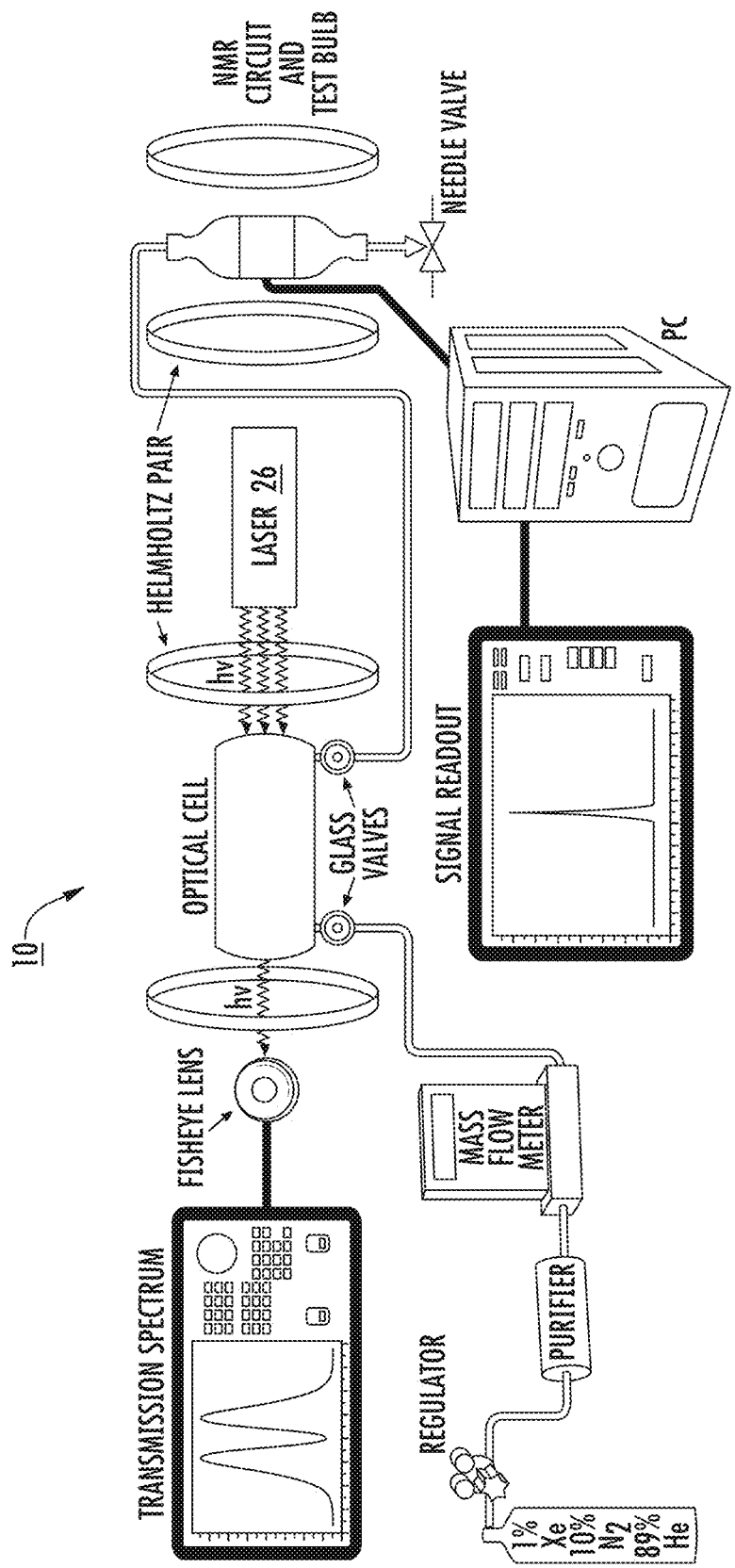
FIG. 1A is a schematic illustration of an experimental apparatus used to obtain flow curves shown in FIGS. 2A-2E and 3, for example, according to embodiments of the present invention.

The present invention will now be described more fully hereinafter with reference to the accompanying figures, in which preferred embodiments of the invention are shown. This invention may, however, be embodied in many different forms and should not be construed as limited to the embodiments set forth herein.

Like numbers refer to like elements throughout. In the figures, layers, regions and/or components may be exaggerated for clarity. The word "Figure" is used interchangeably with the abbreviated forms "FIG." and "Fig." in the text and/or drawings. Broken lines illustrate optional features or operations unless specified otherwise. In the description of the present invention that follows, certain terms are employed to refer to the positional relationship of certain structures relative to other structures.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will also be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the data or information in use or operation in addition to the orientation depicted in the figures. For example, if data in a window view of the system in the figures is inverted, elements described as "under" or "beneath" other elements or features would then be oriented "over" the other elements or features. Thus, the exemplary term "under" can encompass both an orientation of over and under. The display view may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

As used herein, the term "forward" and derivatives thereof refer to the general direction a noble gas mixture travels as it moves through the hyperpolarizer system; this term is meant to be synonymous with the term "downstream" which is often used in manufacturing environments to indicate that certain material being acted upon is farther along in the manufacturing process than other material. Conversely, the terms "rearward" and "upstream" and derivatives thereof refer to the directions opposite, respectively, the forward and downstream directions.

Also, as described herein, polarized gases can be collected, frozen, then thawed, and used in MRI applications. For ease of description, the term "frozen polarized gas" means that the polarized gas has been frozen into a solid state. The term "liquid polarized gas" means that the polarized gas has been or is being liquefied into a liquid state. Thus, although each term includes the word "gas", this word is used to name and descriptively track the gas which is produced via a hyperpolarizer to obtain a polarized "gas" product. Therefore, as used herein, the term gas has been used in certain places to descriptively indicate a hyperpolarized noble gas product and may be used with modifiers such as solid, frozen, and liquid to describe the state or phase of that product.

In some embodiments, the polarized $^{129}$Xe gas can be produced and formulated to be suitable for internal pharmaceutical human or animal medical purposes.

The term "about" means within plus or minus 10% of a recited number.

The term "polarization friendly" means that the device is configured and formed of materials and/or chemicals that do not induce or cause more than di minimis decay (e.g., less than about 2%) of the polarization of the polarized noble gas, e.g., $^{129}$Xe.

The term "compact" with respect to optical pumping cells, refers to optical pumping cells that are between about 50 cubic centimeters ("ccs") to about 1000 ccs, typically between about 100 ccs and 500 ccs, in volumetric capacity.

The term "high volume" means that the polarizer is a continuous flow polarizer (or at least substantially continuous), once activated for production for a given supply of gas mixture to produce at least between about 1.5 ccs to about 500 cc's of polarized noble gas per minute, and/or between about 1000 cc's to about 10,000 cc's, or even more, per hour. The terms "polarizer" and "hyperpolarizer" are used interchangeably.

The term "nanoclusters" is used descriptively to refer to small paramagnetic nano-size and/or microscopic size chemical structures associated with an alkali metal used in spin-exchange optical pumping that typically fluoresce, but are also not typically directly viewable by the naked eye during typical polarizer operation due to the high power of infrared laser light also present that would damage the retina. Therefore, for proper human viewing, a suitable lens, image enhancement or optical or fluorescent analysis can be employed, for example. The target nanoclusters may be associated with Rb, Cs, Na, and/or K and/or combinations thereof.

As is well known by those of skill in the art, the term "cold finger" refers to an accumulator that cools (freezes) and collects polarized gas downstream of the optical cell.

As will be discussed further herein, the polarizer 10 (FIGS. 1A, 1B, for example) can include an optical pumping cell 22 that includes an internal surface with a defined coating. The coating may comprise, for example, a siloxane, a silane, a polysiloxane, a polysilane, a (solid) paraffin, a hydrocarbon wax (e.g., paraffin wax), and any combination thereof. The exit flow path downstream of the polarizer may also include the same or a different coating configured to inhibit polarization decay and/or suppress or filter nanoclusters.

"Siloxane" as used herein refers to a —Si—O—Si— moiety. In some embodiments, a coating may comprise a polymerized siloxane (i.e., a polysiloxane). "Polysiloxane" as used herein refers to a polymer comprising at least two siloxane moieties. Exemplary polysiloxanes, include, but are not limited to, polyalkylsiloxanes including polydialkylsiloxanes (e.g., polydimethylsiloxanes, polydiethylsiloxane, polydipropylsiloxane, etc.), polyalkylarylsiloxanes, and polydiarylsiloxanes (e.g., polydiphenylsiloxane, etc.); polyheteroorganosiloxanes (e.g., a polysiloxane containing at least one heteroatom such as, but not limited to, sulfur or nitrogen); deuterated polysiloxanes, and fluorinated polyorganosiloxanes including fluorinated polydiorganosiloxanes; and any combination thereof.

"Alkyl" as used herein alone or as part of another group and/or compound, refers to a linear ("straight chain"), branched chain, and/or cyclic (e.g., aryl) hydrocarbon containing from 1 to 30 or more carbon atoms and may be saturated or unsaturated (i.e., alkenyl and/or alkynyl). An alkyl may be fully or partially unsaturated and may contain 1 or more (e.g., 2, 3, 4, 5, or more) double bonds and/or triple bonds. In some embodiments, the alkyl group may contain 1, 2, or 3 up to 4, 5, 6, 7, 8, 9, 10, 11, 12, 13, 14, 15, 16, 17, 18, 19, 20, 21, 22, 23, 24, 25, 26, 27, 28, 29, or 30 carbon atoms. Exemplary alkyl groups include, but are not limited to, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, allenyl, acetylenyl, 1-propynyl, 2-propynyl, 1-butynyl, 2-butynyl, 2-pentynyl, cyclopropyl, cyclobutyl, cyclobutenyl, cyclopentyl, cyclohexyl, cycloheptyl, cyclooctyl, and phenyl groups.

An alkyl group may optionally be substituted (a "substituted alkyl") with one or more alkyl group substituents, which may be the same or different. The term "alkyl group substituent" includes, but is not limited to, alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There may be optionally inserted along the alkyl chain one or more oxygen, sulfur, or substituted or unsubstituted nitrogen atoms, wherein the nitrogen substituent is hydrogen, lower alkyl (also referred to herein as "alkylaminoalkyl"), or aryl.

"Aryl" as used herein refers to an aromatic substituent that may be a single aromatic ring, or multiple aromatic rings that are fused together, linked covalently, or linked to a common group, such as, but not limited to, a methylene or ethylene moiety. The common linking group also may be a carbonyl, as in benzophenone, or oxygen, as in diphenylether, or nitrogen, as in diphenylamine. The term "aryl" specifically encompasses heterocyclic aromatic compounds. The aromatic ring(s) may comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group may optionally be substituted (a "substituted aryl") with one or more aryl group substituents, which may be the same or different, wherein "aryl group substituent" includes, but is not limited to, alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR$^1$R", wherein R$^1$ and R" may each be independently hydrogen, alkyl, substituted alkyl, aryl, substituted aryl, and aralkyl.

Polysiloxanes may be linear, branched, and/or cyclic. Polysiloxanes may have a random, alternating, block, and/or graft structure. In some embodiments, a polysiloxane may be cross-linked. The molecular weight of polysiloxanes can vary widely. In some embodiments, a polysiloxane may have a weight average molecular weight of about 150 to about 1,000,000 or about 1,000 to about 1,000,000. A polysiloxane may have a viscosity of about 2 to about 2000 cps; in some embodiments, a viscosity of about of 10 to about 1500 cps; and if further embodiments, a viscosity of about of 50 to about 500 cps. In some embodiments, a coating may comprise polydimethysiloxane. Polydimethylsiloxane has a structure corresponding to Formula (I).

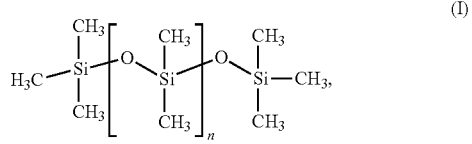

(I)

wherein n is a number from 1 to 100,000,000 or more.

"Silane" as used herein refers to a —Si— moiety, which may contain up to four hydrogen atoms. In some embodiments, a coating may comprise a polymerized silane (i.e., a polysilane). "Polysilane" as used herein refers to a polymer comprising at least two units and/or segments containing a silane. Exemplary polysilanes, include, but are not limited to, an alkylsilane, an alkylalkoxysilane (e.g., methyltrimethoxysilane, ethyltrimethoxysilane, propyltrimethoxysilane, butyltrimethoxysilane, hexyltrimethoxysilane, and octyltrimethoxysilane), a silane modified polyethylene imine, a fluorosilane, an aminoalkylsilane (e.g., aminopropylsilane), and any combination thereof.

Exemplary hydrocarbon waxes include, but are not limited to, carnauba, beeswax, candelilla, paraffin, ceresin, esparto, ouricuri, rezowax, soy wax, tallow, microwax, palm wax, mineral wax, polyethylene wax, lanolin, and/or any combination thereof.

Various techniques have been employed to accumulate and capture polarized gases. For example, U.S. Pat. No. 5,642,625 to Cates et al., describes a high volume hyperpolarizer for spin polarized noble gas and U.S. Pat. No. 5,860,295 to Cates et al. describes a cryogenic accumulator for spin-polarized $^{129}$Xe. These references are hereby incorporated by reference as if recited in full herein. As used herein, the terms "hyperpolarize" and "polarize" and the like, mean to artificially enhance the polarization of certain noble gas nuclei over the natural or equilibrium levels. Such an increase is desirable because it allows stronger imaging signals corresponding to better MRI images of the substance and a targeted area of the body. As is known by those of skill in the art, hyperpolarization can be induced by spin-exchange with an optically pumped alkali-metal vapor or alternatively by metastability exchange. See Albert et al., U.S. Pat. No. 5,545,396, which is incorporated by reference as if recited in full herein.

The production of hyperpolarized (HP)$^{129}$Xe by spin-exchange optical pumping (SEOP) has led to many applications in scientific and medical research (Goodson '02). Polarized $^{129}$Xe is used in a variety of studies such as electric dipole moment (EDM) searches (Romalis '01), surface characterization (Springuel-Huet '99), protein binding (Schröder '06), biosensor development (Lowery '03, Spence '01), cell spectroscopy (Wolber '00), cross-polarization (Navon '96), and, of course, biomedical MRI (Mugler '13). Particularly for clinical MRI, where scanner time is limited, it is desirable that HP $^{129}$Xe be produced or generated with both high polarization and a high volume production rate.

The most common approach to $^{129}$Xe polarization uses optical pumping and spin exchange (SEOP), wherein angular momentum is first transferred from laser photons to an alkali metal such as Rb, and subsequent collisions transfer a portion of the absorbed angular momentum to the $^{129}$Xe nuclei through a Fermi-contact hyperfine interaction (Walker '97). The primary means to achieve both high polarization and high production rate is to employ a lean $^{129}$Xe and buffer gas mixture, flowing continuously through a Rb-filled optical pumping cell illuminated with tens to hundreds of Watts of 795 nm laser light, resonant to the D1 absorption of Rb. HP $^{129}$Xe can be subsequently separated from the other gases by cryogenic extraction (Driehuys '96).

However, since large-scale continuous flow polarizers were first introduced, their performance levels, as measured by both polarization and production rate, have fallen far short of theoretical predictions (Driehuys '08, Mortuza '03, Norquay '13). Subsequent years saw numerous improvements that should have positively impacted polarizer performance. Initially, laser beam profiles, optics, and optical cell quality were improved so that more power illuminated the optical cell more homogeneously. But little substantial gain was realized. Furthermore, significant improvements in laser performance, such as line narrowing the spectral profile from ~2 nm to ~0.2 nm, did not yield nearly the advantages they should have. Even application of greatly increased laser power (Zook '02) led to negligible improvements in both polarization and production rate. Moreover, additional phenomena were reported that could not be readily explained by standard models of spin exchange optical pumping (SEOP). For example, polarization increased when more $N_2$ quenching gas was added, or when lasers were deliberately detuned from the Rb D1 resonance (Nikolaou '09). Additionally, polarizers operating with richer xenon mixtures and attendant higher spin destruction rates (Nikolaou '09), actually exceeded in many cases, the performance of polarizers using lean $^{129}$Xe mixtures, which should have exhibited lower spin destruction and thus maintained higher alkali and $^{129}$Xe polarization. Most fundamentally, perhaps the most unrecognized discrepancy has been the inability to increase $^{129}$Xe production rate by simply scaling up the laser power.

In principle, $^{129}$Xe production rate should increase as more laser light is absorbed. As introduced by Bhaskar, et al. (Bhaskar '82), the fraction of Rb-$^{129}$Xe collisions resulting in spin exchange rather than alkali spin destruction, determine the overall photon efficiency with which circularly polarized photons are converted into nuclear spins. The photon efficiency for $^{129}$Xe-Rb spin exchange in the commonly used binary and short molecular lifetime regime (Nelson '01) was recently re-calculated by Norquay, et al. (Norquay '13) to be 4.6%. That is to say for every Watt of 795 nm light absorbed by the $^{129}$Xe-Rb system, it should be feasible to produce 25 mL/hr of polarized $^{129}$Xe. Hence, a polarizer absorbing 100 W of laser light, should readily produce 2.5 L/hr, and absorbing 200 W, should produce 5 L/hr, etc. In practice, however, most systems achieve nowhere near the respective therotetical production rates.

Ruset et al. (Ruset '06) introduced a massively scaled-up polarizer design. This work introduced several design changes—1) a vertical orientation, 2) a very large optical cell, ~1.8 m in length, 3) lower pressure operation with line-narrowed lasers, 4) pre-saturation of the gas stream with Rb vapor, 5) a cooling region prior to $^{129}$Xe exiting the cell, and 6) a freeze-out spiral for cryogenic accumulation. This design also touted a "counter-flow" approach, with $^{129}$Xe flowing towards the laser, but this had been a part of every flow-through $^{129}$Xe production design ever published (Driehuys '96, Imai '08, Korchak '13, Rosen '99, Schrank '09, Walter '01, Zook '02). However, polarizations of 50% and production rates of 1.2 L/hr were reported. This large-scale production system (and subsequent modifications) is now being developed by Xemed, LLC, Durham, N.H., with the product "XeBox-B10" Polarizer and the polarized gas, MagniXene™ $^{129}$Xe. See also, U.S. Pat. Nos. 7,719,268 and 7,928,359, the contents of which are hereby incorporated by reference as if recited in full herein.

Although the work of Ruset, et al. has increased production rates with a relatively large system, a fundamental explanation for the improved performance has not yet been provided (Hersman '08). Moreover, even this enlarged design did not achieve anywhere near theoretical photon efficiency. Clinical field testing of this device has led to highly variable results, the reasons for which are poorly understood (Shukla '12). This design was characterized by Schrank, et al. (Schrank '09), albeit with more modest 30 W laser power, and this work showed that the alkali polarization was close to theoretical prediction.

The larger polarizer designs employing optical cells with volumes of several liters and operating at relatively cooler temperatures may confer a design advantage over the earlier "small and hot" designs employing optical cells with volumes of a few hundred ccs (cubic centimeters) operating at higher temperatures to absorb the available light.

More recently, Nikolaou et al. has stated that they can achieve very high $^{129}$Xe polarization, albeit while absorbing very little laser light. Unfortunately, this system is a batch system rather than flow polarization and therefore exhibits slow production rates. However, both the work of Ruset and Nikolaou demonstrate that there are regimes or times where $^{129}$Xe polarizer performance can approach theoretical predictions. Nonetheless, the ability to reliably sustain such high performance has yet to be demonstrated as, until now, important underlying contributors to sustaining high performance was not recognized or understood.

The ability to rapidly produce hyperpolarized $^{129}$Xe with high polarization can be important for facilitating biomedical imaging applications. However, systems built to date suffer from second order effects that prevent the realization of this goal routinely and reliably. Those polarization systems that do achieve intermittent relatively good performance are exceedingly bulky and expensive to build. Further, even so, the high yield performance can be unpredictable and not guaranteed to remain stable. Thus, it is believed that the field of hyperpolarized gas MRI is handicapped from moving forward because hyperpolarized $^{129}$Xe production cannot be scaled up reliably and cost-effectively.

To help solve this long standing problem, a detailed study of both $^{129}$Xe polarization and production rate for a continuous flow polarizer operating with three different cell geometries and two different laser configurations (line narrowed and free-running) was conducted. When these results are compared with a standard model of optical pumping and spin exchange, a clear and systematic reduction in both polarization and production rate becomes evident. These results can be well explained by proposing that laser optical pumping also generates paramagnetic Rb nanoclusters. Such cluster formation has recently been reported in the unrelated field of heat pipe technology (S. N. Atutov '12). Specifically, while not wishing to be bound to any single theory, it is believed that Rb nanoclusters cause both Rb spin destruction and $^{129}$Xe spin relaxation as well as a small degree of unproductive scattering of incident laser photons. When the generation of these nanoclusters and their additional deleterious effects are added to the standard model, it predicts the observed polarizer performance.

With the understanding of Rb nanocluster formation as a source of long-standing unreliable performance of $^{129}$Xe polarizers, solutions to suppress their formation can be identified and developed. When Rb nanocluster formation is suppressed, polarizer performance returns to theoretically predicted levels. This means for every Watt of laser light that is absorbed by the system, a higher $^{129}$Xe polarization is attained and more $^{129}$Xe atoms are polarized than is presently the case. Furthermore, suppression of nanoclusters now permits scaling up polarizer performance in a well-understood fashion. In other words, if absorbing 100 W of light enables production of 2.5 liters/hr, then absorbing 200 W of light will enable 5.0 liters/hr to be produced, and so on. In fact, absorption of several hundred Watts of resonant laser light can begin to yield virtually "on-demand" production of polarized $^{129}$Xe to facilitate MRI imaging applications.

Embodiments of the invention propose several approaches to detect, suppress, inhibit and/or prevent Rb nanocluster formation and/or to filter Rb nanoclusters. While the description is primarily discussed with respect to Rb for producing target nanoclusters, it is contemplated that related suppression and/or filtering technology can be used for other paramagnetic nanoclusters associated with spin-exchange pumping.

In traditional compact flow-through optical cell designs, there is significant bulk Rb within the body of the optical cell where optical pumping takes place. When such bulk Rb is impacted by excited state Rb, it can lead to explosive generation of Rb nanoclusters. Thus, one action is to remove bulk alkali metal from the main optical pumping chamber and thereby eliminate the available surface area for nanocluster generation. This may be carried out by moving the bulk Rb to a "pre-saturation" region of the system, so that only or substantially only atomic Rb vapor is added to the flowing gas stream and the source gas mixture with the Rb vapor mixture together enters into the optical pumping chamber.

However, over time, sufficient Rb vapor may enter the optical pumping chamber such that bulk Rb becomes available within the chamber and again starts forming clusters. To inhibit this action, the optical pumping chamber 22 (FIG. 1A, 10) can include an internal coating 22c (FIG. 11) such as a siliconizing agent or similar polymer that inhibits or prevents bulk formation of alkali pools that unduly impact polarization. Moreover, these surface polymer agents may better absorb the collisional impact of excited alkali atoms and therefore suppress cluster formation even once significant Rb begins to accumulate in the optical chamber.

Figure 10A:
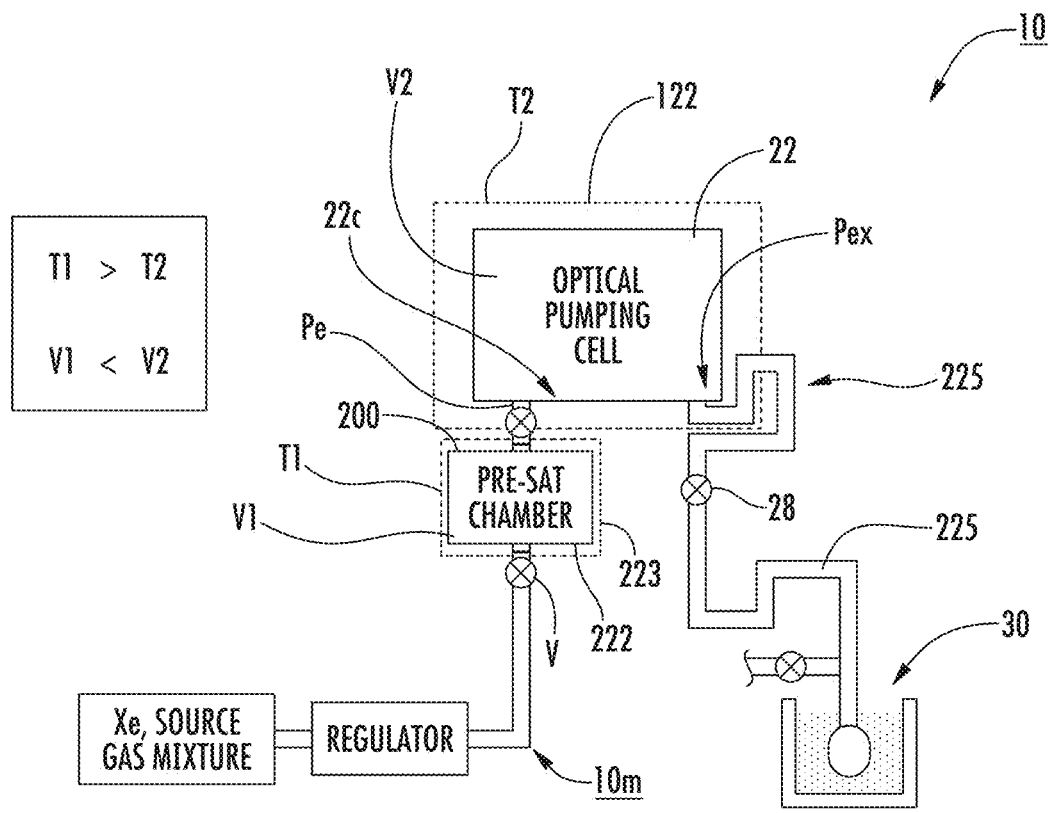
FIG. 10A is a schematic illustration of a polarization system with a pre-saturation chamber according to some embodiments of the present invention.

Furthermore, while nanoclusters are deleterious to the optical pumping and spin-exchange process, they may also have a negative impact downstream of the polarizer if they remain in the gas stream exiting the optical cell and entering into the cold finger. Hence, nanocluster filtering with at least one nanocluster filter 225 can alternatively or additionally be used in a flow path proximate an exit of the pumping cell, typically between the optical pumping cell 22 and the cold finger 30 (FIG. 10A). Further discussion of exemplary nanocluster suppression and/or filters is provided below.

It is contemplated that embodiments of the invention will allow compact flow-through $^{129}$Xe polarizers 10 (FIGS. 1A, 1B, 10A, for example) to be produced in a cost-effective manner, while achieving theoretically predicted performance routinely and reliably.

Moreover, the discovery of nanoclusters and suppression configurations and operations now potentially allows the use of Cs-based optical pumping and spin exchange to be implemented commercially. It's likely that prior failed efforts to generate benefit from Cs-$^{129}$Xe spin exchange efficiency (Couture '08) were also undermined by Cs nanocluster formation.

Modeling

The standard model of Spin Exchange Optical Pumping (SEOP) can be used to relatively precisely predict $^{129}$Xe polarization and production rate for a given combination of gas mixture, laser configuration, and cell geometry. The standard model was introduced by Wagshul and Chupp (Wagshul '89) in 1989 and was recently updated by Norquay, et al. to include the latest measured spin exchange and spin destruction cross sections (Norquay '13). See, Norquay et al., Optimized production of hyperpolarized 129 Xe at 2 bars for in vivo lung magnetic resonance imaging; Journal of Applied Physics 2013; 113(4):044908-044908-044909, the contents of which are hereby incorporated by reference as if recited in full herein. This model can be used to predict $^{129}$Xe polarizer performance as a function of laser absorption for a variety of laser and cell geometry configurations in a standard polarizer.

For the purposes of practically characterizing the output of a flow-through polarizer, it is convenient to cast this expression in terms of the mass flow rate of gas, F, through the optical cell, which is related to Xe residence time according to $t_{res}=V_{cell}[G]/F$, where $V_{cell}$ is the cell volume and [G] is the total gas density in the cell, in amagats. The above equation can be expressed as $$P_{Xe}(F)=P_0(1-e^{-F_{crit}/F}) \quad \text{Equation (1)}$$

Where $F_{crit}$ is the critical flow rate at which Xe atoms spend, on average, one spin exchange time constant in the optical cell before exiting, and $P_0$ describes the peak $^{129}$Xe polarization at zero flow. In fact, this permits us to simply define the $^{129}$Xe production rate as the $F_{Xe}=f\times F_{crit}$ where f is the fraction of xenon in the gas mixture. A typical experiment characterizes both peak polarization $P_0$ and xenon production rate $F_{Xe}$ by collecting these flow curves at a variety of levels of laser absorption.

Experiments were performed on a commercially available polarizer (Model 9800, Polarean, Inc., Durham, N.C.), fitted either with the standard 300 cc SEOP cell, or retrofitted with custom-designed alternative cells with internal volumes of 100 or 200 cc. To measure the effects of laser narrowing, two different fiber-coupled diode laser arrays were used: a broadband, 111 W, 1.92 nm FWHM laser (Dual FAP, Coherent, Inc., Santa Clara, Calif.), and the second, a line-narrowed, 71 W, 0.39 nm FWHM laser (QPC Lasers, Laser Operations LLC, Sylmar, Calif.). Light from these systems was coupled via a 200 cm fiber optic to an optics box that collimated the beam, split it into horizontally and linearly polarized components, and circularly polarized each. The two beams were adjusted to maximize light transfer to the cells such that the transverse beam crossed in the middle of the cell. For the broad laser, it is estimated that 94 W of light was coupled into the cell, and for the narrowed laser, 60 W were coupled in. This 15% reduction in incident photon intensity results from reflective losses at the glass interfaces on the oven and cell face.

For each combination of laser and optical cell, polarization vs. gas flow curves were acquired with increasing degrees of laser absorption. A gas mixture of about 1% Xe (natural abundance), about 10% $N_2$, and about 89% $^4$He flowed through the optical cell at 6 atm pressure. Upon exiting the optical cell, the gas mixture was directed via a 150 cm length of 6.4 mm O.D. polyurethane tubing to a ~50 cc test bulb housed in a volume NMR coil in the center of a Polarean 2881 polarization measurement station. This system acquires $^{129}$Xe NMR at 25 kHz and has sufficient sensitivity to detect $^{129}$Xe polarized to 25% in the natural abundance dilute mixture with a single shot SNR of ~20. The experimental polarizer configuration is shown in FIG. 1A. The standard, flow-through SEOP configuration is shown, modified so that instead of flowing through a cryogenic collection device, the polarized gas is sent directly to a nearby NMR test bulb, where its signal can be probed by an RF pulse.

Figure 1B:
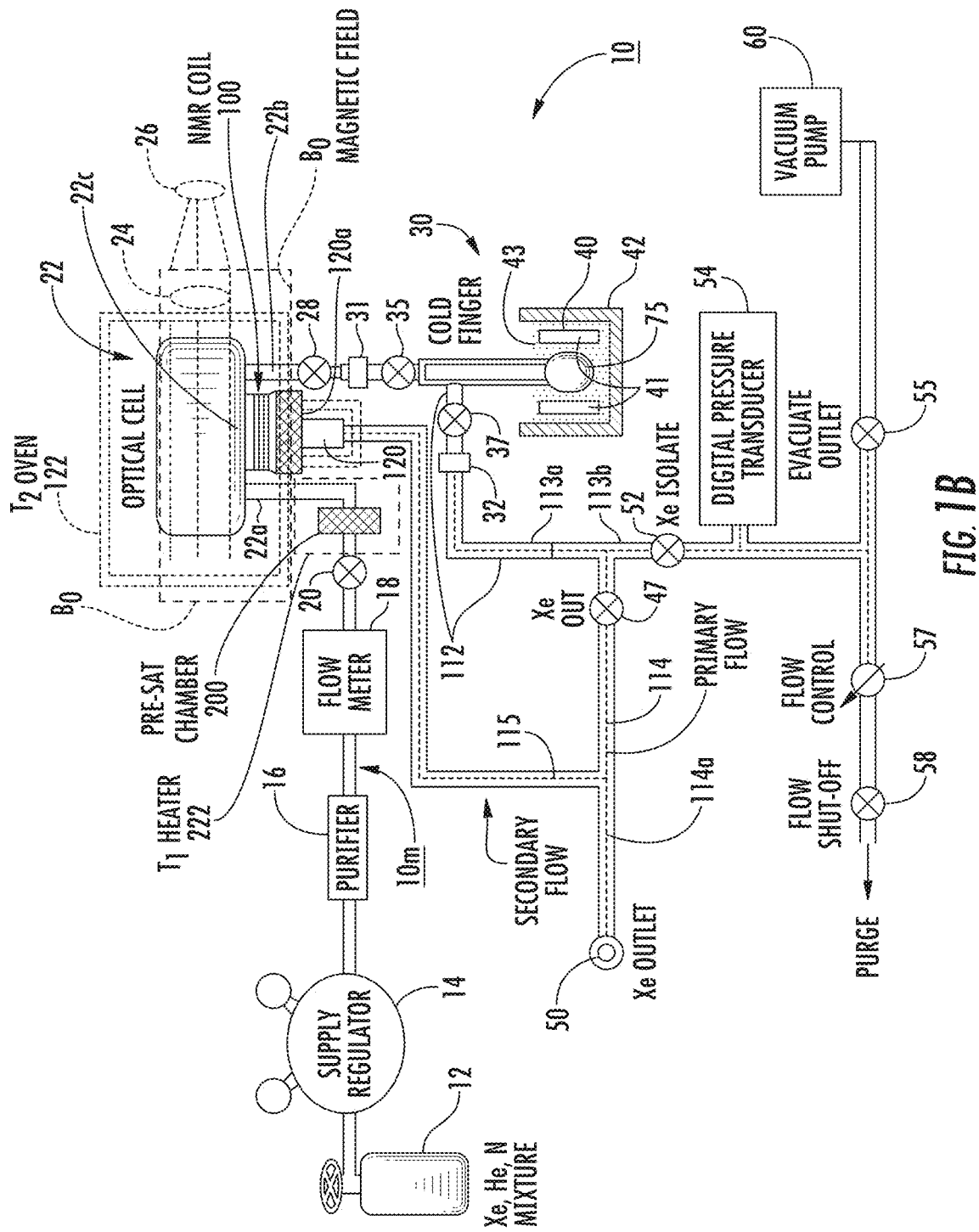
FIG. 1B is a schematic illustration of a hyperpolarized gas polarization system comprising a pre-saturation chamber according to embodiments of the present invention.
Figure 2A:
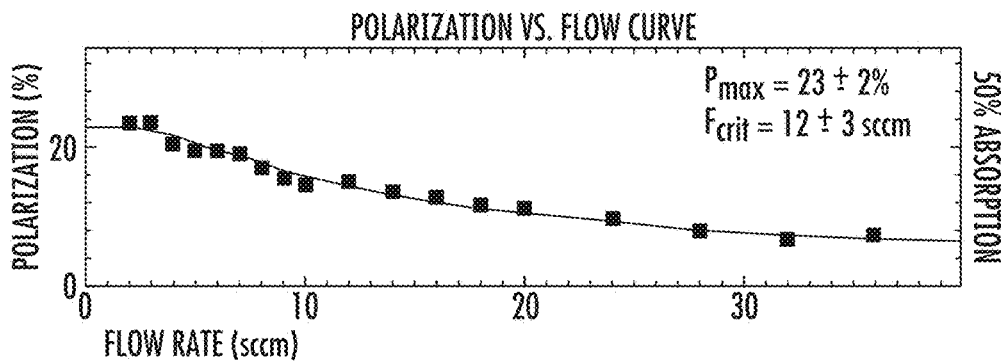
FIGS. 2A-2E are flow curves of percent polarization versus flow rate (sccm) at various absorption percentages acquired for one experimental set-up with a 300 cc SEOP and a line-narrowed laser.
Figure 2B:
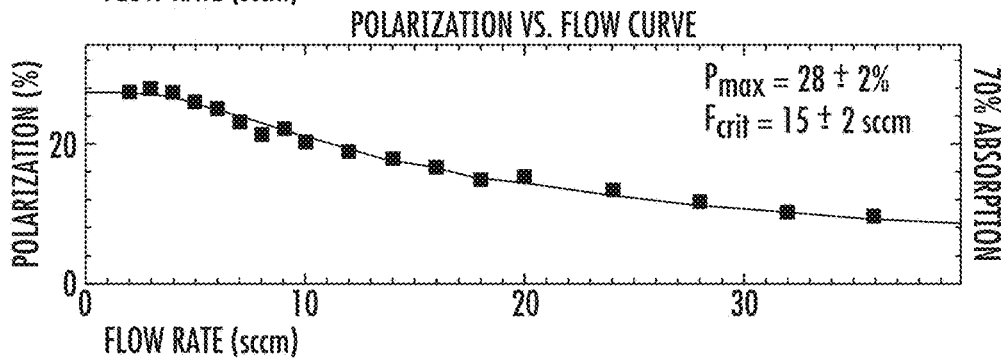
Figure 2C:
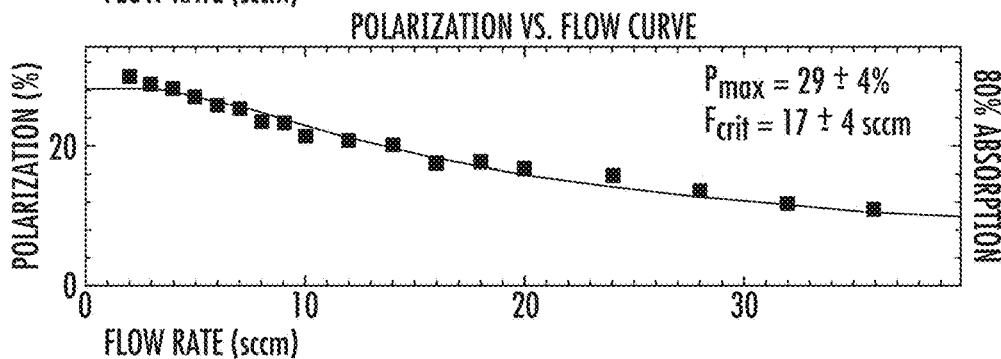
Figure 2D:
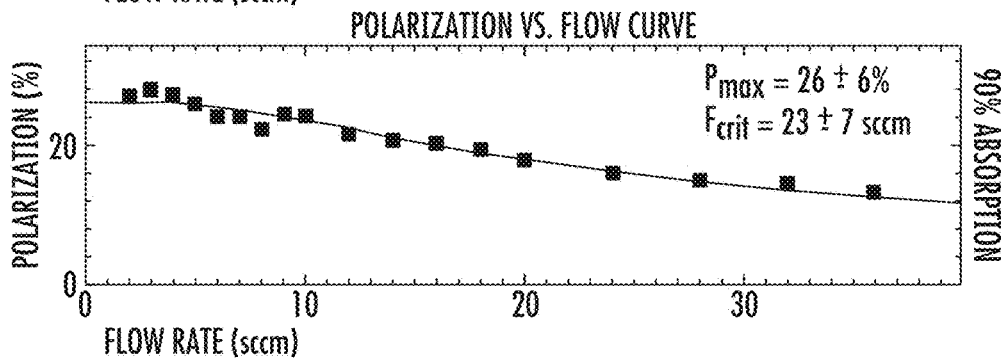
Figure 2E:
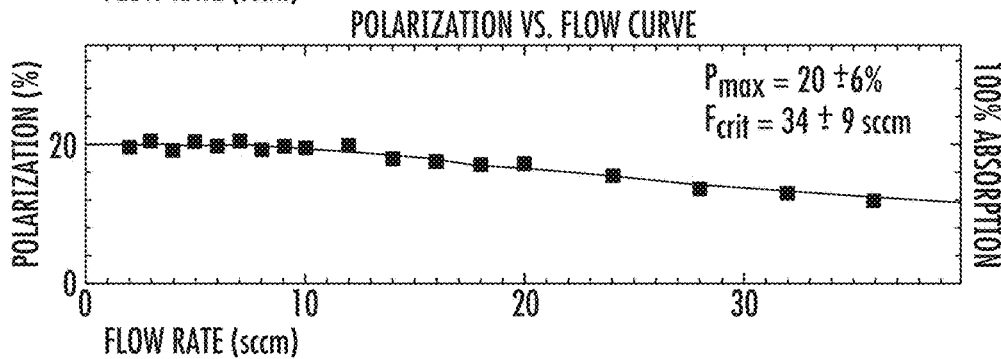

FIG. 1B illustrates a polarizer 10 that includes at least one pre-saturation chamber 200. The chamber 200 can be relatively compact and can reside adjacent the entry port Pe of the optical pumping cell 22. The polarizer 10 may also include at least one nanocluster filter 225 residing between the exit port Pex of the polarizer cell 22 and the cold finger 30, typically residing adjacent the exit port Pex. The polarizer 10 can include other components as is known by those of skill in the art (and are described below).

FIGS. 2A-2E are graphs which depict representative polarization (%) vs flow curves (flow rates, sccm) acquired using the line-narrowed laser illuminating a standard 300 cc optical cell, at 50% (FIG. 2A), 70% (FIG. 2B), 80% (FIG. 2C), 90% (FIG. 2D) and 100% (FIG. 2E) absorption. The polarization data was obtained while xenon flow rates were adjusted from 2-36 sccm. A few trends are evident from these curves. At the lower 50% laser absorption, a peak polarization of 23±2% is observed, and a xenon production rate of 12±3 sccm. As absorption increases, the peak polarization begins to drop modestly as xenon production rate begins to increase. For the highest 100% absorption point, the peak polarization decreases to 20±6%, while production rate increases to 34+/−9 ml/min. The fits to the curves can be used to extract peak polarization, Pmax, and critical flow rate, Fcrit, which measures xenon production rates.

Figure 3:
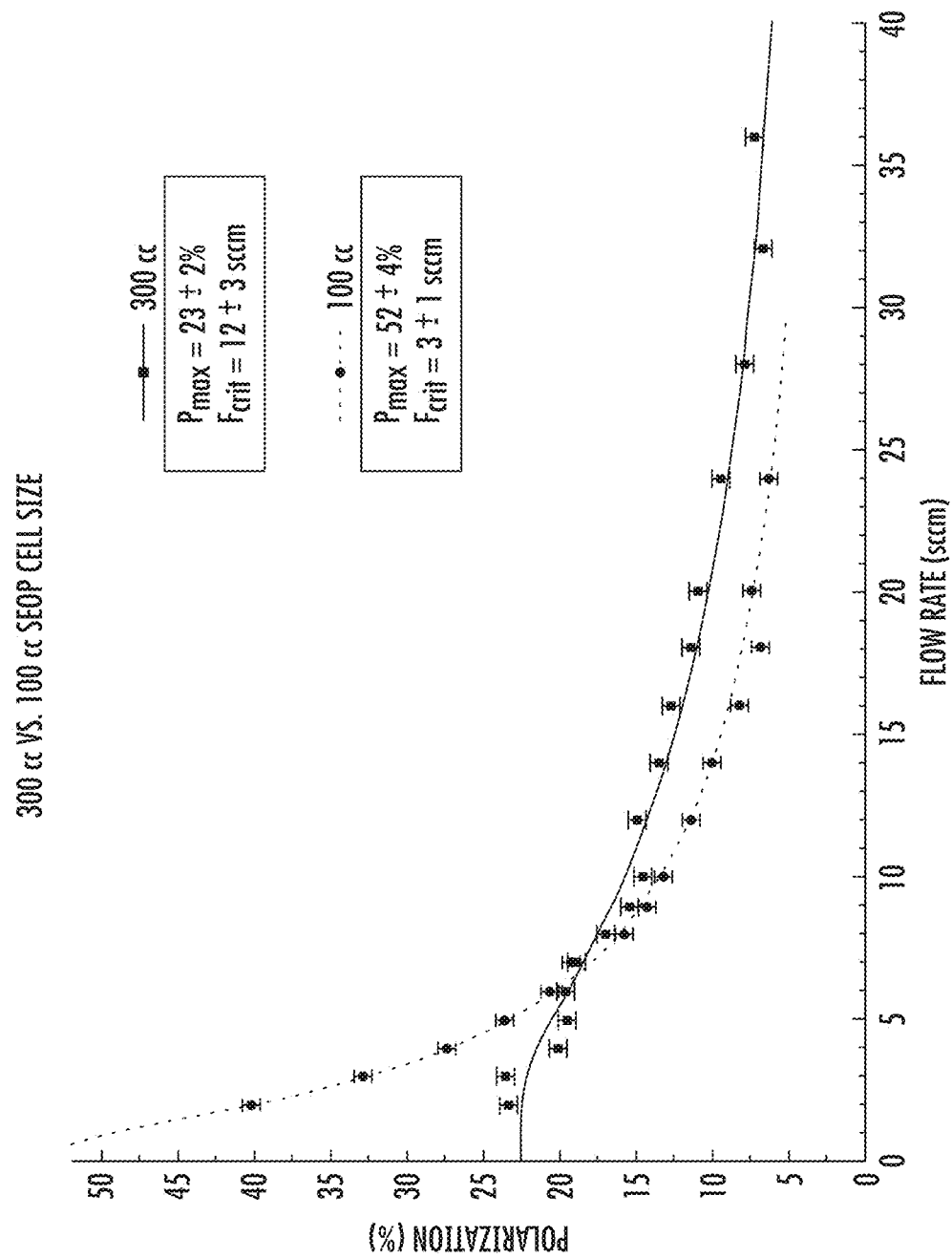
FIG. 3 is a graph of flow rate (sccm) versus polarization (percentage) of data acquired using a small cell (100 cc) and a larger cell (300 cc) which illustrates scaling up maximum polarization as cells become smaller and the scaling up of critical flow rate as cells become larger.
Figure 4A:
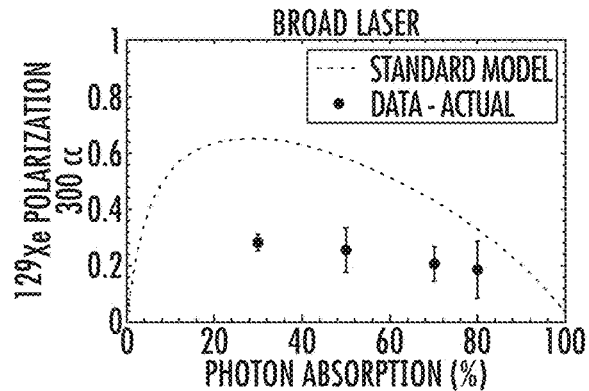
FIGS. 4A-4F are graphs of 129Xe polarization for various size SEOP cells and broad laser (FIGS. 4A, 4C, 4E) versus narrow lasers (4B, 4D and 4F) versus photo absorption (percentage) (expected as a fraction of laser light) for a conventional (standard) model and actual data.
Figure 4B:
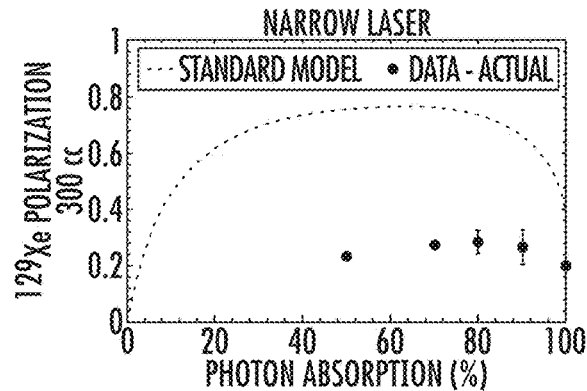
Figure 4C:
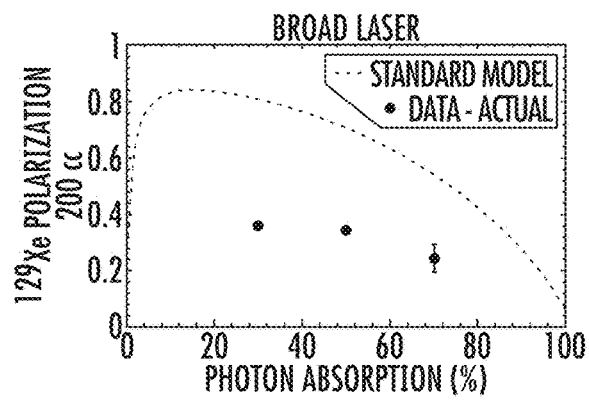
Figure 4D:
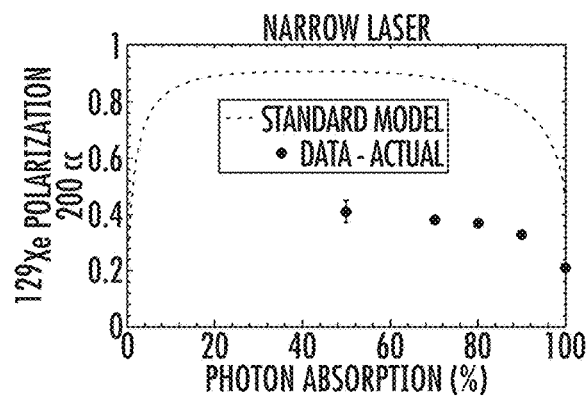
Figure 4E:
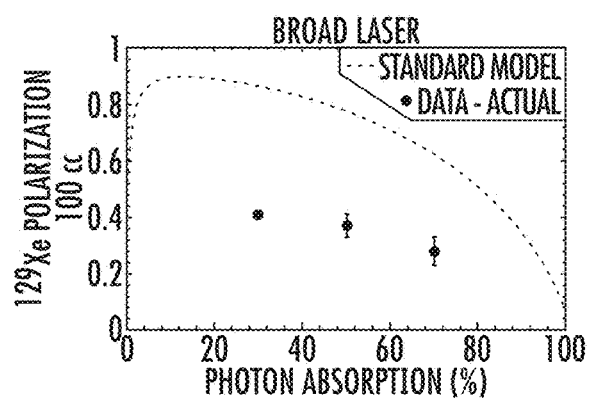
Figure 4F:
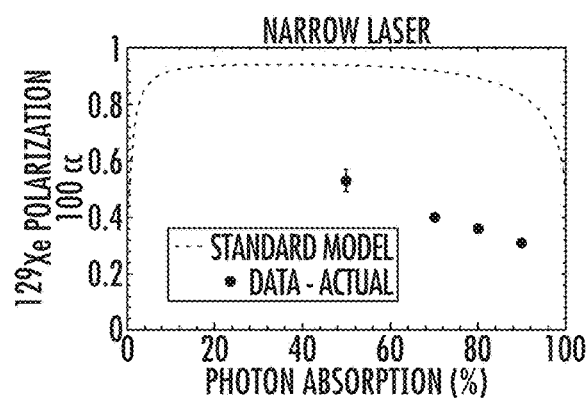
Figure 5A:
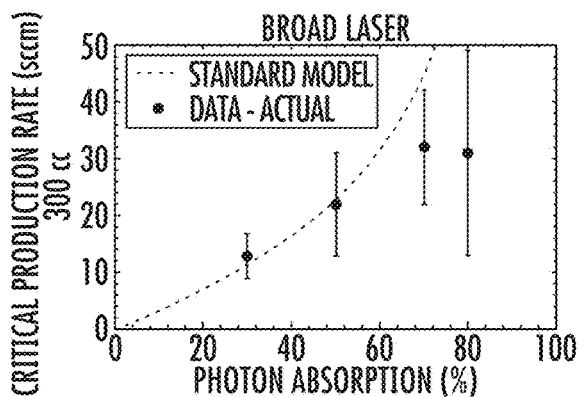
FIGS. 5A-5F are graphs of critical flow rate (sccm) versus photon absorption (%) for different size SEOP cells and broad laser (FIGS. 5A, 5C, 5E) and narrow (spectral width) laser (FIGS. 5B, 5D, 5F) for a conventional (standard) model and actual data.
Figure 5B:
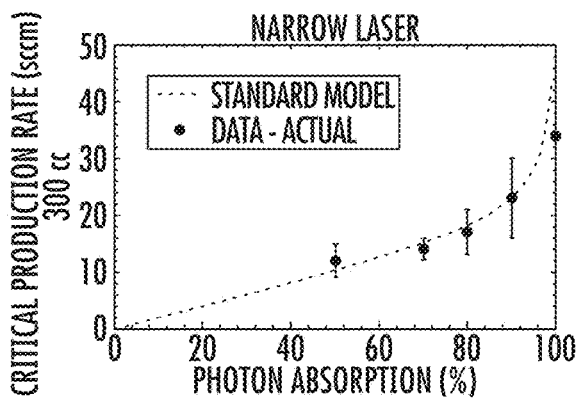
Figure 5C:
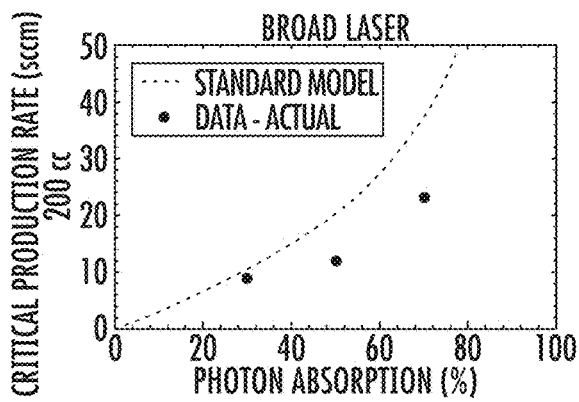
Figure 5D:
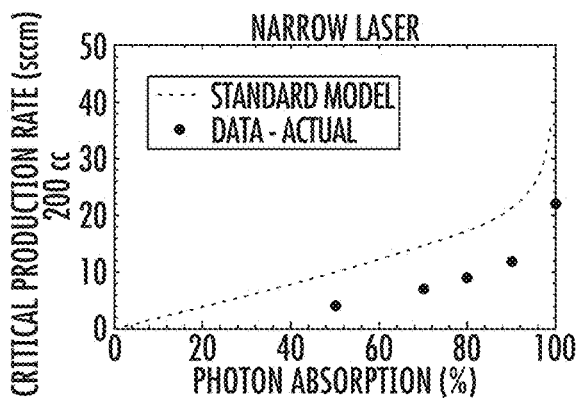
Figure 5E:
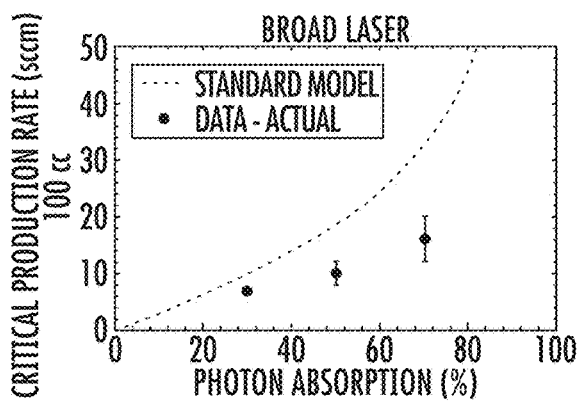
Figure 5F:
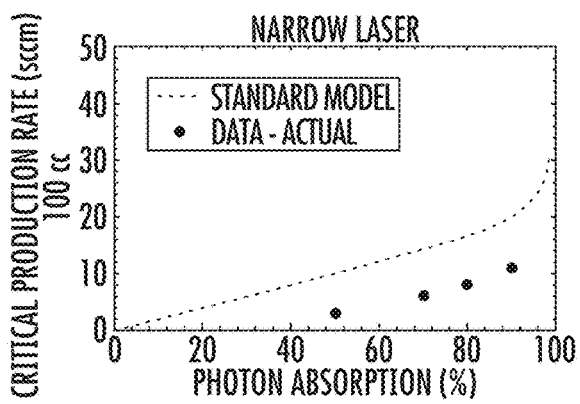
Figure 6A:
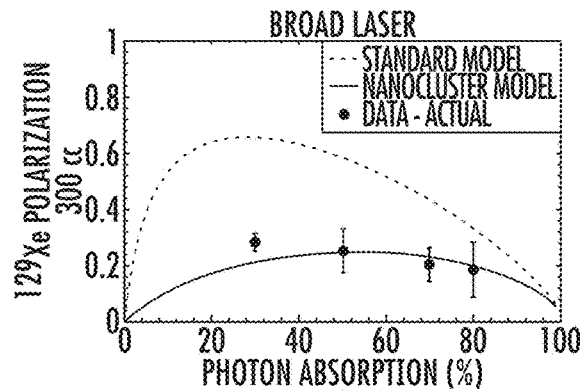
FIGS. 6A-6F are graphs of polarization (maximum 1) versus photon absorption (%) for broad laser (FIGS. 6A, 6C, 6E) and narrow (FIGS. 6B, 6D and 6F) similar to the graphs shown in FIGS. 4A-4F but including a polarization prediction model that accounts for relaxive effects of Rb clusters according to embodiments of the present invention.
Figure 6B:
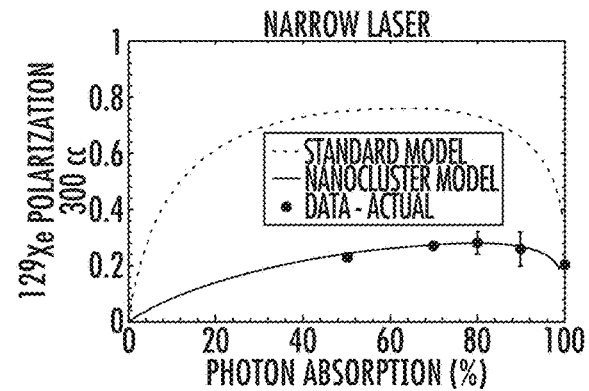
Figure 6C:
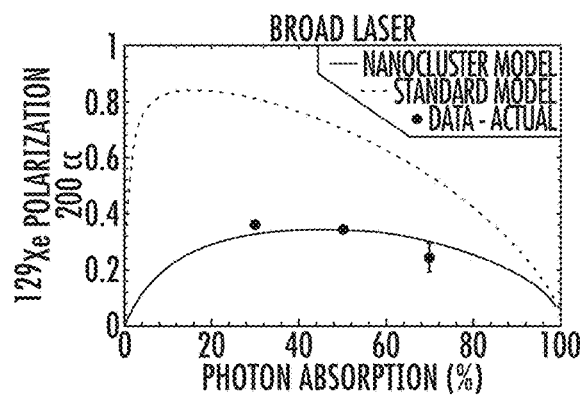
Figure 6D:
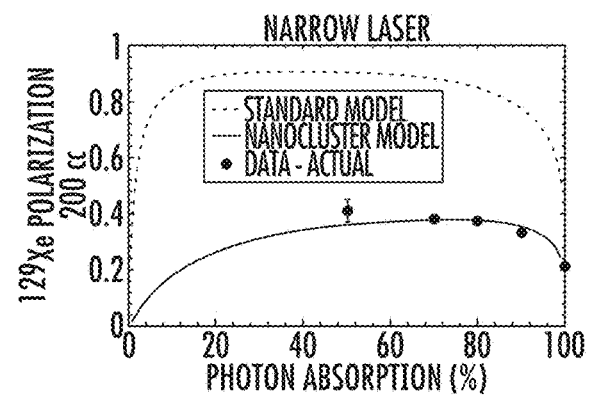
Figure 6E:
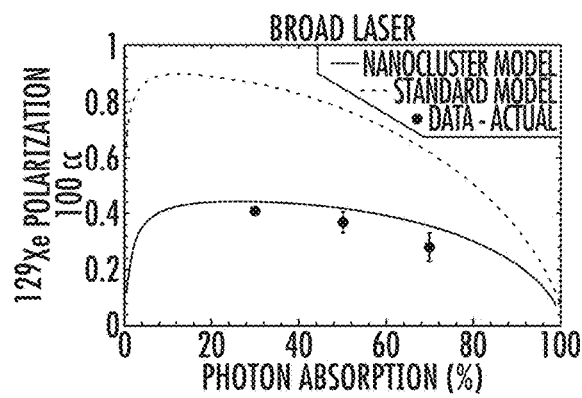
Figure 6F:
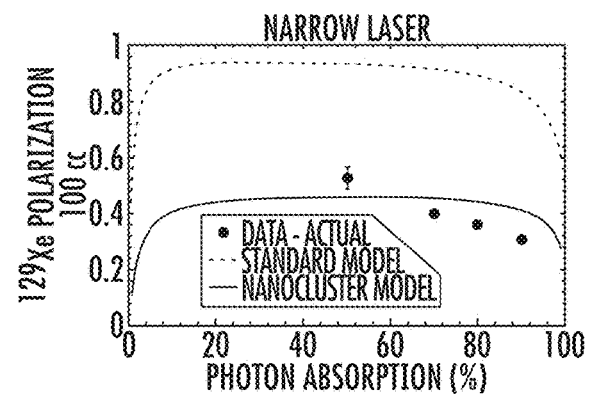

FIG. 3 is a graph of polarization (%) versus flow rate (sccm) for a 100 cc optical cell and a 300 cc optical cell for direct comparison. As shown, the scaling up of maximum polarization as cells become smaller, and the scaling up of critical flow rates as cells become larger is evident.

FIGS. 4A-4F and 5A-5F show plots of peak $^{129}$Xe polarization and xenon production rate ($f \times F_{crit}$) as a function of laser absorption for combinations of cell geometry and laser configuration. Superimposed on these figures are curves of predicted polarization and production rate based on the standard model. These comparisons across a range of laser absorptions illustrate a clear and systematic discrepancy between observed data and model predictions. Beginning with the 300 cc cell pumped with the line-narrowed laser, at low absorption, $^{129}$Xe polarization is nearly 3-fold lower than predicted. This gap narrows to roughly 2-fold at the highest absorptions. However, xenon production rate appears to agree very well with prediction and increases with absorption as expected. The closer agreement is partially attributable to the fact that the narrower spectrum laser light doesn't require [Rb] to be nearly as high in order to absorb all available photons, since those photons are much better matched to the Rb D1 resonance.

When the same 300 cc cell is pumped with the broad laser, peak $^{129}$Xe polarization is nearly 2-fold lower than predicted at low absorption, but approaches the model at higher absorptions. The production rate for this laser/cell combination matches model predictions at low absorption, but deviates badly at the higher absorption levels. For the broad laser, the standard model predicts high xenon production rates as absorption increases because it involves absorbing the most off-resonant photons, which can only happen at very high [Rb] given the small off-resonance cross-section. High [Rb] in turn would yield high spin exchange rates and hence high production rates. However, such high production rates are not seen for the broad laser, suggesting other photon scattering mechanisms may be coming into play.

Inspection of $^{129}$Xe polarization for the smaller 200 and 100 cc cells show similar discrepancies with the model predictions for both laser configurations. With broad laser pumping, $^{129}$Xe polarization again starts roughly 2× below predictions at low absorption, with slight convergence towards model predictions at higher absorptions, although less so than seen with the 300 cc cell. For the narrowed laser, the $^{129}$Xe polarization discrepancy with the model is greater and remains consistently so across the range of absorption values. Observing such low $^{129}$Xe polarization even as the available laser light is being concentrated over progressively smaller areas is suggestive of a mechanism whereby increasing laser intensity is not productively deployed for spin exchange polarization.

An additional discrepancy between model and measured data lies in the reduced $^{129}$Xe production rates obtained with the smaller 200 and 100 cc cells. When employing the broad laser with low absorption, xenon production rate already falls below expectations for both cells. The discrepancy between observed production and model predictions is greatest as absorption increases. When narrowed laser pumping is used, the production rate for these smaller cells remains consistently a factor of two below model predictions. For example, when absorbing 50% of narrowed light, the 200 cc cell produces just 12±2 sccm of HP xenon, whereas roughly twice that value is predicted. This underproduction remains roughly 2-fold below predicted values across the entire range of absorption for the narrowed laser. These findings suggest that despite concentrating the available light into smaller volume cells, the resulting absorption of higher intensity of laser light is not being productively converted into polarized $^{129}$Xe nuclei.

Revising the Model to Include (Rb) Nanoclusters

The observations and analysis presented thus far have pointed to the need to extend the standard SEOP model in two ways. Particularly, a mechanism that dramatically suppresses the $^{129}$Xe polarization at low absorption is desired while still permitting high alkali polarization at low absorption, as measured by Schrank and co-workers. Thus, it is believed that a highly paramagnetic species is present that rapidly relaxes the polarized $^{129}$Xe. It is contemplated that due to the low polarization, relaxation must be faster than spin exchange. Moreover, this mechanism may become stronger at higher laser absorption. This mechanism must also somehow disproportionately "punish" the higher optical pumping efficiency of the narrowed laser relative to the broad one. The mechanism scatters off-resonant laser photons much more potently than atomic Rb. This type of mechanism can account for the remarkably efficient absorption of the wings of the broad laser, which occur at far lower temperature and thus lower [Rb] than expected.

Based on these factors, the inventors propose that the deleterious effects observed are caused by the formation of Rb nanoclusters likely resulting from high intensity laser irradiation of alkali metal atoms near bulk alkali pools on the optical cell surface. This hypothesis is supported by the recent work of Atutov, et al., who reported on the generation of such clusters in heat pipes irradiated with low power resonant D1 light (SN Atutov '12). Atutov proposes that clouds of nanoclusters can exist with lifetimes ranging from a fraction of a second to several seconds. These authors estimate the clusters to have a size of roughly 600 nm, and to be highly paramagnetic. See, Atutov S N, Plekhanov A I, Shalagin A M, et al Explosive evaporation of Rb or K fractal clusters by low power CW radiation in the presence of excited atoms. European Physical Journal D 2012; 66(5); 1-5, the contents of which are hereby incorporated by reference as if recited in full herein.

Nanocluster Relaxation of $^{129}$Xe

The presence of sufficient amounts of paramagnetic nanoclusters would strongly relax $^{129}$Xe nuclei. This collisional relaxation can be mathematically modeled as $$\frac{1}{T_{1Xe}} = [Rb_n]\langle\sigma_{cluster-Xe}v\rangle \qquad \text{Equation (2)}$$

where $\langle\sigma_{cluster-Xe}v\rangle$ is the velocity-averaged cluster-induced relaxation cross section. Given their large size, nanoclusters should exhibit a much larger collisional cross-section with $^{129}$Xe than would their atomic Rb counterparts. From purely geometrical considerations we estimate collision cross sections with nanoclusters to be 6 orders of magnitude larger than Rb-$^{129}$Xe. Assuming a less efficient spin interaction than for Rb-$^{129}$Xe, and through steepest descent curve fitting detailed below, we arrive at an estimated velocity-averaged cross section of $<\sigma_{cluster-Xe}v> \approx 10^{-13}$ cm$^3$s$^{-1}$.

Nanocluster Spin Destruction—

If nanoclusters have a relaxing effect on $^{129}$Xe, they likely also cause spin destruction of the polarized Rb atoms. This spin destruction can be characterized using the standard formalism $$\Gamma_{SD_{clusters}} = [Rb_n]<\sigma_{cluster-Rb}v> \qquad \text{Equation (3)}$$

where $<\sigma_{cluster-Rb}v>$ is the velocity-averaged cluster-induced relaxation cross section for atomic Rb. Through similar estimates as outlined above we estimate this cross section to be $<\sigma_{cluster-Rb}v> \approx 6 \times 10^{-7}$ cm$^3$s$^{-1}$. Again, this destruction mechanism is much larger than the Rb—Rb spin destruction cross section because the large size of clusters endows them with enormous collisional cross sections.

Nanocluster Non-Resonant Scattering—

And finally, nanoclusters likely cause broad-band scattering of incident laser light. This broad scattering cross section can be modeled as, $$\sigma_{cluster} = 1 \times 10^{-12} \text{ cm}^2 \qquad \text{Equation (4)}$$

roughly an order of magnitude larger than the peak scattering cross-section for the D1 resonance under the conditions in our cell.

Nanocluster Formation and Number Density—

With the physical effects of clusters included in the model, the remaining task is to postulate a means of scaling their number density. First, some baseline cluster density is likely to be created upon initial illumination by the laser. This is based on the observation that within seconds of illuminating an optical cell with laser light, a 5-10% drop in light transmission is observed, suggesting that clusters are created almost instantaneously upon laser irradiation.

Secondly, to account for the lack of observed polarization and production improvements under conditions of either increased laser intensity or improved laser narrowing, clusters likely form in proportion to the excited state population of Rb. This is given by $$[Rb_{5p+1/2}] = \tau \cdot [Rb] \cdot (1 - P_{Rb}) \qquad \text{Equation (5)}$$

where $\tau$ is the excited state lifetime of Rb. This is roughly 30 ns in the absence of collisional quenching, but its exact form is not critical for the noted purposes. Substituting for $P_{Rb}$ as defined by $$P_{Rb}(z) = \frac{\gamma_{opt}(z)}{\gamma_{opt}(z) + \Gamma_{sd}} \qquad \text{Equation (6)}$$

the cluster density can also be written as $$[Rb_{5p+1/2}] = \tau \cdot [Rb] \cdot \left(\frac{\gamma_{OP}\Gamma_{SD}}{\gamma_{OP} + \Gamma_{SD}}\right). \qquad \text{Equation (7)}$$

Thus, the density of clusters in an SEOP environment, $[Rb_n]$, then is simply the excited state number density scaled by a constant:

$$[Rb_n] = \Theta_{cluster} \cdot [Rb] \cdot \left(\frac{\gamma_{OP}\Gamma_{SD}}{\gamma_{OP} + \Gamma_{SD}}\right) \qquad \text{Equation (8)}$$

where $\Theta_{cluster}$ is defined to be the cluster activation rate, but for these purposes is $\Theta_{cluster} = 6.5 \times 10^{-8}$.

The overall scaling of cluster number density and the postulated cross sections are not fully independent. Thus, the same modeling effect can be achieved by increasing cluster density and decreasing the associated cross-sections, or vice versa. Thus, as a starting point for the model we have set the overall scale such that $[Rb_n]$, is roughly $\frac{1}{1000}^{th}$ the number density of atomic Rb, [Rb] at 100 degrees C., from which the value for the cluster activation rate of $\Theta_{cluster} = 6.5 \times 10^{-8}$ can be derived.

Model Versus Measurement when Rb Nanoclusters are Incorporated

Figure 7A:
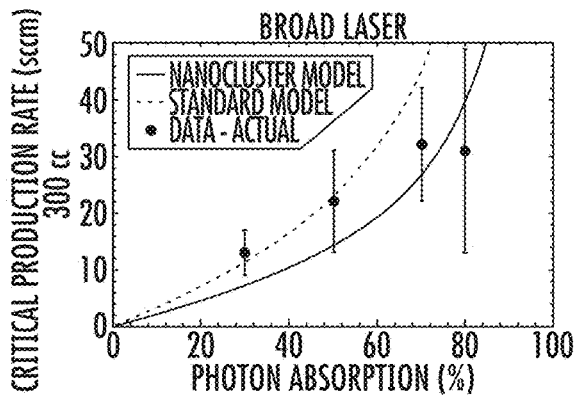
FIGS. 7A-7E are graphs of critical flow rate (sccm) versus photon absorption (%) for different size SEOP cells and broad laser (FIGS. 7A, 7C, 7E) and narrow (spectral width) laser (FIGS. 7B, 7D, 7F) corresponding to FIGS. 5A-5F but also including the model that includes relaxive effects of Rb clusters according to embodiments of the present invention.
Figure 7B:
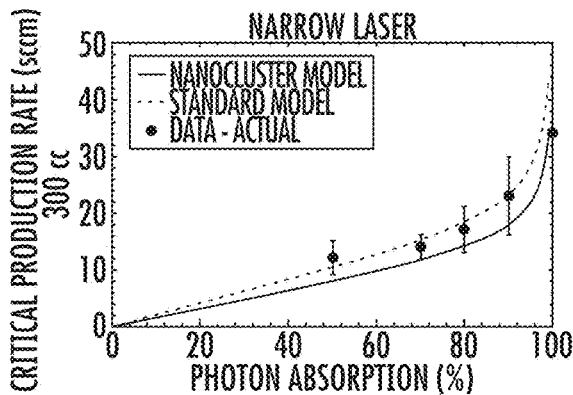
Figure 7C:
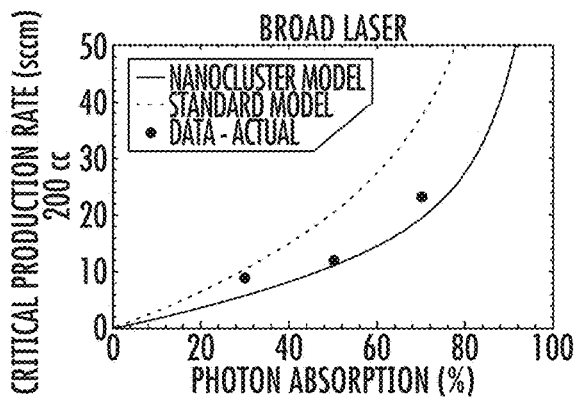
Figure 7D:
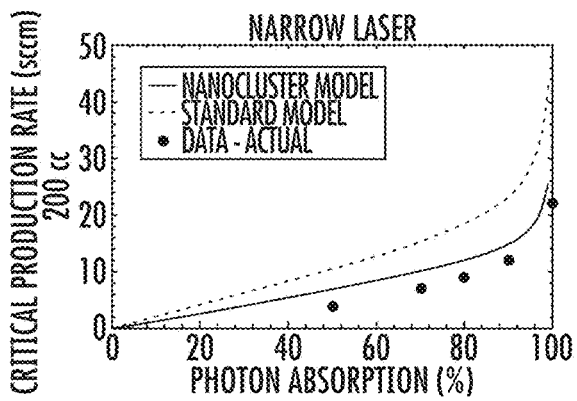
Figure 7E:
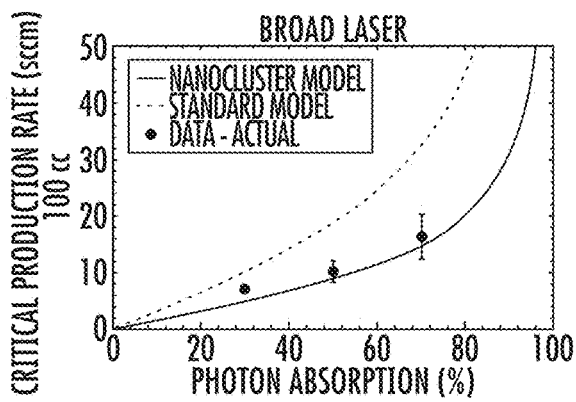
Figure 7F:
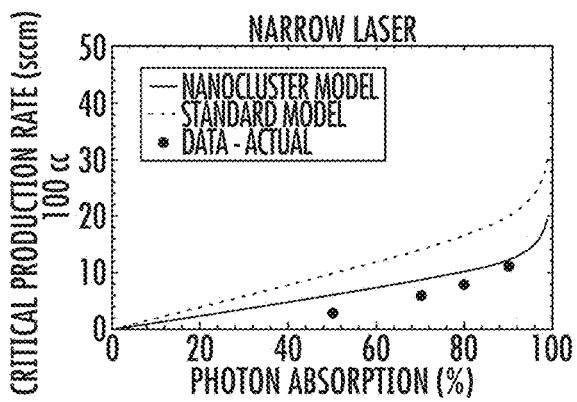

FIGS. 6A-6F show peak polarization data compared to the nanocluster model and FIGS. 7A-7F show polarized $^{129}$Xe production rates compared to the nanocluster model. Note that peak polarization now agrees exceptionally well across the entire range of absorptions for all six combinations of laser and optical cell geometry. Particularly, the low-absorption polarization, which so greatly underperforms the standard model, is now pulled into line by cluster-induced relaxation of the $^{129}$Xe. This mechanism of polarization suppression continues to grow towards higher absorption levels. The new model also appears to better predict the observed production rates (FIGS. 7A-7F), particularly for the narrowed laser (FIGS. 7B, 7D, 7F).

Note also that although reasonable agreement with the data could be achieved without hypothesizing an initial cluster density at low absorption, it was significantly improved by allowing the cells to exhibit somewhat individualized initial cluster densities. Using a steepest descent algorithm to optimize the model returned baseline nanocluster number densities of about $1.2 \times 10^9$ cm$^{-3}$, $3.9 \times 10^8$ cm$^{-3}$ and $1.4 \times 10^8$ cm$^{-3}$ for the 300 cc, 200 cc, and 100 cc cells, respectively. Interestingly, the initial number densities scale inversely with cell SN, and may suggest that such initial cluster generation is a more individualized aspect of a particular cell, perhaps determined by the distribution and accessibility of Rb pools across the cell surface.

Solving the NanoCluster Generation Problem

Embodiments of the invention propose various methods and devices to reduce, inhibit, prevent or suppress the generation of nanoclusters and/or to filter same from polarized gas to inhibit or reduce their influence on decay of polarization.

FIGS. 8A-8D illustrate an exemplary embodiment of a compact, flow-polarizer 10 with a pre-saturation chamber 200 that resides upstream of the optical cell 22. The term "pre-saturation" is used interchangeably with an abbreviated form "pre-sat".

The term "chamber" with respect to the pre-sat member and/or section of the gas flow path, refers to a region of a flow path that flowably supplies noble gas mixture into the optical pumping cell 22 with vaporized alkali metal. Thus, the pre-sat chamber 200 is configured to house alkali metal that is vaporized and introduced into a flowing noble gas mixture, then into the optical pumping cell 22. The pre-sat chamber 200 can be a detachable component or an integral part of the flow path. The pre-sat chamber 200 can be a tubular component (e.g., FIG. 8F), a curvilinear component or length (e.g., FIG. 10B) or have other shapes or configurations. The pre-sat chamber 200 can have an Area Ratio of surface area to cross-sectional area that is between 20 and 500, more typically between 20 and 200 as will be discussed below.

The flow path is such that there is a primary flow path in Fi and a primary flow path out Fo of the optical cell 22. The optical cell inlet Pe can be proximate one end of a bottom of the cell 22 and the exit Pex can be proximate a top opposing end of the cell 22. However, other flow path inlet and exit arrangements may be used, including axially aligned on sidewalls of ends of the polarizer cell (not shown).

As shown, in some embodiments, the exit end of the pre-saturation chamber 200$e_2$ can reside laterally closely spaced a distance Td from the centerline of the inlet port Pe, typically laterally spaced apart between about 0.25 inches to about 5 inches, such as about 0.5 inches, about 1 inch, about 1.5 inches, about 2 inches, about 2.5 inches, about 3 inches, about 3.5 inches, about 4 inches, about 4.5 inches and about 5 inches. The centerline (horizontally extending) of the chamber 200 and/or the exit or discharge end of the chamber 200$e_2$ can also reside at a height distance Hd that is below the optical pumping cell 22, typically within about 5 inches, and more typically within about 0.25 inches to the side of and about 1 inch below the inlet port of the optical pumping cell 22.

In some embodiments, the chamber 200 can be tubular and have a short length such as about between about 0.5 inches to about 2 inches, typically about 1.25 inches. The chamber 200 can have a feed line 202 that is orthogonal to the chamber 200. The opposing end portions of the chamber 200$e_1$, 200$e_2$ can be configured to retain the Rb or other target pre-saturation material. As shown, the opposing end portions of the chamber 200$e_1$, 200$e_2$ have a smaller diameter relative to the body of a major portion of the chamber 200, which can be formed by any suitable means, including, for example, crimping, indentations or a step in diameter or cross-sectional size of the tube or threaded segments. The change in size from smaller to larger and larger to smaller at the respective end portions of the chamber 200$e_1$, 200$e_2$ can be formed using internal devices or features such as internal collars, a change in wall thickness or other suitable restrictions.

FIG. 8B illustrates that the chamber 200 can include a wall with an internal surface 200$s$. The internal surface 200$s$ can comprise surface features 205 such as ridges, grooves, a patterned embossment of projections and recesses, or channels extending across at least a portion of a bottom of the chamber for a distance in an axially extending (flow) direction. As shown, the floor of the chamber comprises small ridges that rise off the floor a distance that is about 0.0001 inches to about 0.25 inches but do not occlude the flow path. The surface features 205 can be formed in any suitable manner, e.g., by forming the features directly on the internal surface of the chamber wall/floor and/or as a pattern in a coating on the floor, for example.

The optical cell 22 can include a top port 22$f$ for allowing access to the cell chamber, such as to add or remove chemicals, for example.

Optionally, the optical pumping cell 22 can include pairs of conduit legs 22$a$, 22$b$ that extend down into valves V, e.g., 20, 28 (which can be KONTES valves).

The optical pumping cell 22 can be relatively compact with a volume capacity of between about 100 cc to about 500 cc, such as about 100 cc, about 200 cc, about 300 cc, about 400 cc and about 500 cc. The optical pumping cell 22 can also have larger sizes, such as between about 500 cc-1000 cc, for example. The chamber 200 can have a length L that is between about 0.5 inches to 6 inches long, typically between about 1-3 inches, such as about 1.25" long. The chamber 200 can have a primary body segment with a cross-sectional height W (e.g., diameter, when tubular) that can be between about 0.25 inches to about 1 inch across, typically about 0.5".

The pre-sat chamber 200 can contain between about 0.25 g to about 5 grams of Rb, typically between about 0.5 to about 1 gram of Rb, (measured "new" as shipped by an OEM or supplier and/or prior to a first use). The pre-sat chamber 200 can comprise a wicking material 200$w$ that can distribute and/or absorb or soak-up the Rb. In some embodiments, this wicking material can comprise a silica wick 226 (FIG. 14A, for example) as will be discussed further below.

The internal cell wall(s) and outlet arm 22$b$ can comprise a nanocluster reducing coating such as, for example, siloxane.

The internal cell wall 22$w$ and/or outlet arm 22$b$ can comprise a nanocluster reducing material such as alkali-aluminosilicate glass. The nanocluster reducing material can comprise, for example, toughened alumino silicate glass such as Gorilla® glass from Corning, Inc. or sapphire glass grown from synthetic sapphire glass derived from a crystal of transparent sapphire.

As shown in FIGS. 1B and 10A, the polarizer 10 can comprise at least two different temperature controlled zones T1, T2, one (T1) for the pre-saturation chamber 200 and at least one other (T2) for the optical pumping cell 22 so that T1>T2. The volume of the pre-saturation chamber V1 is also less than the volume V2 of the optical pumping cell 22. In some embodiments, the pre-saturation chamber 200 in the T1 zone can be heated to temperatures between about 140 degrees C. and 300 degrees C., more typically between about 140 degrees Celsius to about 250 degrees Celsius, such as 140 degrees C., 150 degrees C., 160 degrees C., 170 degrees C., 180 degrees C., 190 degrees C., 200 degrees C., 210 degrees C., 220 degrees C., 230 degrees C., 240 degrees C. and 250 degrees C. The second temperature zone (T2) for the optical pumping cell 22 can be configured to have a temperature that is less than T1, typically with a temperature between about 70 degrees C. to about 200 degrees C., more typically between about 90 degrees C. to about 150 degrees C., such as about 95 degrees C., about 100 degrees C., about 110 degrees C., about 120 degrees C., about 140 degrees C. and about 150 degrees C., to maintain vapor pressure, in some embodiments. The zone T2 may also be configured to apply a temperature gradient of decreasing temperature from a greater temperature at a region proximate the inlet Pe to a lower temperature proximate the exit Pex, typically with a change that is about 10 degrees C., about 15 degrees C., about 20 degrees C., about 25 degrees C. or about 30 degrees C., for example.

The temperature zone T1 can comprise at least one (pre) heater 222 that can provide the desired heat to increase the temperature including conductive and/or convection heaters. The at least one heater 222 can be an electric heater. The at least one heater 222 can comprise one or more of an oven, infrared heaters, resistive heaters, ceramic heaters, heat lamps, heat guns, laser heaters, heat blankets (e.g., heat blanket that can be wrapped about the chamber 200 with at least one insulation layer, typically comprising Nomex®-fiberglass fibers, but other insulation materials may be used), pressurized hot fluid spray and the like. The at least one heater 222 can employ a plurality of different heater types. The at least one heater 222 can comprise an oven that encases or partially encases the chamber 200. The at least one heater 222 can comprise an internal heater in the chamber 200. The temperature zone T2 can also comprise at least one heater 122, typically comprising an oven. Each zone can be independently controlled to maintain a desired temperature or temperatures.

The polarizer 10 can be configured so that alkali metal is loaded only into the pre-saturation chamber 200 that is outside of the pumping laser exposure region of the cell 22.

In the embodiment shown in FIGS. 8A-8D, the front, left side (looking with respect to FIG. 8A) will typically be the front face of the cell into which the pumping laser light can shine/transmit. This embodiment may be particularly suitable for commercialization in that it is compact and relatively inexpensive compared to the large vertical optical cell systems discussed above.

As also shown in FIGS. 8A-8D, the flow legs 22a, 22b can be structurally attached for support with cross-brace 130 that may extend for at least a major length of the optical pumping cell 22 between the legs. The brace 130 may also be directly or indirectly attached to the back side of the cell 22.

Once the cell 22 is fabricated, the cavity of the main body can be acid etched to expose surface hydroxyl sites and then coated with a defined (robust) polymer comprising, for example, polydimethyl siloxanes. The cell 22 can then mounted on a vacuum manifold and the alkali metal A (e.g., Rb) can be "chased" into the pre-saturation chamber 200. The cell 22 can then be operated in a modified conventional high-volume polarizer 10 where heat is applied primarily to the pre-saturation chamber 200 and to a lesser (cooler degree) to the main cell body 22.

In some particular embodiments, in contrast to a normal optical cell 22 maintained at between 160-180 degrees C., the cell 22 can be held at a primary body temperature that is maintained at 150 C or less, such as between 100 C and 150 C, including, for example, about 100 degrees C., about 110 degrees C., about 120 degrees C., about 130 degrees C., about 140 degrees C., while Rb saturated vapor is picked up by the flowing gas stream in the pre-saturation chamber 200, which can be maintained at temperatures ranging from between about 150 to 250 degrees C., depending on the desired flow rates. In some particular embodiments, the pre-sat chamber 200 can be held at between 150 degrees C. to about 160 degrees C.

In some embodiments, the cell 22 can be a modified siloxinated cell.

Figure 8G:
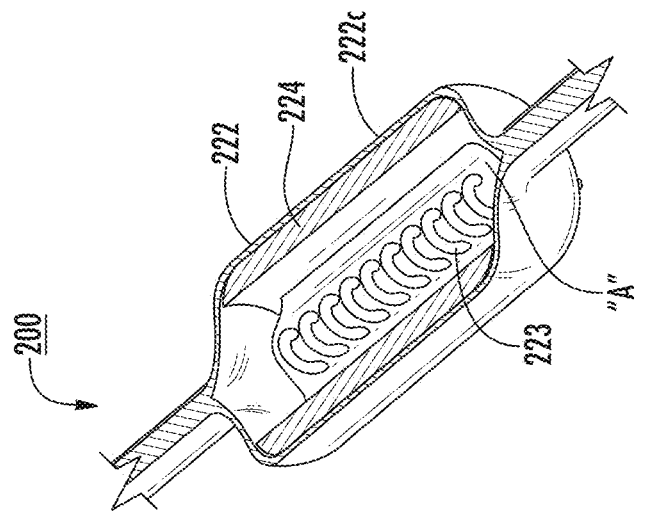
FIG. 8G is a partial cutaway view of the pre-saturation chamber shown in FIG. 8E that includes alkali metal therein according to embodiments of the present invention.
Figure 8F:
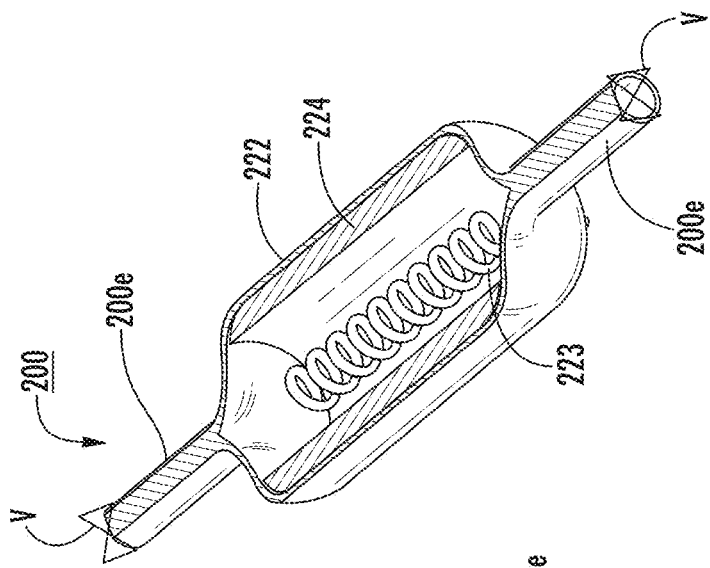
FIG. 8F is a partial cutaway top view of the pre-saturation chamber shown in FIG. 8E according to embodiments of the present invention.
Figure 8E:
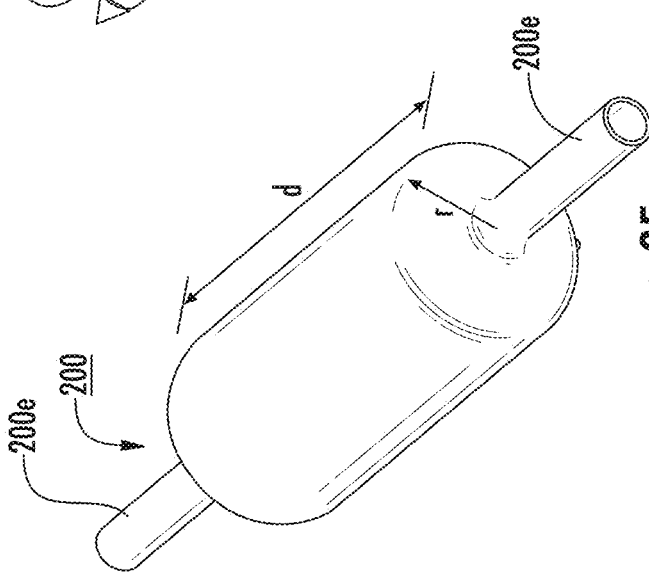
FIG. 8E is a top, perspective view of an exemplary pre-saturation ("pre-sat") chamber according to embodiments of the present invention.

FIGS. 8E, 8F and 8G illustrate an exemplary pre-saturation chamber 200.

The chamber 200 can be configured to be releasably attached/detached to the flow path of the polarizer system 10. As shown in FIGS. 8F and 8G, the pre-saturation chamber 200 can include an internal heating filament 223, an external casing 200c and insulating material 224. The external casing 200c can be metallic and may be thinner than the insulating material 224. For detachable configurations, the long cylindrical end portions 200e can be swaged or otherwise attached to valves "V" that releasably engage conduit or flow path tubing which may also include valves on each detach/attach coupling segment for the chamber 200. FIG. 8G illustrates that a suitable alkali material "A" (typically comprising rubidium) can be placed in the chamber 200, typically to at least partially cover the heating filament 223. The heating filament 223 can be coiled as shown and extend over at least a major portion of a length of the chamber 200. However, other internal heater configurations may be used with or without external heater configurations.

In the flowing $^{129}$Xe system 10, cluster production can be diminished if the incoming xenon mixture gas stream flows through the "pre-sat" chamber 200 that can warm the incoming gas and saturate that gas with Rb (and/or other alkali) vapor. In the past, a lengthy Rb saturator spiral has been used, described by Ruset as a ~6 m long, 2.5 cm diameter glass tube, with indentations positioned along the tube to hold the Rb puddles. The spiral is initially loaded with 25 g of Rb metal, mostly distributed on its lower half. This pre-saturation design is extremely large, cumbersome, and contains an extraordinary amount of Rb.

Based on the discovered nanocluster formation issue, embodiments of the invention can provide a compact pre-sat region that can dramatically reduce the amount of rubidium used. Effective heating and pre-saturation of the incoming gas stream can be largely controlled by the Area Ratio of the pre-saturator chamber 200. This Area Ratio ("AR") is defined as the ratio of the surface area to the cross sectional area of a respective pre-sat chamber 200. Thus, for cylindrical pre-sat chambers 200, Equation 9 provides this ratio but other chamber configurations will have other equations and mathematical ratios of surface area/cross-sectional area:

$$AR = \frac{2\pi r l}{\pi r^2}$$
$$= 2l/r$$

Equation (9)

By this calculation, known conventional pre-saturation devices have an area ratio of ~960. Conventional optical cells 22 (used without a pre-sat chamber) had an area ratio of ~10. The inventors have found that a more optimal area ratio AR for a pre-sat chamber 200 and/or pre-sat tubing length is between 20 and 500, such as 20, about 30, about 40, about 50, about 60, about 70, about 75, about 80, about 85, about 90, about 95, about 100, about 110, about 115, about 120, about 125, about 135, about 145, about 150, about 160, about 170, about 175, about 180, about 190, about 200, about 210, about 225, about 235, about 245, about 250, about 260, about 270, about 275, about 280, about 290, about 300, about 350, about 400, about 450 and about 500. In some embodiments, the AR is between 20 and 200. In particular embodiments, the AR is about 100. As is evident from the area ratio equation given above, a high area ratio can be achieved in more compact geometries by reducing the length and width, e.g., typically tubing radius, of the pre-sat chamber 200, proportionately.

As shown in FIG. 8E, for example, in some embodiments, a pre-saturation region 200 can be constructed using a tube length distance "d" of about 25 cm, with a diameter of about 1 cm, and a small amount of alkali metal, e.g., between about 0.25 grams to about 5 grams of Rb alkali metal, typically between about 0.75 to about 3 grams.

Moreover, the Rb may be effectively collected and distributed over a greater surface area inside a gas flow path by optionally incorporating a wick 226. The wick 226 can be a silica wick. The term "wick" refers to a typically flexible and/or hollow braided member that has a shape that forces or distributes alkali metal such as Rb to occupy a greater surface area of a pre-saturation region or chamber 200 relative to such a chamber or region used without such a wick. The (silica) wick 226 can be processed to that it is degassed, baked out under vacuum or otherwise treated to be free of moisture and surface contaminants that may prevent absorption of alkali metal (e.g., Rb) or contaminate alkali metal that does absorb. The wick 226 can optionally be substantially free of paramagnetic impurities although as the wick and Rb interact with the xenon mixture before the $^{129}$Xe has been polarized it is not required that the silica wick be free of paramagnetic material. The primary purpose of the wick 226 is to facilitate that the Rb occupies a greater surface area than it would as just a puddle, and that the wick also provides a way to help bulk Rb (or other alkali metal) stay localized in the pre-saturation chamber 200.

Figure 14A:
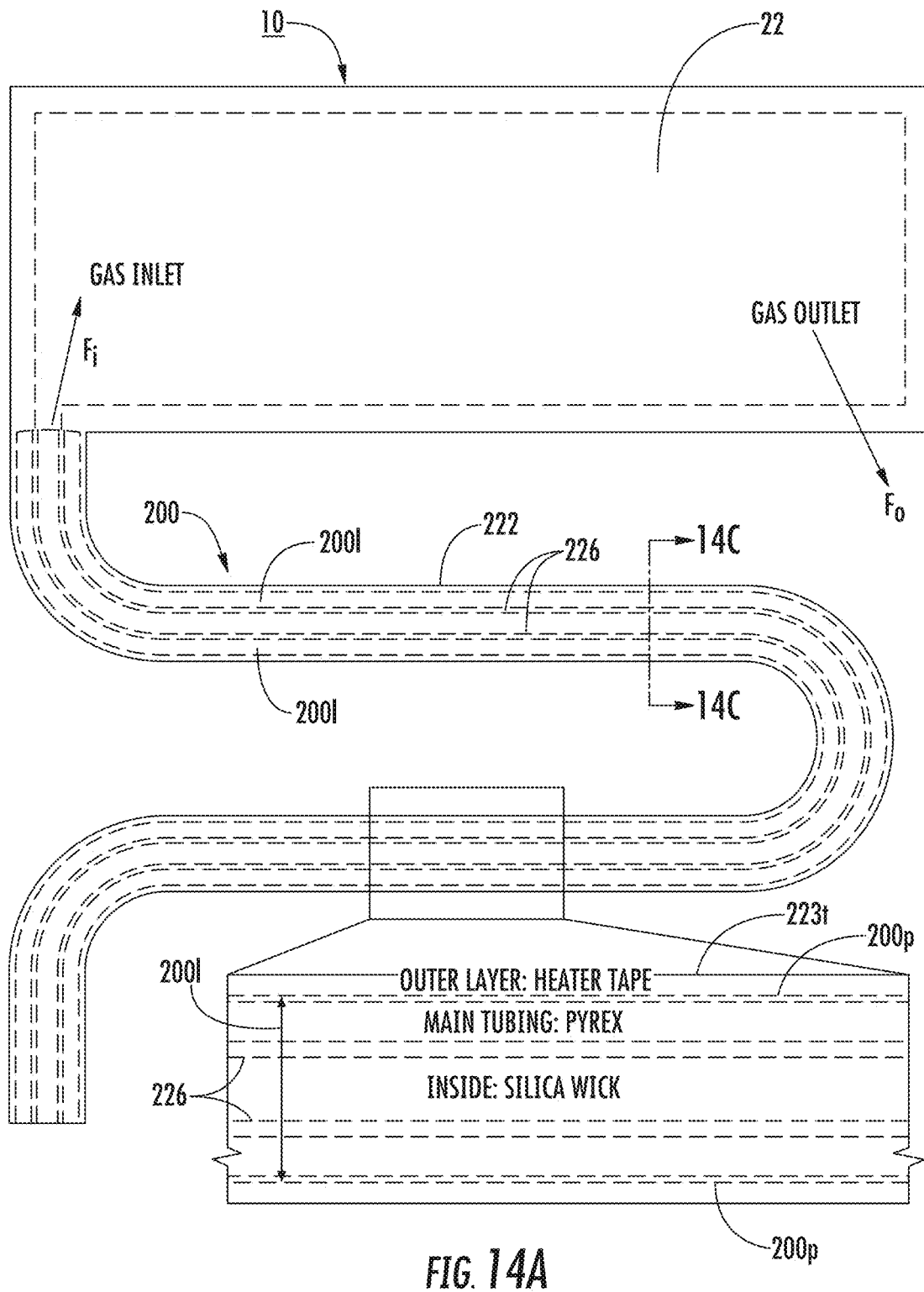
FIG. 14A is a schematic illustration of a portion of a hyperpolarizer residing upstream of an optical pumping cell with a wick for distributing alkali metal in a pre-saturation region and/or chamber according to embodiments of the present invention.
Figure 14B:
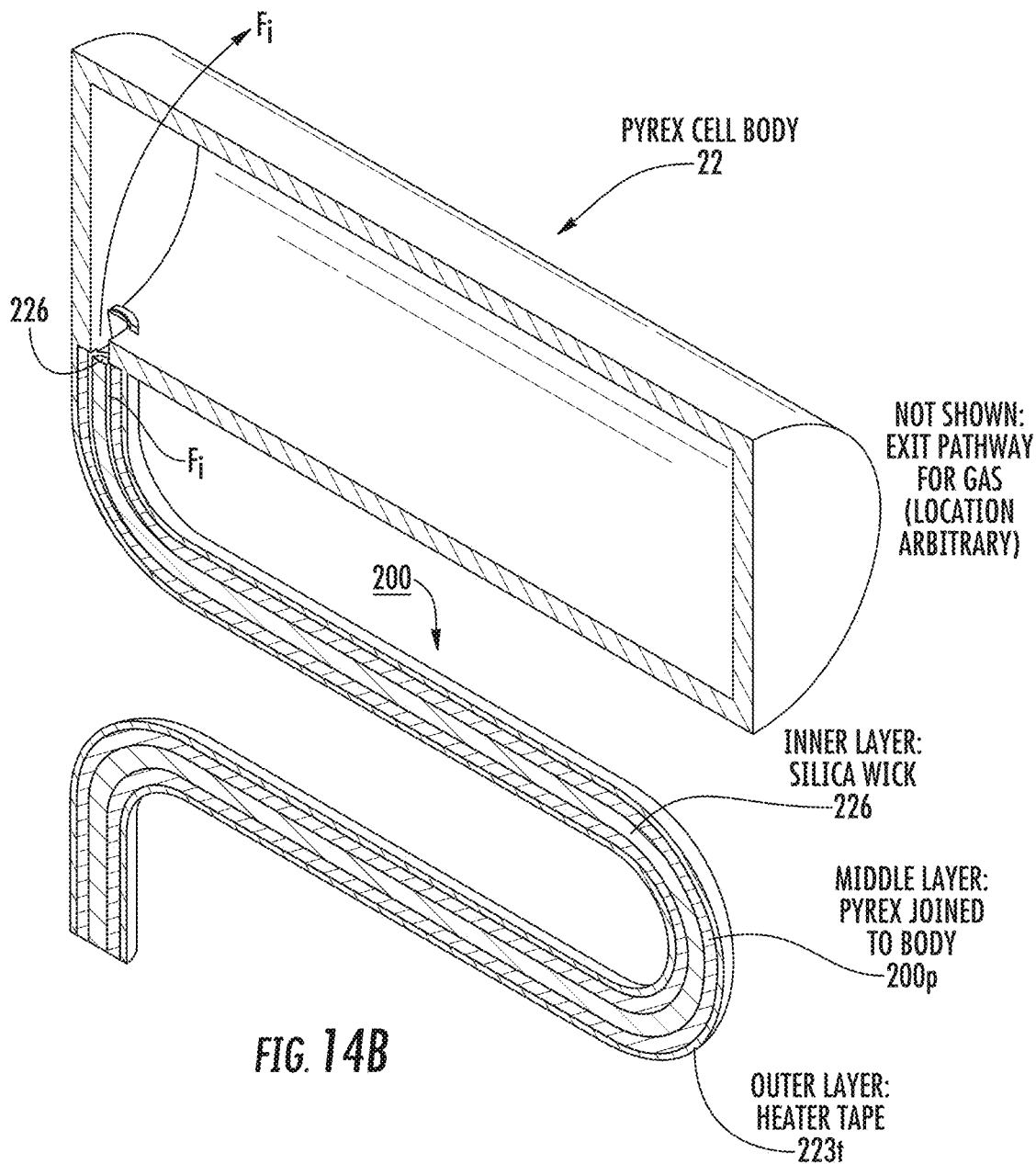
FIG. 14B is a partial section view of the portion of the hyperpolarizer shown in FIG. 14A according to some embodiments of the present invention.
Figure 14C:
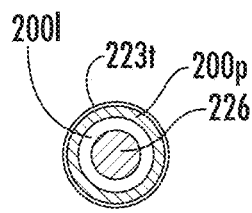
FIG. 14C is a lateral section view taken along line 14C-14C in FIG. 14A.

Referring to FIGS. 14A-14C the wick 226 can occupy a partial cross-sectional area of the gas mixture flow path of the pre-sat chamber or region 200, e.g., between about 20-50% of the lumen 200*l* of the primary body of the tubing or other pre-sat chamber 200*p*, typically about 50% of the lumen 200*l* of the pre-saturator chamber 200 (e.g., tube). The wick 226 may be oriented to extend in a longitudinal direction.

The wick 226 can be held medially and may be concentric with the inner wall of the primary body of the pre-sat chamber or region 200. The wick 226 may be discontinuous or continuous over a length of the pre-sat chamber 200. The wick 226 may be a flexible woven, braided or twisted material(s). The wick 226 may have laterally extending channels or apertures. The wick 226 may have a smooth, continuous outer surface or may have a rough and/or discontinuous outer surface. The outer surface of the wick 226 can include channels, notches or other shapes therein.

In some particular embodiments, an elongate (longitudinally oriented) silica or other suitable wick 226 having a cross-sectional size (e.g., diameter) between about 2-5 mm, such as about 3.5 mm in diameter, may be useful. The pre-sat region 200 and silica wick 226 can be curvilinear as shown in FIGS. 14A and 14B. The pre-sat region 200 can comprise a primary tube body 200*p* of a first material, such as PYREX, holding the silica wick 226 therein. While silica is a preferred alkali metal wick material, it is contemplated that other materials may be used with sufficient heat resistance or alkali tolerance and properties suitable for hyperpolarized gas systems. The wick 226 may also optionally include a surface coating material.

The pre-sat chamber 200 can include an external and/or integrated heater tape layer 223*t* as shown in FIGS. 14A-14C. FIGS. 8F and 8G illustrate an internal heater filament or coil 223. Combinations of the heater types or different heater types may be used for the pre-sat region 200.

Figure 9:
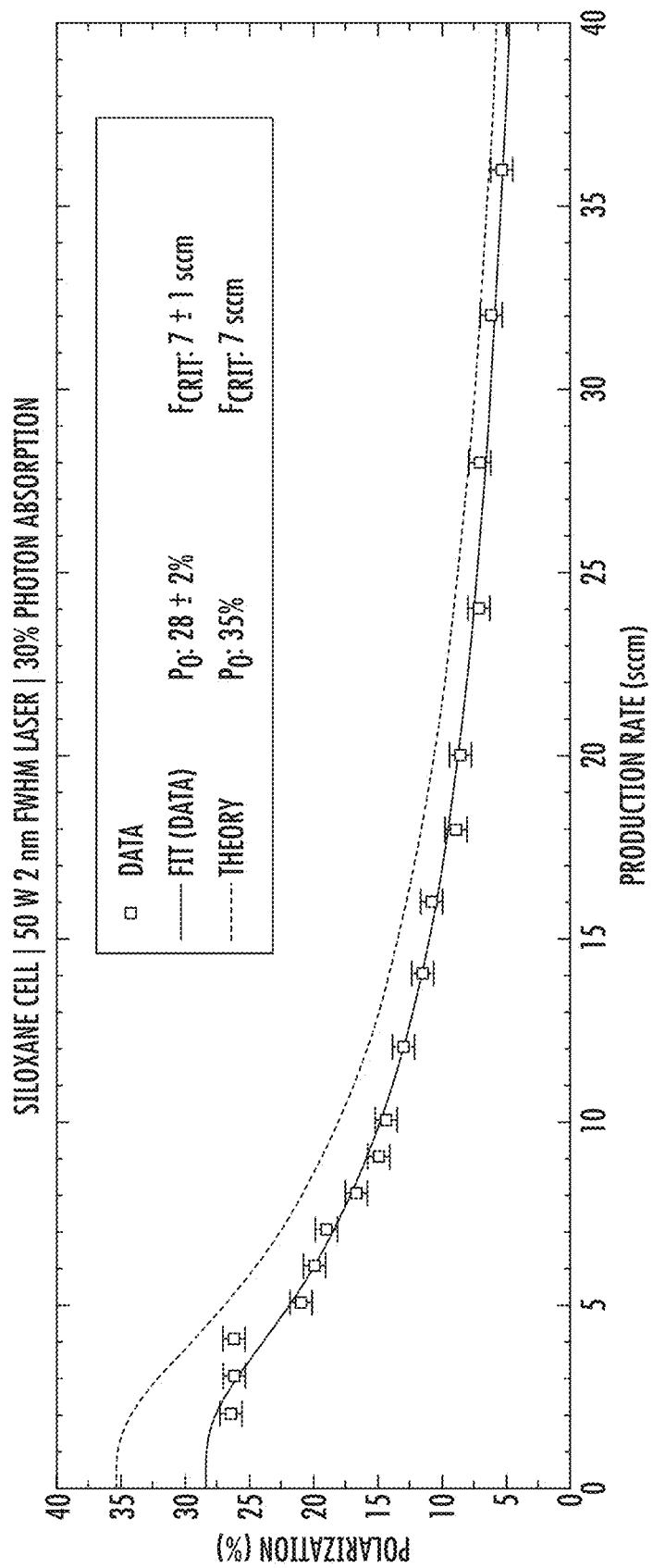
FIG. 9 is a graph of polarization (percentage) versus production rate (sccm) for a siliconized flow-through SEOP cell for a standard model-based prediction adjacent a flow curve with actual data fit to a curve illustrating the actual performance (siloxane cell, 50 W, 2 nm FWHM laser, 30% photon absorption) aligns with the predictive performance according to embodiments of the present invention.

FIG. 9 shows a polarization versus flow curve achieved with a pre-saturated siloxinated cell corresponding to that shown in FIGS. 8A-8D, pumped using 50 W of broadband laser light, and absorbing 30%. Under these conditions, the standard model of SEOP predicts a maximum polarization of 35% and a $^{129}$Xe production rate of 420 mL per hour. In fact, this is almost exactly what is observed, production rates are as predicted by theory, and at a polarization level very close to theory. Such close agreement between theory and experiment is unprecedented and provides strong evidence that nanoclusters have been suppressed or are non-existent.

Until now there has not been an understanding of the importance of nanocluster formation in optical pumping systems. In fact, it is believed that no one practicing in the hyperpolarized gas field is aware of the theoretical possibility of nanoclusters. The inventors have discovered the importance of nanoclusters in optical pumping systems and have invented methods and systems to suppress their formation and/or to filter them from polarized gas.

FIG. 10A illustrates the polarizer 10 with at least one pre-saturation chamber 200 and that can optionally include at least one nanocluster filter 225 residing between an exit port of the optical pumping cell 22 and the cold finger 30.

As shown, the nanocluster filter 225 can include a filter 225 that resides proximate the exit port Pe of the optical cell 22 upstream of the valve 28. Typically, the filter 225 resides outside the oven 122 of the optical pumping cell 22. The polarizer may alternatively or additionally comprise a filter 225 that is after the valve 28 and before the cold finger 30. A filter 225 can also or alternatively be positioned inside the cell 22, proximate the exit port Pex (not shown). The at least one filter 225 is configured so as to not cause decay of the polarization while trapping, attenuating, separating or attracting any nanoclusters in the flowing polarized gas.

The filter 225 can be configured as a tortuous path, e.g., a conduit that changes direction to trap the nanoclusters in elbows or dead spaces and/or shaped tubing with twists, turns or grooves.

The flow path Fo and/or leg 22*b* can be configured to break-up laminar flow patterns and/or generate turbulent polarized gas flow (promote nanocluster impact on a surface of the filter and/or adjacent flow path) upstream of the cold finger 30, typically between the exit port Pex and the top of the cold finger 30 so as to remove any nanoclusters from entering the cold finger.

The filter 225 can comprise silica fingers that extend across a width of the flow path, rather than in-line with the flow path.

The filter 225 can comprise or be configured as a cold trap that can be held at a temperature that is above the freezing point of xenon (163K) but configured to freeze out nanoclusters. In some embodiments, the cold-trap filter 225 can be held at a temperature between about 180K and about 250K, more typically between about 180K and 200K. The cold temperature can be generated using any suitable coolant or freezer, e.g., a dry-ice ethanol bath and/or one or more thermoelectric coolers. The cold trap configuration can also be applied as a gradient cold trap with increasingly cold temperatures over a length of the flow path between the exit from the optical cell and the cold finger.

The filter 225 can comprise a reusable or disposable cartridge with silica glass beads and/or sol gel glass beads, for example, residing in the gas flow path.

The filter 225 may comprise de-ionized, sterile water or moisture to react Rb nanoclusters into RbOH.

The filter 225 may comprise a polarized gas friendly one-way check valve. The filter 225 can be releasably held in the flow path and periodically replaced and/or cleansed to remove alkali metals.

The filter 225 can be configured to continuously neutralize any alkali metal in the gas such as by exposing the gas stream to ice.

The filter 225 can be configured to provide anode/cathode charge regions on the wall of the gas flow path or on a filter held in the gas flow path to attract highly charged nanoparticles/clusters (e.g., Rb and Rb nanoclusters) and remove them from the gas stream.

Figure 10B:
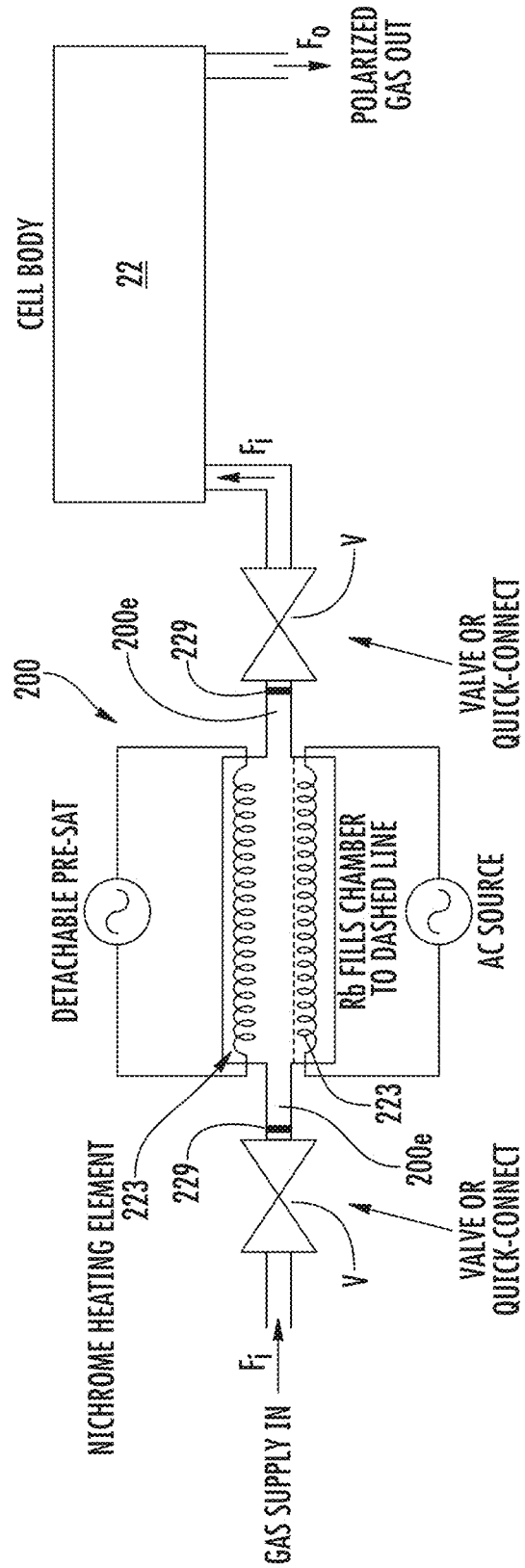
FIG. 10B is a schematic illustration of a detachable pre-saturation chamber according to embodiments of the present invention.

FIGS. 8F, 10B and 10C illustrate that the pre-sat chamber 200 can include or be configured as a releasably attachable (e.g., detachable) component that can be interchangeably replaced over time with "new" chambers 200 with a pre-filled amount of alkali metal. The replacement pre-saturation chambers 200, such as bulbs or tubular members, can be shipped separately from the optical cell 22. Such detachable pre-saturators 200 can be configured to hold alkali metal such as Rb, isolated from air to avoid being contaminated. Once installed, the pre-saturator 200 allows the gas mixture to flow through it and into the optical pumping cell 22 where optical pumping takes place. The detachable pre-sat member 200 can be configured to connect to the flow manifold 10*m* (FIGS. 1B, 10A, 16A) on each end 200*e* using valves, disconnects or other configurations. The valves V may be one-way valves. The output end 200*e* can connect to the optical pumping chamber 22 in a leak-tight manner. The sealable connections should also be able to withstand high temperatures of ~200° C. As schematically shown in FIG. 10B, the fluid path connections may include metal seals 239.

As schematically shown in FIG. 10C, a foil or other sealant 215 may be positioned over attachment segments of the replacement pre-sat member 200 to keep an air tight seal prior to assembly. The sealant 215 can be over an internal passage and/or an external passage or port. The flow path connection that connects to an end of the replacement pre-sat chamber 200 can be configured to puncture or otherwise remove the sealant upon assembly.

FIG. 10C also illustrates that one or both connections for the pre-sat chamber 200 may include a threaded port 216 that can threadably engage a mating attachment segment 218 and can allow distillation of Rb or other alkali metal, sealed later with the valve and/or quick disconnect to the gas flow manifold 10m. For example, to facilitate a "fill" of alkali metal into a pre-sat chamber 200, the threaded port 216 can be opened inside an enclosed "clean" space such as in a nitrogen glove box. The alkali metal can be warmed up so that it becomes liquid. The liquid alkali metal (e.g., Rb) can be drawn into a pipette, then pipetted into the pres-saturator 200. Once this has been done, the threaded port 216 can be closed with its valve and the pre-saturator unit 200 will now contain alkali metal (e.g., Rb) and be protected from the outside world. The pre-sat unit 200 can be removed from the enclosed space, e.g., nitrogen glove box, and shipped for assembly to a flow manifold 10m of the hyperpolarizer 10.

In some embodiments, the pre-sat chamber 200 can be releasably attached to a pressurized flow manifold 10m (FIGS. 1B, 10A, 16A) that resides upstream of the optical pumping cell 22 and maintains a gas flow path into the optical pumping cell 22 at a defined pressure. The detachable pre-saturation chamber 200 can be interchangeably, sealably attached to the pressurized flow manifold 10m to allow a first used pre-saturation chamber to be replaced with a factory-sealed pre-saturation chamber with alkali metal. The pre-sat chamber 200 can be threaded and/or include a valve or nozzle that can sealably attach to the pressurized gas flow path/manifold 10m for ease of replacement.

With respect to FIGS. 11, 12A and 12B, for example, it is contemplated that reduction or elimination of nano or microscopic pools of alkali metal on an internal surface of the optical cell 22i (e.g., typically a floor 22b) may reduce the generation of nanoclusters. It is also contemplated that reducing the surface area that such bulk and/or microscopic pools may occupy to reduce generation of the nanoclusters in response to laser irradiation of alkali metal proximate such pools. Thus, in some embodiments, the optical cell 22 can be configured to reduce the exposure to any bulk pools of alkali metal in the optical cell.

FIG. 11 illustrates that the internal surface 22s can include a floor 22b with a coating 22c, such as a coating comprising siloxane. FIG. 12A illustrates that the internal surface 22s can comprise grooves, ridges or a pattern of raised and recessed regions 22r to reduce the surface area on which the bulk alkali may accumulate in the cell 22. FIG. 12B is a section view of different exemplary shapes of the region(s) 22r. The regions 22r may be formed into the wall of the cell and/or into a coating 22c thereon. The regions 22r may be scored, etched, sprayed, painted, vapor deposited, pressed or stamped into the surface and/or coating thereon. The regions 22r may comprise fused silica projections.

Figure 13A:
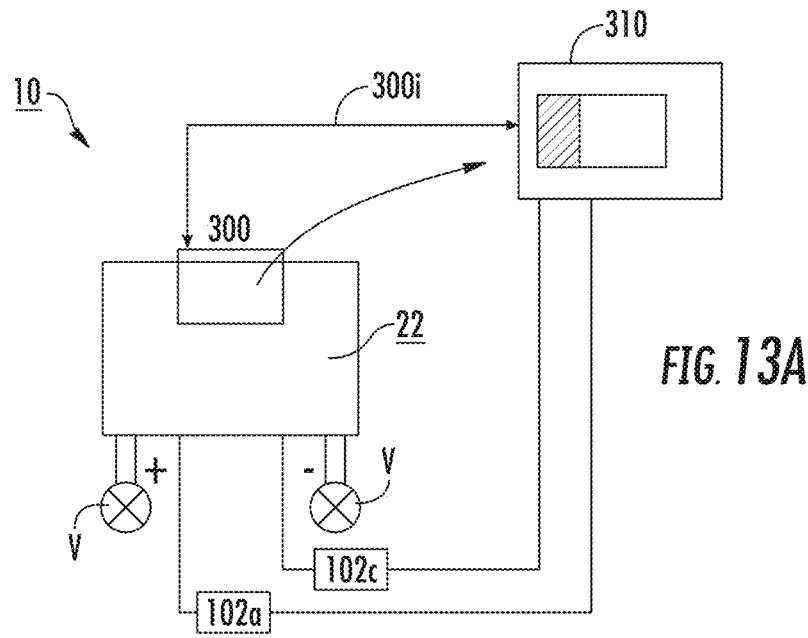
FIG. 13A is a schematic illustration of a hyperpolarizer with an alkali metal nanocluster detection and/or on-board production remediation system according to embodiments of the present invention.

FIG. 13A illustrates that the optical pumping cell 22 can have an electric charge, cathode and anode electrical inputs 102c, 102a that can be in communication with a control circuit 310 to generate electrical field across the optical pumping cell 22 to attract (highly) charged nanoparticles from the gas in the cell. It is contemplated that Rb (or other alkali metal) nanoclusters can be removed from an SEOP cell 22 and/or other part of the manifold of the polarizer using an electric field.

Optionally, a detector 300 may be in communication with the control circuit 310 to allow for automated adjustment of the electric field and/or to turn the field ON or OFF. Thus, FIG. 13A also illustrates that the polarizer 10 can include a monitoring input 300i to the control circuit 310 with a nanocluster signal detection device 300 comprising, for example, one or more of a laser, spectrometer or camera to monitor for the presence of nanoclusters.

Nanoclusters can be electrically charged, and thus they can be manipulated using appropriately strong electric fields, typically with input voltage between about 1 kV to about 100 kV, more typically about 10 kV, about 15 kV, about 20 kV, about 25 kV, about 30 kV, about 35 kV, about 40 kV, about 45 kV, or about 50 kV.

The voltage input/configuration can be configured to generate an electrical field in kV/cm across a primary portion of the optical pumping cell 22. Assuming, for example, an optical pumping cell 22 having about a 5 cm diameter, a 10 kV input would generate an electric field of 10 kV/5 cm or 2 kV/cm. It is contemplated that suitable electric fields for optical pumping cells 22 can be between about 2 kV/cm to about 20 kV/cm.

Figure 13B:
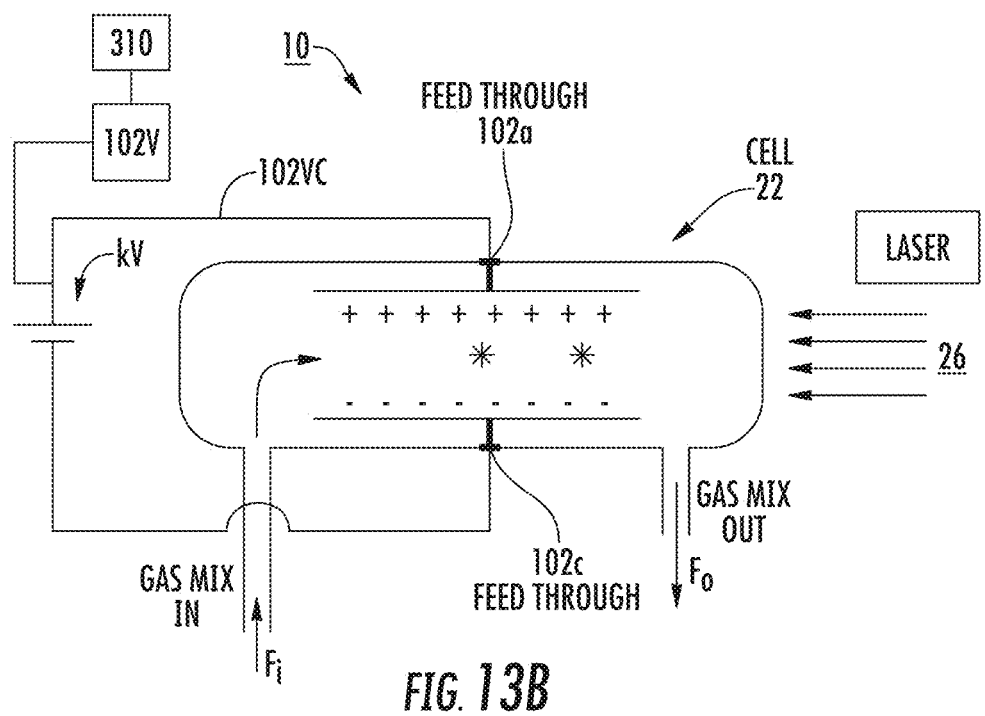
FIG. 13B is a schematic illustration of a hyperpolarizer with an alkali metal nanocluster on-board production remediation system according to embodiments of the present invention.

FIG. 13B illustrates that the polarizer 10 can include a voltage source 102v that can be in communication with a control circuit 310 and a voltage circuit 102vc that provides the electrical field charge with the anode/cathode electrical inputs 102a, 102c. While the anode input 102a is shown at the top and the cathode input 102c at the bottom of the cell 22, the reverse configuration may alternatively be used (as may side to side configurations). The circuit 102vc inputs 102a, 102c an include electrical feed-throughs to the cathode/anode members in the cell 22 to provide the desired (e.g., kV range) electrical field strength.

However, the electric field strength useful for this purpose can vary by design of the optical flow cell 22 and/or drag forces imposed by a buffer gas and other parameters including size and mass of a nanocluster, for example. Thus, to calculate a suitable electrical field, one may consider the size and mass of a nanocluster, the force applied by an electric field gradient, and the drag forces imposed by buffer gas mixtures.

Electric fields exert a force on charged particles of:

$$F = qE \quad \quad \text{Equation (10)}$$

The electric field strength can also be related to the more readily measured quantity in the laboratory—the voltage difference $\Delta V$ applied between anode and cathode. Thus, this mathematical relationship can be stated as:

$$E = \frac{\Delta V}{d} \quad \quad \text{Equation (11)}$$

where d is the spacing between the two. Thus, $$F = \frac{q\Delta V}{d} \quad \quad \text{Equation (12)}$$

To calculate a sufficiently large force, the most relevant obstacle that prevents charged clusters from being attracted to one of the electrodes can be evaluated. In some SEOP cell systems, this is the viscous drag force imparted on the small particle. Thus, it is likely desirable to use a voltage to create a force on clusters that greatly exceeds their viscous drag force.

$$\frac{q\Delta V}{d} \gg F_{drag} \quad \text{Equation (13)}$$

The viscous drag force on a small sphere moving through a viscous fluid is given by;

$$F_d = 6\pi\mu r v \quad \text{Equation (14)}$$

where $F_d$ is the drag force, $\mu$ is the dynamic viscosity in kg m$^{-1}$ s$^{-1}$, r is the cluster radius in m, and v is the cluster velocity. By applying the electric field, a velocity can be maintained towards the grids that can greatly exceed the natural drift velocity of particles in the flowing gas stream in the cell 22. That velocity is on the order of centimeters per second and is set by the volume of the cell. Thus, a drift velocity of 2 cm/s can be used by way of example. The dynamic viscosity of helium is $1.86 \times 10^{-5}$ $(T/T_0)^{0.7}$ kg·m$^{-1}$ s$^{-1}$ (Petersen '70), which varies little with pressure and is similar for nitrogen. Thus, this provides a reasonable estimate. The estimate for a largest anticipated nanocluster size of 600 nm can be used. Thus, this can calculate the viscous drag force to be $$\mu_{He} @ 150° C. \quad V \quad R$$
$$2.5 \times 10^{-5} \text{ kg m}^{-1}\text{s}^{-1} \quad 0.02 \text{ m s}^{-1} \quad 3 \times 10^{-7} \text{ m}$$

$$F_d = 6\pi(2.5 \times 10^{-5} \text{ kg/m·s})(.02 \text{ m/s})(3 \times 10^{-7} \text{ m}) \quad \text{Equation (15)}$$
$$F_d = 1.5 \times 10^{-13} \text{N}$$

The voltage can be calculated by the following:

$$\frac{q\Delta V}{d} \gg 1.5 \times 10^{-13} \text{N} \quad \text{Equation (16A)}$$

Assuming that nanoclusters have a single unit of charge of about $1.6 \times 10^{-19}$ C, and the field is applied over d=10 cm, a suitable voltage of:

$$\Delta V \gg \frac{1.5 \times 10^{-13} \text{N} \cdot 0.1 \text{ m}}{1.6 \times 10^{-19} C} \quad \text{Equation (16B)}$$

or approximately 100 kV. This may be an upper limit estimate as nanoclusters are likely smaller in radius than the estimate used in this example, and may have more units of charge. Thus, 10 kV is likely to be sufficient.

FIG. 15A illustrates that the cell 22 can be rotated while aligned with the laser to inhibit bulk microscopic alkali pools from forming.

FIG. 15B illustrates that the cell and/or floor thereof can be vibrated to inhibit bulk alkali pools from forming. The vibration can be a physical vibration of the cell itself or can be carried out by applying an electrical charge to a coating to cause an internal material, e.g., a coating, to vibrate.

FIG. 16A illustrates that the polarizer 10 can include a control circuit 310 that monitors the optical cell 22 for detection of nanoclusters. The control circuit 310 can include a detector 300 that is in optical communication with the cell 22 to monitor for a defined nanocluster signature and/or associated signal 300s. The control circuit 310 can be configured to generate an audible and/or visual alert if nanoclusters are detected. The detector 300 can comprise a filter to suppress the laser light and a video camera for recording images of the interior of the cell 22 during polarization operation to identify "clouds" of activity associated with nanoclusters. The detector 300 can comprise a spectrometer that can detect the nanoclusters in the presence of irradiated (laser) light. The control circuit 310 can carry out the detecting using fluorescence spectroscopy. It is contemplated that fluorescent peaks from nanoclusters will be in the range of between about 400-800 nm. For the camera system, the detecting can be carried out using imaging with an IR (infrared) camera to observe plumes associated with nanoclusters. The control circuit 310 can generate a nanocluster alert when nanoclusters are detected to allow adjustment to the polarizer to optimize or adjust polarization production parameters (alleviate or reduce decay from nanoclusters). The control circuit 310 can be configured to adjust the temperature of the heater 122 of the polarizer and/or turn the optical pumping laser 26 ON or OFF to reduce the nanocluster formation.

In some embodiments, the detecting may alternatively be carried out electronically using a probe beam B (FIGS. 17A, 17B) that can be attenuated by the presence of nanoclusters but not by atomic rubidium as will be discussed further below.

The optical pumping cell 22 can be cleansed or replaced if nanocluster generation is detected and/or at defined time frames.

FIG. 16B illustrates that the polarizer 10 can be configured to have a laser source L (26) with an excitation input light cycle for optical spin polarization/pumping that is briefly turned OFF or occluded from entering the optical pumping cell 22, e.g., to have an interleaved ON and OFF operational laser cycle, "Lcycle." Nanoclusters can be generated by laser irradiation thus a suitably configured operational cycle may inhibit, reduce or prevent the formation of nanoclusters. The OFF period can be relatively short, e.g., between about 0.1 second to about 1 second between longer ON periods, which may be between about 1 second to about 10 minutes, typically between about 10 seconds to about 1 minute. For example, ON for 10 seconds, OFF for 1 second. The ON and OFF periods may change over time, or may be altered in response to detection of nanoclusters in the cell or exiting the cell 22, for example.

FIGS. 17A-17E illustrate a polarizer 10 with a laser-based nanocluster detector system according to some embodiments of the present invention. Detecting and/or measuring attenuation of off-resonant probe light can provide a real-time diagnostic of nanocluster generation. The term "off-resonance" with respect to the probe laser wavelength that is at least 5 nm away from ground state atomic absorption resonances of an alkali metal used in the optical pumping cell 22 for spin-exchange optical pumping, and is preferred to be at least 10 nm away from ground state atomic absorption resonances of an alkali metal used in the cell for spin-exchange optical pumping.

The detection system can includes at least one nanocluster-probe laser 500 with a defined wavelength and a detector 505 such as a photodiode 505d. The photodiode or other detector 505 can provide a voltage or other output that can be read by a scope and/or control circuit 310. Rubidium has ground state atomic absorption resonances around 359 nm, and 421 nm. The off-resonance wavelength can be such that the nanocluster probe laser wavelength is at least 10 nm away from those. Cesium has ground state atomic absorption at around 388 nm and 460 nm, so where Cs is used, the off-resonance wavelength should be selected to be about 10 nm apart from either of these.

The laser 500 can be arranged to project the laser light (probe) beam B across the cell 22 into the photodiode 505d or other cooperating, typically aligned, detector 505. Thus, the laser 500 can reside adjacent a front or back long side 22f, 22r of the optical pumping cell 22 and the detector 505 can reside on an opposing long side of the cell 22. Detected visible wavelength light B leaving the cell 22 will be attenuated $B_A$ and/or less intense when nanoclusters NC are present as shown in FIG. 17C.

The laser 500 may be configured to project into the cell 22 in a direction that is orthogonal to the primary gas flow and/or axis A-A of the cell 22. While FIGS. 17A-17C show the beam B projected across the cell 22 at a vertical centerline location, the beam B can be projected above or below this position.

Figure 17A:
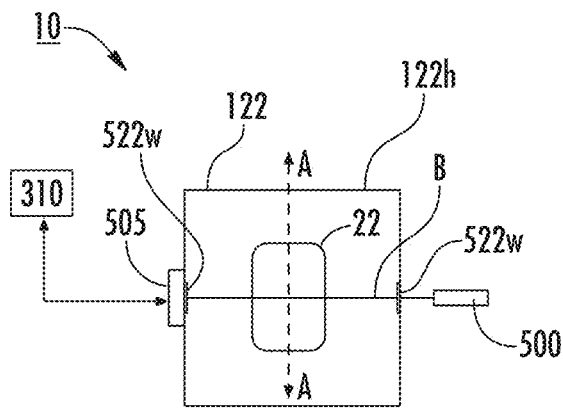
FIG. 17A is a schematic top view of an optical pumping cell of a polarizer with a light source (laser)-based nanocluster detection system according to embodiments of the present invention.
Figure 17B:
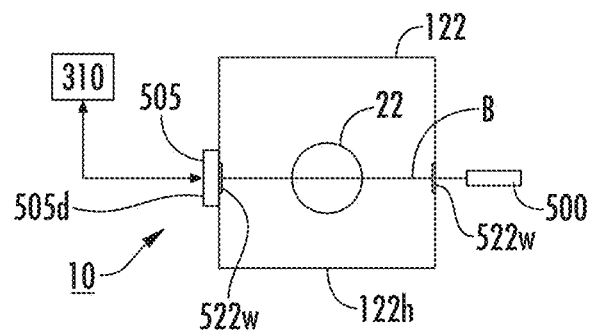
FIG. 17B is a schematic side view of the optical pumping cell with the nanocluster detection system shown in FIG. 17A.
Figure 17C:
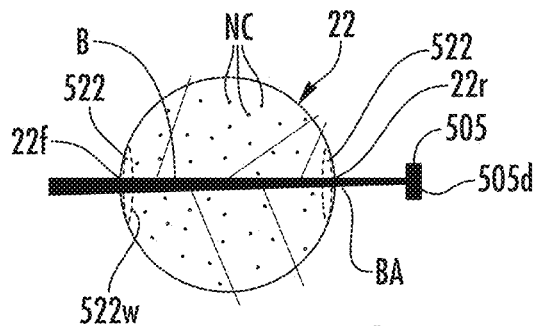
FIG. 17C is a cross-sectional view of the optical pumping cell illustrating a projected laser beam across the cell into a photodiode according to embodiments of the present invention.

The orientation of the laser to detector 500, 505 may be in the reverse shown in FIGS. 17A and 17B and/or may include or be top to bottom or bottom to top, but this is less preferred. More than one laser probe 500 and detector 505 pair may be used, with different wavelengths or the same wavelength (not shown). The laser 500 and corresponding detector 505 can each reside outside the oven wall 122 as shown. A window or transparent or translucent segment 122w in the oven housing 122h can allow optical access for the light beam B.

Figure 17D:
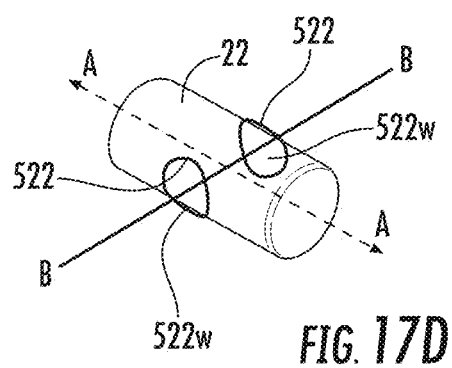
FIG. 17D is a schematic side perspective view of an optical pumping cell with a probe beam according to embodiments of the present invention.

As shown in FIG. 17D, the optical pumping cell may include heating elements 522 positioned proximate the probe beam B ingress and egress regions. The heating elements 522 provide a clear path or window 522w for the probe beam B. While shown as circular segments, any desired configuration may be used. These "regional" heater segments can be two rings of heater tape on the walls of the cell 22 that the laser probe beam B passes through. These probe windows 522w can be hot enough to prevent Rb from condensing there. If Rb droplets were to condense there, they would attenuate the probe beam B, even if there were no nanoclusters. The other heater is more global relative to the cell 22, it heats up the cell 22 for optical pumping, e.g., oven 122. The "global" heat is to generate enough Rb vapor pressure to start the optical pumping (which may also contribute to nanocluster formation).

The heating elements 522 can be above the melting point of the alkali metal, e.g., 40 degrees C. for Rb. The heating elements 522 can optionally make the associated regions of the cell 22 hotter than adjacent regions from oven temperature providing optically transmissive windows 522w. While 100 degrees C. may be sufficient, it is preferred that the heating elements 522 heat the cell thereat to between 150 degrees C. and 300 degrees C., typically above 150 C, more typically between 160 degrees C. and about 200 degrees C.

While verification of nanoclusters by electron microscopy is believed to be an important step forward, the implementation of a non-destructive in-situ diagnostic or detection circuit to identify the presence of nanoclusters may be of particular interest for production systems. One approach is to exploit the fact that if ~200 nm clusters are present in the vapor phase, they should attenuate non-resonant light via Mie scattering. Hence, they may be detectable in situ using a simple non-resonant probe beam. Once such diagnostics are available it should become feasible to develop and test strategies that mitigate cluster formation. If such formation can be prevented it should become possible to return full "scalability" to hyperpolarized $^{129}$Xe production, by fruitfully deploying increasingly higher laser powers.

In some embodiments, in order to develop this diagnostic or detection system, a 450 nm blue emitting diode laser can be used. This wavelength may be suitable as it was far removed from the principal 780 nm and 795 nm resonances of Rb. Hence, a cell containing only pure atomic Rb will not scatter 450 nm light. However, this situation changes dramatically if clusters are present in the gas-phase that have a size on the same order as the wavelength of the probe light. In this case, it is expected that the particles will scatter the probe light by a mechanism known as Mie scattering. Very simply, the intensity of the probe beam I after passing through the medium is given by Beer's Law:

$$I = I_0 e^{-[Rb_n]\sigma z} \qquad \text{Equation (17)}$$

where $I_0$ is the initial intensity, $[Rb_n]$ is the cluster number density, $\sigma$ is the scattering cross section of the particles, and z is the distance through the medium. Because z is known from the experimental set-up, once could in principle calculate the number density of clusters, if their scattering cross section is known. The scattering cross section will depend on particle size and can require careful simulations. However, considerable insight can be gained in from evaluating the limiting case of Rayleigh scattering, which is appropriate when the particle diameter a is much less than the wavelength of the light. In such a case, the scattering cross section is simply given by:

$$\sigma = \frac{128\pi^5 a^6}{3\lambda^4}\left[\frac{n^2-1}{n^2+2}\right] \qquad \text{Equation (18)}$$

where $\lambda$ is the wavelength of the light, and n is the ratio of the particle index of refraction to the medium (vacuum). This can be taken to be roughly 1.5 for purposes of calculation. For a 20-nm particle, scattering 450-nm light, the cross section would be $6 \times 10^{-14}$ cm$^2$. By contrast, if a much longer wavelength probe beam of say, 900 nm, is used, the cross section is reduced to $3.7 \times 10^{-15}$ cm$^2$ by virtue of the strong wavelength dependence of Rayleigh scattering.

Hence, a probe laser 500 with the shortest possible wavelength that can still penetrate pyrex glass (or other optical pumping cell material) readily and is not near any known alkali metal absorption resonance is preferred. Thus, the laser 500 can be any suitable laser, but is preferably selected based on a shortest possible wavelength that still readily penetrates Pyrex glass. Pyrex starts to absorb light below about 350 nm, so it is preferred that the wavelength be between 350 nm and 500 nm. The shortest wavelength is desired because the scattering cross-section for clusters scales as 1/lambda^4, which is very strong wavelength dependence. If the wavelength is doubled, the scattering cross section is reduced by 2^4=16, so it is much less sensitive. Finally, the off-resonance wavelength should be such that it is not associated with any known absorption resonances for Rubidium (or the alkali metal of choice, which could be Cesium as well). Rubidium has ground state atomic absorption resonances around 359 nm, and 421 nm. As discussed above, it is contemplated that the nanocluster probe laser wavelength should be at least 10 nm away from those (e.g., 349 nm or 431 nm or greater). Cesium has ground state atomic absorption at around 388 nm and 460 nm, so where Cs is used, the wavelength should be selected to be about 10 nm apart (e.g., 350 nm-378 nm, 398-450 nm, 470 nm and above) for Cs to be separated from either of these.

While the optical pumping laser is directed collinearly to the long axis of the cylindrical cell, the probe laser is directed transverse to it. If the optical pumping process creates a cloud of clusters, the probe laser will be attenuated. To ensure that the diagnostic is not impacted by systematic errors caused by condensation of Rb metal on the walls of the optical cell 22 through which the probe beam B must pass, heating can be applied to those areas to create optically transmissive windows on either side. In operation, the optical pumping laser can be turned ON and the window regions 522w can be heated, typically to about 200° C. Then, to stop nanocluster formation, the optical pumping cell laser 26 can be turned OFF (as well as the associated heat).

Figure 17E:
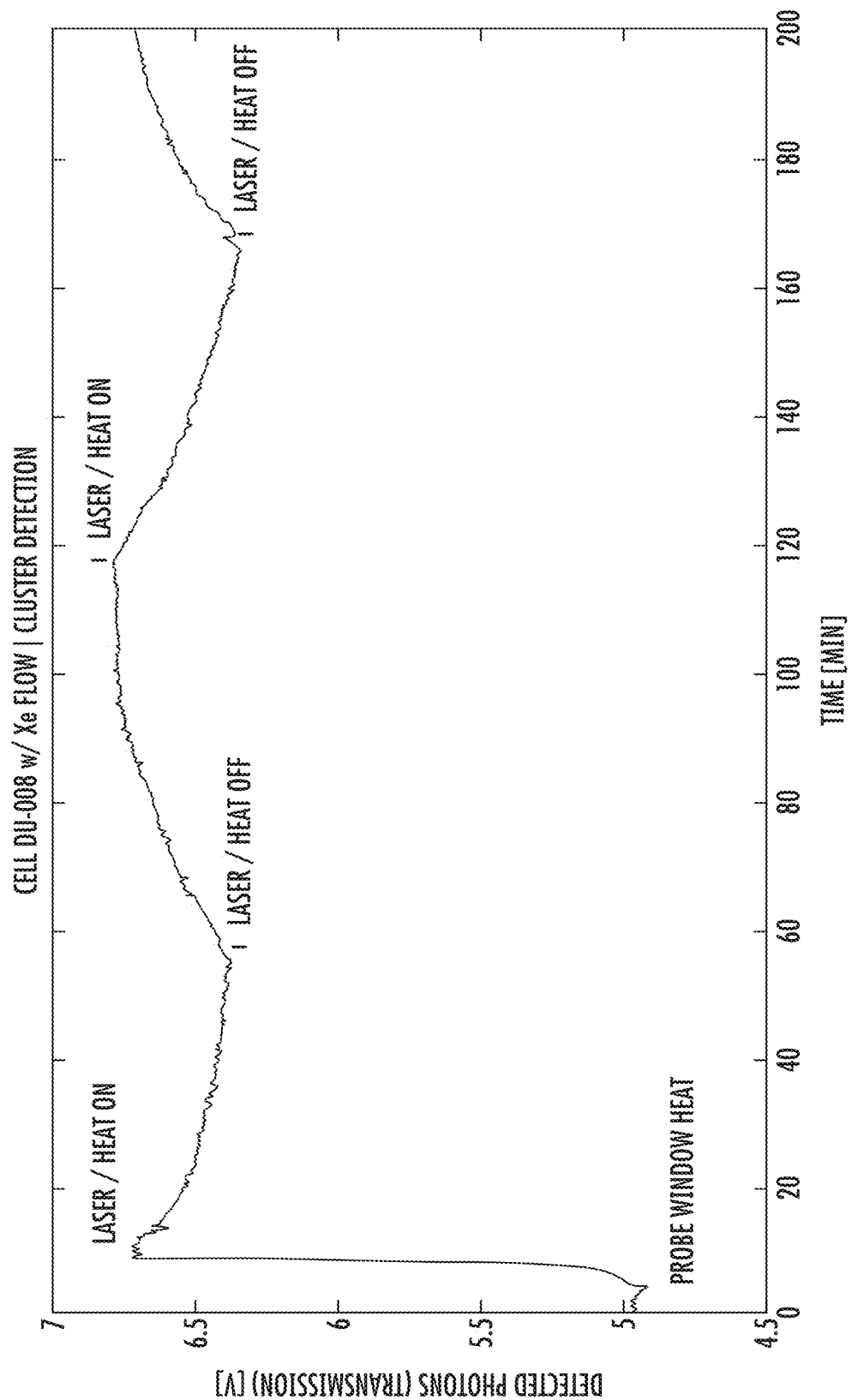
FIG. 17E is a graph of detected photons (V) over time based with attenuation associated with heat from the optical pumping cell laser being ON or OFF to reduce cluster formation according to embodiments of the present invention.

Preliminary results of such a probe experiment are shown in FIG. 17E. It shows that upon turning on the heat from heat elements 522 to the probe window 522w, the 450-nm probe beam B with light intensity I initially increases as Rb film on the inside surface of the cell evaporates from these regions. Subsequently, the optical pumping laser 26 and associated heat are turned ON. A corresponding attenuation of the 450-nm light over the course of roughly 40 min occurs as heating takes place. Immediately upon turning OFF the pumping laser 26 and associated heat, blue light transmission of the laser probe beam B is again increased back to baseline. The experiment is repeated a second time with similar results. It is interesting to note that during this time, the relative intensity I of the probe beam B drops to approximately 94% of its initial value. In the experimental cell 22, the probe beam B traverses a distance of approximately 5 cm across the cell 22. Hence, one can solve Beer's law to determine that $$[Rb_n]\sigma = \frac{-\ln(0.94)}{5 \text{ cm}}$$ Equation (19)
$$= 0.01 \text{ cm}^{-1}$$

This allows estimation of cluster number density by making assumptions about the scattering cross section, $\sigma$. In this example, the scattering cross-section derived from the spin exchange modeling work of $\sigma=1\times10^{-12}$ cm$^2$, which under Rayleigh assumptions for 795-nm light corresponds to a particle size of roughly 47 nm. Using this cross section, we can determine that in the probe experiment described above, a cluster density of $[Rb_n]\approx10^{10}$ cm$^{-3}$ was in the cell 22.

Once nanoclusters are suppressed, the performance of a polarizer is believed to be greatly improved. Moreover, the suppression of nanoclusters now allows scaling-up laser power to increase production rates in a systematic and well-understood manner. Without suppressing nanoclusters, adding more laser power only adds cost, but does not reliably increase system performance. Thus, the nanocluster recognition and control can allow for more efficient use of lasers and higher power lasers for the cell 22. For example, it is contemplated that optical pumping cells 22 of between 300 cubic centimeters to about 1 liter should be able to produce 25 ml of polarized xenon per Watt of light absorbed per hour. If 100 W are absorbed, the polarizer should produce 2.5 liters of hyperpolarized xenon per hour. If 200 W are absorbed, it is expected that the polarizer can produce 5.0 liters, etc.

It is contemplated that a polarizer 10 can employ a 200 W optical pumping laser 26, spectrally narrowed with a width <0.25 nm. This width is believed to be a preferred operation for current laser manufacturing with narrowed output. However, over time, it is contemplated that the optical pumping laser may be increased to apply 400-500 W to reach a target 10 liter/hr production mark.

Embodiments of the invention may be particularly suitable for optical pumping cells 22 with sizes between 300 cc (cubic centimeters) and 1000 cc. To inhibit nanocluster formation, embodiments of the invention may limit the amount of power deposited in a given cell volume. It is believed that about 60 W/300 cc can be deposited into a cell without realizing nanocluster formation; thus, the polarizer 10 can be configured to deposit 5 cc/Watt in the optical pumping cell 22. Thus, if it is a target to absorb 100 W, a 500 cc cell can be used; to absorb 200 W, a 1 liter cell can be used.

Furthermore, it is now possible to increase the efficiency of hyperpolarizers by employing other alkali metals like Cs, which had been abandoned because they paradoxically did not work well despite theoretical calculations to the contrary. And finally, the knowledge of nanoclusters, and a robust method to prevent their formation now allows engineering and manufacturing of $^{129}$Xe hyperpolarizers to become truly a science and not an art. Hence, this should permit rational miniaturization of polarizers, rather than (random) enlargement.

While not being limited to any particular polarizer configuration, embodiments of the invention are particularly suitable for high-volume, flow polarizer systems. These systems can take on various forms and use various components as is known to those of skill in the art. To form a more complete patent application, an example of a polarizer is shown in FIG. 1B. To be clear, different components and arrangements may be used and not all components shown are required. Thus, referring again to FIG. 1B, as is known by those of skill in the art, this figure illustrates an example of a modified compact flow-through high volume polarizer which is configured to (continually over a production run) produce and accumulate spin-polarized noble gases, i.e., the flow of gas through the unit is substantially continuous. As shown, the unit 10 includes a noble gas ($^{129}$Xe) supply 12 and a supply regulator 14. A purifier 16 can be positioned in the line to remove impurities such as water vapor from the system as will be discussed further below. The hyperpolarizer unit 10 can also include a flow meter 18 and an inlet valve 20 positioned upstream of the polarizer cell 22, typically also upstream of the pre-saturation chamber 200. An optic light source such as a laser 26 (either narrow or broad band, typically a diode laser array) is directed into the polarizer cell 22 through various focusing and light distributing means 24, such as lenses, mirrors, and the like. The light source is circularly polarized to optically pump the alkali metals in the cell 22. An additional valve 28 can be positioned downstream of the polarizer cell 22.

Next in line, as shown in FIG. 1B, is a cold finger or accumulator 30. The accumulator 30 can be connected to the hyperpolarizer unit 10 by a pair of releasable mechanisms such as threaded members or quick disconnects 31, 32. This allows the accumulator to be easily detached, removed, or added, to and from the system 10. The accumulator 30 is operably associated with a cold source or refrigerator/freezer 42. As shown, the cold source 42 is a liquid cryogen bath 43. Other collection configurations may be used.

A vacuum pump 60 is in communication with the system. Additional valves to control flow and direct exit gas can be used and are shown at various points (shown as 52, 55). A shut-off valve 47 can be positioned adjacent an "on-board"

exit gas tap 50. Certain of the valves downstream of the accumulator 30 are used for "on-board" thawing and delivery of the collected polarized gas. The system can also include a digital pressure transducer 54 and a flow control device 57 along with a shut-off valve 58. The shut-off valve 58 can control the flow of gas through the entire system or unit 10; and can be used to turn the gas flow on and off. As will be understood by those of skill in the art, other flow control mechanisms, devices (analog and electronic) may be used within the scope of the present invention.

In operation, a gas mixture is introduced into the system at the gas source 12. As shown in FIG. 1B, the source 12 is a pressurized gas tank which holds a pre-mixed gas mixture. The gas mixture includes a lean noble gas (the gas to be hyperpolarized) and buffer gas mixture. Preferably, for producing hyperpolarized $^{129}$Xe, the pre-mixed gas mixture is about 90% He, about 5% or less $^{129}$Xe (typically about 1% Xe), and about 10% $N_2$. The gas mixture can be passed through the purifier 16 and introduced into the polarizer cell 22. The valves 20, 28 are on/off valves operably associated with the polarizer cell 22. The gas regulator 14 steps down the pressure from the gas tank source 12 (typically operating at 2000 psi or 136 atm) to about 1-10 atm for the system, e.g., about 1 atm, about 2 atm, about 3 atm, about 4 atm, about 5 atm, or between about 6-10 atm for the system. For systems with spectrally narrowed lasers, lower cell operating pressures of between about 1-3 atm may be particularly desirable. Thus, during accumulation, the entire manifold (conduit, polarized cell, accumulator, etc.) can be pressurized to the cell pressure (about 3-10 atm). The flow in the unit 10 can be activated by opening valve 58 and is controlled by adjusting the flow control means 57. The typical residence time of the gas in the cell 22 is about 10-30 seconds; i.e., it takes on the order of 10-30 seconds for the gas mixture to be hyperpolarized while moving through the cell 22. The gas mixture is typically introduced into the cell 22 at a pressure of between about 1-10 atm. Of course, with hardware capable of operating at increased pressures, operating pressures of above 10 atm, such as about 20-30 atm can pressure broaden the Rb and absorb up to 100% of the optical light. In contrast, for laser linewidths less than conventional linewidths, lower pressures can be employed. The polarizer cell 22 can be a high pressure optical pumping cell housed in a heated chamber with apertures configured to allow entry of the laser emitted light.

In some embodiments, the polarizer 10 employs an optical pumping cell 22 at a pressure of about 3 atm. It is contemplated that a spectrally narrowed laser, that has been detuned by about 0.25-0.50 nm from the alkali D1 resonance at that pressure. As will be understood by one of skill in the art, a small pressure shift in resonance occurs from vacuum to the 3 atm pressure which can depend on the buffer gas composition. For example, in vacuum, Rb D1 resonance is at 794.8 nm, whereas at 3 atm with the same buffer gas mixture, it is shifted to a slightly lower wavelength of 794.96 nm.

The polarizer unit 10 can employ helium buffer gas to pressure broaden the Rb vapor absorption bandwidth. The selection of a buffer gas can be important because the buffer gas—while broadening the absorption bandwidth—can also undesirably impact the alkali metal-noble gas spin-exchange by potentially introducing an angular momentum loss of the alkali metal to the buffer gas rather than to the noble gas as desired.

Hyperpolarized gas, together with the buffer gas mixture, exits the polarizer cell 22 and travels along the manifold (e.g., conduit) which may be configured with the filter 225 (FIG. 10A), then enters the accumulator 30. The polarized gas and buffer gas are directed down a primary flow path and into a collection reservoir. In operation, the hyperpolarized gas is exposed to temperatures below its freezing point and collected as a frozen product. The remainder of the gas mixture remains gaseous and exits the primary flow path and the reservoir such that it is directed out of the accumulator 30. The hyperpolarized gas is collected (as well as stored, transported, and preferably thawed) in the presence of a magnetic field, generally on the order of at least 500 Gauss, and typically about 2 kiloGauss, although higher fields can be used. Lower fields can potentially undesirably increase the relaxation rate or decrease the relaxation time of the polarized gas. The magnetic field can be provided by permanent magnets 40 positioned about a magnetic yoke 41.

The hyperpolarizer 10 can also use the temperature change in the outlet line between the heated pumping cell 22 and the refrigerated cold trap or accumulator 30 to precipitate the alkali metal from the polarized gas stream in the conduit above the accumulator 30. This temperature change can be localized as a nanocluster filter 225 as discussed above or may extend over a long flow zone. As will be appreciated by one of skill in the art, the alkali metal can precipitate out of the gas stream at temperatures of about 40 degrees C. The unit can also include an alkali metal reflux condenser (not shown). The refluxing condenser employs a vertical refluxing outlet pipe which is kept at room temperature. The gas flow velocity through the refluxing pipe and the size of the refluxing outlet pipe is such that the alkali metal vapor condenses and drips back into the pumping cell by gravitational force. In any event, it is desirable to remove the alkali metal prior to delivering polarized gas to a patient.

Once a desired amount of hyperpolarized gas has been collected in the accumulator 30, the accumulator can be detached or isolated from the system. To do so, valve 28 can be closed, leaving the cell 22 pressurized. This allows the accumulator 30 and the downstream plumbing to begin to depressurize because the flow valve 58 is open. The unit 10 downstream of the valve 28 can be allowed to depressurize to about 1.5 atm before the flow valve 58 is closed. After closing the flow valve 58, valve 55 can be opened to evacuate the remaining gas in the manifold. Once the outlet plumbing is evacuated, valves 35 and 37 are closed. If the collected gas is to be distributed "on board," i.e., without removing the accumulator 30 from the unit 10, a receptacle such as a bag or other vessel can be attached to the outlet 50. The valve 47 can be opened to evacuate the attached bag (not shown). Once the bag is evacuated and the gas is ready to thaw, valve 52 can be optionally closed. This minimizes the contact of the polarized gas with the pressure transducer region 59 of the unit 10. This region typically includes materials that have a depolarizing effect on the polarized gas. Thus, long contact times with this region may promote relaxation of the polarized gas.

If the valve 52 is not closed, then valve 55 is preferably closed to prevent the evacuation of polarized thawed gases. The flow channels on the downstream side of the cell 22 can be formed from materials which minimize the decaying effect on the polarized state of the gas. Coatings can also be used such as those described in U.S. Pat. No. 5,612,103, the disclosure of which is hereby incorporated by reference as if recited in full herein. In the "on-board" thaw operation, valve 37 is opened to let the gas out. It then proceeds through valve 47 and out outlet 50.

In the "detached" or "transported accumulator" thaw mode, accumulator first and second isolation valves 35, 37 are closed after the depressurization and evacuation of the accumulator 30. Evacuating the accumulator 30 allows any residual gas in the accumulator to be removed. Leaving gas in the accumulator 30 with the frozen polarized gas may contribute to the heat load on the frozen gas, possibly raising the temperature of the frozen gas and potentially shortening the relaxation time. Thus, after depressurization and evacuation and closing the isolation valves 35, 37, the accumulator 30 can be disconnected from the unit 10 via release points 31, 32.

Examples of suitable isolation valves 20, 28, 35, 37 and/or for valves V for the pre-sat chamber 200 (FIG. 8F, 10B, 10C), include KIMBLE KONTES Valves 826450-004, 826460-0004 located in Vineland, N.J.

In some embodiments, the isolation valves 35, 37 are in communication with the primary flow channel and the buffer gas exit channel, respectively, and each can adjust the amount of flow therethrough as well as close the respective paths to isolate the accumulator from the system 10 and the environment. After the filled accumulator 30 is removed, another accumulator can be easily and relatively quickly attached to the release points 31, 32. Preferably, when attaching the new accumulator 30, the outlet manifold is evacuated using valve 55 (with valves 52, 35, 37 open). When a suitable vacuum is achieved (such as about 100 mm Torr) which typically occurs within about one minute or so, valve 55 is closed. Valve 28 is then re-opened which re-pressurizes the outlet manifold to the operating cell pressure. Valve 58 is then opened to resume flow in the unit 10. Preferably, once flow resumes, liquid nitrogen is applied to the accumulator 30 to continue collection of the hyperpolarized gas. Typically such a changeover takes on the order of less than about five minutes. Thus, a preferred hyperpolarizer unit 10 is configured to provide a continuous flow of hyperpolarized $^{129}$Xe gas for continuous production and accumulation of same.

As will be appreciated by one of skill in the art, embodiments of the invention may be embodied as a method, system, data processing system, or computer program product. Accordingly, the present invention may take the form of an entirely software embodiment or an embodiment combining software and hardware aspects, all generally referred to herein as a "circuit" or "module." Furthermore, the present invention may take the form of a computer program product on a non-transient computer usable storage medium having computer usable program code embodied in the medium. Any suitable computer readable medium may be utilized including hard disks, CD-ROMs, optical storage devices, a transmission media such as those supporting the Internet or an intranet, or magnetic or other electronic storage devices.

Computer program code for carrying out operations of the present invention may be written in an object oriented programming language such as Java, Smalltalk, PYTHON, C# or C++. However, the computer program code for carrying out operations of the present invention may also be written in conventional procedural programming languages, such as the "C" programming language or in a visually oriented programming environment, such as Visual Basic.

Certain or all aspects of the program code may execute entirely on one or more of a user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). Typically, some program code executes on at least one web (hub) server and some may execute on at least one web client and with communication between the server(s) and clients using the Internet. The polarizer and/or nanosuppression or detection control systems can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud." Cloud storage may include a model of networked computer data storage where data is stored on multiple virtual servers, rather than being hosted on one or more dedicated servers.

The invention is described in part below with reference to flowchart illustrations and/or block diagrams of methods, systems, computer program products and data and/or system architecture structures according to embodiments of the invention. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer readable memory or storage that can direct a computer or other programmable data processing apparatus to function in a particular manner, such that the instructions stored in the computer readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Figure 18:
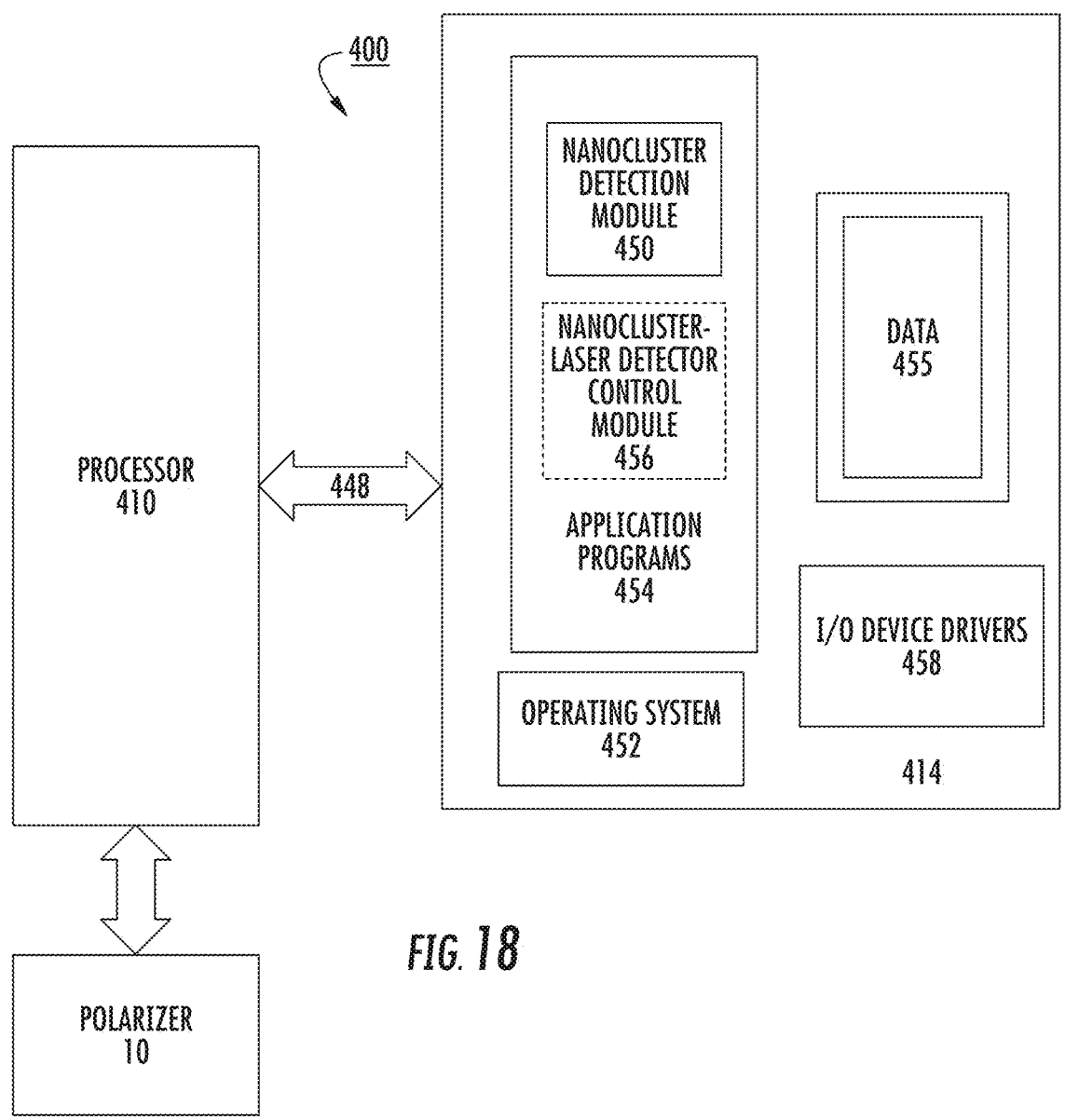
FIG. 18 is a schematic of a data processing system according to embodiments of the present invention.

FIG. 18 is a schematic illustration of a circuit or data processing system 400. The circuits and/or data processing systems 400 may be incorporated in a digital signal processor in any suitable device or devices. As shown in FIG. 18, the processor 410 communicates with and/or is integral with the polarizer 10 and with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 18 illustrates that the memory 414 may include several categories of software and data used in the data processing system: the operating system 452; the application programs 454; the input/output (I/O) device drivers 458; and data 455. The data 455 can include nanocluster signatures or laser attenuation levels associated with nanocluster detection from a laser-based (off resonance) detector for identifying the presence of such in the optical cell 22, for example.

As will be appreciated by those of skill in the art, the operating systems 452 may be any operating system suitable for use with a data processing system, such as OS/2, AIX, or zOS from International Business Machines Corporation, Armonk, N.Y., Windows CE, Windows NT, Windows95, Windows98, Windows2000, WindowsXP, Windows Visa, Windows7, Windows 8, Windows 8.1, Windows CE or other Windows versions from Microsoft Corporation, Redmond, Wash., Palm OS, Symbian OS, Cisco IOS, VxWorks, Unix or Linux, Mac OS from Apple Computer, LabView, or proprietary operating systems.

The I/O device drivers 458 typically include software routines accessed through the operating system 449 by the application programs 454 to communicate with devices such as I/O data port(s), data storage 455 and certain memory 414 components. The application programs 454 are illustrative of the programs that implement the various features of the data processing system and can include at least one application, which supports operations according to embodiments of the present invention. Finally, the data 455 represents the static and dynamic data used by the application programs 454, the operating system 452, the I/O device drivers 458, and other software programs that may reside in the memory 414.

While the present invention is illustrated, for example, with reference to the Nanocluster Detection Module 450 and optional nanocluster (NC) laser-detector control Module 456 being application programs in FIG. 18, as will be appreciated by those of skill in the art, other configurations may also be utilized while still benefiting from the teachings of the present invention. For example, the Module may also be incorporated into the operating system 452, the I/O device drivers 458 or other such logical division of the data processing system. Thus, the present invention should not be construed as limited to the configuration of FIG. 18 which is intended to encompass any configuration capable of carrying out the operations described herein. Further, Module 450 (and where used, Module 456) can communicate with or be incorporated totally or partially in other components, such as a separate or a single processor.

The I/O data port can be used to transfer information between the data processing system and another computer system or a network (e.g., the Internet) or to other devices controlled by the processor. These components may be conventional components such as those used in many conventional data processing systems, which may be configured in accordance with the present invention to operate as described herein.

Having now described the invention, the same will be illustrated with reference to certain examples, which are included herein for illustration purposes only, and which are not intended to be limiting of the invention.

EXAMPLES

Example 1: Hyperpolarized Gas Production with Alkali Metal Nanocluster Suppression in the Optical Pumping Cell The polarizer can have a low temperature, continuous flow, compact (500 cc or smaller) optical cell (Flow Through) with a silane and/or siloxane or equivalent surface coating.

The polarizer can include a high-temperature pre-saturation chamber configured to heat the pre-saturation chamber to a high temperature (e.g., about 140 degrees C. to about 250 degrees C.) and a second temperature zone, upstream of the pre-sat chamber, that heats the optical pumping cell to a lower temperature (between about 70 degrees C.-100 degrees C., typically at about 90 degrees C., about 95 degrees C., or about 100 degrees C.). "Bulk" Alkali metal is contained only in the pre-saturation chamber and alkali gas vapor enters the gas stream in the pre-sat chamber, then enters the optical pumping cell. The pre-saturation chamber resides outside the laser exposure region of the cell.

The optical cell can include a suitable material or coating to inhibit the formation and/or lifetime of nanoclusters.

The optical cell can include a siloxane or equivalent surface coating ("equivalent" refers to its ability to suppress bulk alkali pooling and/or nanocluster generation). The optical cell can comprise aluminosilicate glass, treated in a molted alkali metal (such as Potassium) salt bath, to inhibit the formation and lifetime of clusters.

Example 2: Hyperpolarized Gas Production with Filter(s) to Remove Alkali Metal Nanoclusters in the Hyperpolarized Gas Flow Path The hyperpolarizer can have a tortuous polarized gas flow path and/or nanocluster filter residing in the polarized gas flow path between the optical pumping cell and the cold finger. The tortuous path and/or nanocluster filter can reside outside the oven housing the pumping cell (e.g., in a cooler region). The walls of the filter and/or tortuous path can be at about a temperature corresponding to a freezing point of the alkali material forming the target nanoclusters, e.g., about 40 C, the freezing point of Rb.

The tortuous path can include indentations and changes in direction to promote turbulent flow so that nanoclusters and/or Rb (or other alkali material) vapor is directed to impact and stick to walls of the tortuous path and/or filter.

The gas flow path (post polarizer cell) can be cooled to promote surface adhesion of nanoclusters.

The flow path walls can be configured with a tangled surface such as comprising siloxanes to trap nanoclusters.

The flow path can be configured with a replaceable section and/or may be periodically cleaned to remove accumulated nanoclusters.

Example 3: Movement

During optical pumping, rotating the pumping cell to prevent or inhibit pooling of alkali metal.

During optical pumping, vibrating an internal coating, layer or surface of the cell and/or vibrating the entire optical pumping cell to prevent or inhibit pooling of alkali metal.

Example 4: Temperature Gradient in Cell with Pre-Sat Chamber

Low Temp, Continuous Flow, Compact (500CC or Smaller) Optical Cell (Flow Through), Siloxane or equivalent surface coating per Example 1 with the cell having a defined temperature gradient warm to less warm along the cell length so that the cell has a temperature gradient of at least 10 degrees C. along its length.

Example 5: Monitoring for Presence of Nanoclusters in Optical Cell

The hyperpolarizer can include a monitoring circuit that electronically monitors for the presence of nanoclusters in the optical cell (and/or polarized gas exit flow path).

Example 6: Hyperpolarized Gas Production Electrostatic or Electric Charge to Remove Alkali Metal Nanoclusters in the Hyperpolarized Gas Flow Path Methods of suppressing alkali clusters using electrostatic or electric potentials or charges to attract alkali clusters and remove them from the polarized gas stream or to retain them against a surface of the pumping cell.

Example 7: Quantifying Nanocluster Number Density

Potential signatures of nanocluster formation include the presence of specific fluorescence, or the non-resonant absorption of incident photons, both of which characteristics can potentially be utilized to quantify nanocluster number density, either by measuring the intensity of fluorescence photon flux, or through quantifying the absorption of a low-power (0.5-50 mW) probe beam at a specific, non-resonant wavelength, such as within the range of 200-750 nm, including about 250 nm, about 300 nm, about 350 nm, about 400 nm, about 450 nm, about 500 nm, about 550 nm, about 600 nm, about 650 nm or about 700 nm. The probe beam will be attenuated according to a Beer's law as $I=I0 \exp(-\sigma[A_n]z)$, where I is its intensity, $\sigma$ is the cluster scattering cross section at the probe wavelength, $[A_n]$ is the number density of alkali clusters and z is the propagation distance through the optical cell.

The cluster density (e.g., suppressed $<10^9/cm3$). One way to measure this cluster density "on-board" a respective hyperpolarizer can be by probe beam attenuation. The attenuation would follow Beers law, and go as $\exp(-sigma*[Rbn]*z)$, where sigma is the scattering cross section, z is the distance through the cell, and [Rbn] is the cluster number density. While z is known, sigma and [Rbn] can be determined based on the size or range of sizes of clusters that can be determined from TEM. Once that size is known, one can calculate their scattering cross sections at 450 nm (or other probe beam wavelength) from well-known Mie Scattering methods. Then, sigma and z are known and cluster density can be determined from probe beam attenuation.

Example 8: Experimental Study: Direct Detection of Alkali Metal Clusters in SEOP Cells Direct detection of alkali metal clusters was pursued using both scanning electron microscopy (SEM), and tunneling electron microscopy (TEM) as described below with respect to FIGS. 19-24.

The scanning electron microscopy study used samples obtained from a standard 300-cc SEOP (spin-exchange optical pumping) cell that had been used for >100 hours on a prototype Model 9800, Polarean commercial polarizer pumped using a 111 W 1.92 nm FWHM laser. The cell was removed from the polarizer and was cleaned out via controlled exposure to isopropyl alcohol and then rinsed with deionized water. The alcohol and water served to slowly and safely react and evaporate the rubidium that remained inside the cell. The cell was then carefully broken apart and pieces from the cell's rear window, front window, and side wall were selected for examination. Because SEM requires a conductive sample, the interior-wall side of each Pyrex piece was coated in roughly 4 nm of gold using a Denton Desk IV vacuum sputter coater.

The transmission electron microscopy (TEM) study employed samples captured from the inside of an SEOP cell. These samples were Formvar-coated transmission electron microscope (TEM) grids that had been inserted through the cell outlet tube. Insertion was done while maintaining a low flow of high-purity purge gas to ensure that no air contamination entered the cell. After grid insertion, the cell was installed in the polarizer and run under standard SEOP conditions with a gas flow rate of 1.67 standard liters per minute, while cell body temperature was maintained at 175° C. and optical pumping was done with 90 Watts of spectrally narrowed laser light. SEOP was conducted for ~1 hr, the typical time to collect a 1-liter batch of $^{129}$Xe. Next, the cell was cooled to room temperature, sealed, and removed from the polarizer and transported for TEM.

At the TEM facility, the cell was placed in a nitrogen glove bag that was outfitted to the sample exchange of the TEM. The bag was filled with N2 purge gas, which flowed continuously at ~0.2 SLM to minimize air contamination. Subsequently, the cell was broken open via a single hammer blow from outside (within/the bag). Subsequently, the TEM grids were extracted from the cell. One was selected for examination and inserted into the TEM for imaging.

Figure 19:
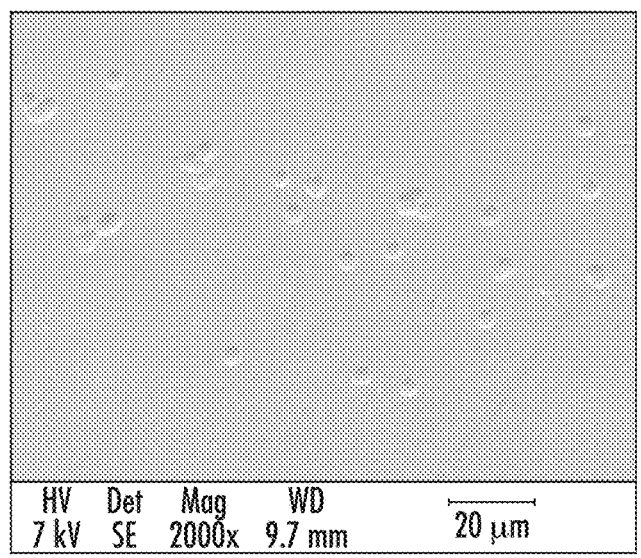
FIG. 19 is a scanning electron microscopy (SEM) image of the optical pumping cell face (2000× magnification) illustrating low density indentations.
Figure 20:
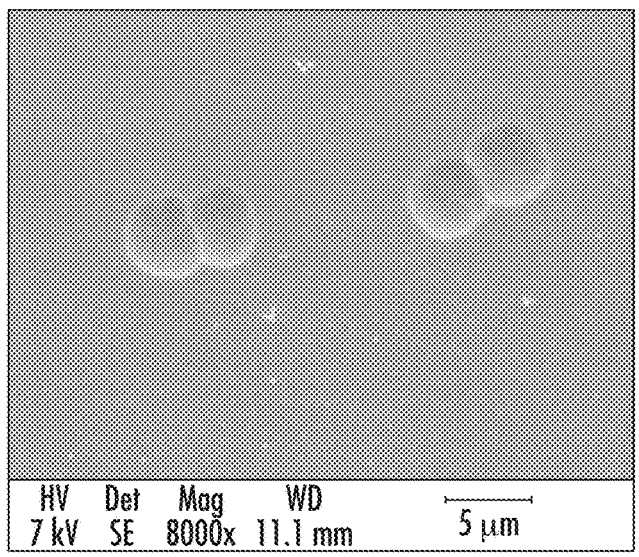
FIG. 20 is an SEM image of the optical pumping cell face (8000× magnification) also illustrating low density indentations.
Figure 21:
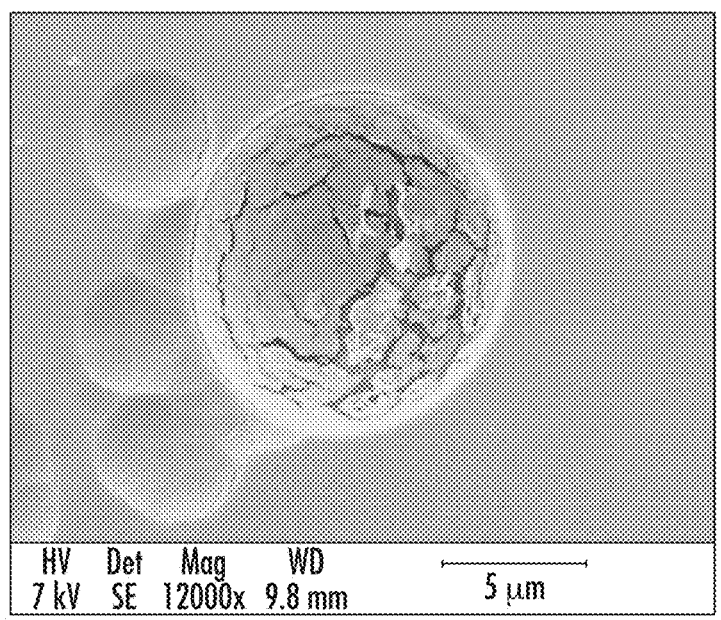
FIG. 21 is an SEM image of the optical pumping cell face (12000× magnification) of a large, reacted rubidium cluster in a crater presumably created by it.

Inspection of samples from the cell rear window and side wall yielded no significant feature other than some residual precipitate from the cell cleaning process. However, in striking contrast, images from the front window of the cell exhibited a remarkably different structure. As shown in FIGS. 19 and 20, circular indentations of approximately 1-5 microns in diameter were seen throughout the sample. FIG. 19 is an SEM image (magnification 2000x) of the optical pumping cell face with low density groupings of indentations. FIG. 20 is an SEM image of the cell facing showing another low density grouping of indentations (Magnification 8000x).

Given the presence of these indentations on only the cell face, and their near absence from the rear and side faces of the cell, it is believed that they are most likely created by impact from hot rubidium clusters. The prevalence of craters on the front window of the cell relative to the sides and rear window can potentially result from several factors. First, the gas mixture used in SEOP flows from the rear of the cell to the front, and may carry clusters with it. However, the bulk flow velocity of particles being carried in the gas mixture would be relatively modest (on the order of cm/min), and would not have the necessary energy to cause the cratering observed. It is noteworthy that Atutov describes soliton-like clouds of clusters moving towards the laser light entering the front of the cell (Atutov '12). Atutov describes these clusters as being exceedingly hot, which is likely what is required to indent the glass in the manner found.

In addition to detecting craters in the cell surface, perhaps the most remarkable finding was that of a number of large clusters that had remained on portions of the cell front surface, despite it having been rinsed out. An example of such a cluster is depicted in the "close-up" SEM image in FIG. 21 (magnification 12000×). The presence of these reacted clusters alone suggests that they are significantly more robust than expected. Particularly striking is the extraordinary size of these clusters, which appear to be roughly ~10 microns in diameter. By contrast, the nanocluster modeling suggests that these clusters were likely to have a size on the order of nanometers. However, the clusters seen here have been exposed to both water and air prior to SEM, and may therefore have enlarged substantially compared to their native state in an SEOP cell. This factor can be somewhat constrained in such growth models by looking at the impact craters, which have a diameter of order 2 microns, with a radius of curvature that is likely in the range of 5-10 microns based on the apparent shallowness of the craters. Impact craters frequently exceed the size of the particles that create them by an order of magnitude or more. Thus, based on crater size, it seems that in the SEOP cell, these clusters were likely <500-1000 nm in size.

Figure 22:
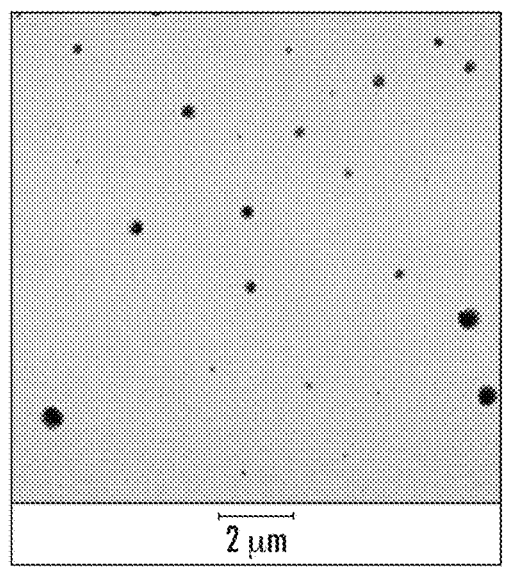
FIG. 22 is a tunneling electron microscopy (TEM) image of a grouping of clusters of average density (scale bar is 2 microns).
Figure 23:
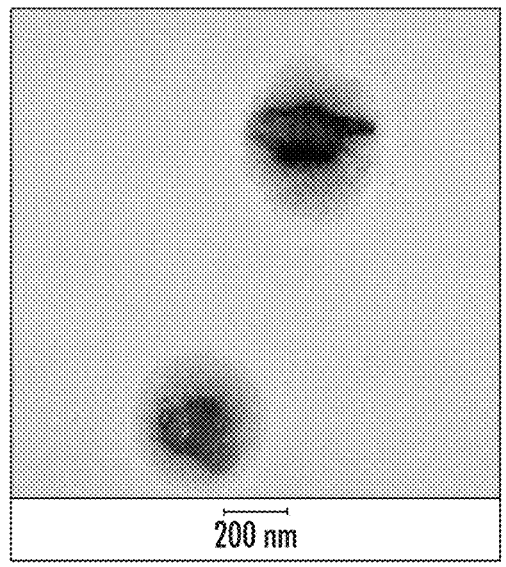
FIG. 23 is a TEM image of a pair of Rb clusters (scale bar is 200 nm, approximately the cluster size).
Figure 24:
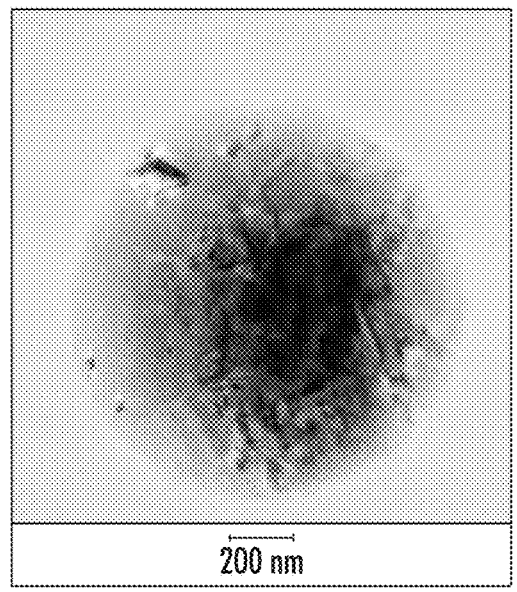
FIG. 24 is a TEM image of a Rb cluster that is estimated at about 600 nm in diameter (200 nm scale bar).

The TEM experiment provided a means to conduct direct imaging of the unreacted and unexposed rubidium from an SEOP cell. These images revealed extremely abundant and relatively uniformly distributed clusters. FIGS. 22-24 are TEM images of a representative sampling of this data.

Preliminary analysis of these images suggest that unreacted clusters range in size from 200 nm to 1 micron in diameter. As expected, this is smaller than what was seen in the air-exposed SEM images. It is worth noting, however, that in this case, the clusters were gathered over a period of only 1 hour of SEOP exposure, and thus might have continued to grow, had, the process been allowed to continue. A preliminary estimate of cluster density suggests a range of roughly 20 to 30 clusters per 100 square microns or $(25\pm5)\times 10^6$ clusters per square centimeter.

This initial study has demonstrated that large clusters of rubidium are detectable in SEOP cells. The SEM studies demonstrate that these clusters create micron-scale craters, predominantly at the front window of the cell. However, the study could not determine either the timescale of cluster formation, or their size, since samples were gathered from a heavily used SEOP cell and were exposed to air. In contrast, the TEM samples are particularly striking because they were represent only 1 hour of SEOP exposure. This study strongly suggests that clusters form in situ during SEOP on a relatively fast timescale. It cannot be completely ruled out that they were present on the surface of the cell already and the relatively turbulent conditions of SEOP simply "blew" them on to the grids. But in either case, it further confirms that clusters are present in the gas-phase of SEOP cells at all times, and do not simply form and then reside on the cell surface. In aggregate, the confirmation that alkali clusters do form in SEOP cells provides confirmation of the postulate that cluster formation is the likely explanation for why the standard model of SEOP has historically disagreed so dramatically with experimental result.

The below numbered paragraphs are provided for clear support that any combination of claims and/or features of claims can be presented in the future.

1. A flow-through optical spin exchange hyperpolarized gas production system for producing hyperpolarized gas comprising: a pre-saturation chamber comprising an Area Ratio (AR) of between 20 and 500, wherein the pre-saturation chamber comprises alkali metal therein; a heat source in communication with the pre-saturation chamber configured to heat the pre-saturation chamber to between 140 Celsius and 300 Celsius; a flow-through optical pumping cell in fluid communication with the pre-saturation chamber; and a heat source in communication with the optical pumping cell, wherein the heat source is configured to heat the optical pumping cell to a temperature that is less than the pre-saturation chamber.

2. The system of claim 1, wherein the pre-saturation chamber has an AR that is between 20 and 200, optionally about 100.

3. The system of claim 1 or 2 or the hyperpolarizer of claims 37 and 38, wherein a new and/or previously unused pre-saturation chamber comprises rubidium (Rb) in an amount between 0.5 and 5 grams.

4. The system of any of claims 1-3 or the hyperpolarizer of claims 37 and 38, wherein the pre-saturation chamber is replaceably and interchangeably detachable from the hyperpolarized gas production system for another pre-saturation chamber having a common size and shape and pre-filled with the alkali metal to thereby allow for a plurality of pre-saturation chambers to be used with the same optical pumping cell over production cycles.

5. The system of any of claims 1-4 or the hyperpolarizer of claims 37 and 38, further comprising a pressurized flow manifold that resides upstream of the optical pumping cell and maintains a gas flow path into the optical pumping cell at a defined pressure, wherein the pre-saturation chamber is a detachable pre-saturation chamber that is interchangeably, sealably attached to the pressurized flow manifold to allow a first used pre-saturation chamber to be replaced with a factory-sealed pre-saturation chamber comprising the alkali metal.

6. The system of any of claims 1-5 or the hyperpolarizer of claims 37 and 38, wherein the optical pumping cell comprises an electrical field between about 2 kV/cm to about 20 kV/cm that is configured to attract charged nanoclusters.

7. The system of any of claims 1-6 or the hyperpolarizer of claims 37 and 38, wherein the pre-saturation chamber comprises a silica wick.

8. The system of any of claims 1-7 or the hyperpolarizer of claims 37 and 38, further comprising a control circuit with a nanocluster detection and/or suppression module configured to control operation of the system so that generation of alkali nanoclusters is suppressed to below a value of $1\times10^9$ per $cm^3$ over at least a 45 minute operating period.

9. The system of any of claims 1-8 or the hyperpolarizer of claims 37 and 38, further comprising: a control circuit in communication with the optical pumping cell; a probe laser configured to project an off-resonance probe beam across the optical pumping cell; and a detector in communication with the probe laser and control circuit, positioned across from the probe laser on an opposing side of the optical pumping cell, wherein attenuation of a signal from the probe beam is associated with production of nanoclusters in the gas flow stream in the optical pumping cell.

10. The system of claim 9 or the hyperpolarizer of claims 37 and 38, wherein the probe laser has a wavelength that generates a blue laser beam, optionally at a wavelength of 450 nm.

11. The system of any of claims 1-10 or the hyperpolarizer of claims 37 and 38, further comprising an optical pumping laser in communication with the optical pumping cell, wherein the control circuit directs the optical pumping laser to turn OFF and/or a heat source associated with the optical pumping cell to decrease heat output or turn OFF when nanoclusters are detected.

12. The system of claim 9 or 10 or the hyperpolarizer of claims 37 and 38, wherein the probe laser resides along one long side of the optical pumping cell and directs the probe beam across the optical cell in a direction that is orthogonal to a direction of a spin-exchange optical pumping laser beam.

13. The system of any of claims 1-12 or the hyperpolarizer of claims 37 and 38, wherein the optical pumping cell comprises regional heat sources for defining an optical window on each side of the optical pumping cell for a probe laser to project across without attenuation due to alkali metal deposited onto an inner surface of the cell under the optical window.

14. The system of any of claims 1-13 or the hyperpolarizer of claims 37 and 38, further comprising an optical pumping laser having a wattage rating of between 200 W to 500 W.

15. An optical spin exchange hyperpolarized gas production system for producing hyperpolarized gas comprising any of the features of any of claims 1-14 or 37 and 38 and/or: a pre-saturation chamber comprising alkali metal; a heat source in communication with the pre-saturation chamber configured to heat the pre-saturation chamber to between 140 Celsius and 300 Celsius; an optical pumping cell in fluid communication with the pre-saturation chamber; and a nanocluster detection system in communication with the optical pumping cell.

16. The system of claim 15, further comprising a control circuit that includes and/or is in communication with the nanocluster suppression module that includes and/or is in communication with the nanocluster detection system.

17. The system of claim 15 or 16 or the hyperpolarizer of claims 37 and 38 and/any of claims 1-14, wherein the nanocluster detection system comprises one or more of: (i) a fluorescence spectroscopy detector, (ii) an IR (infrared) camera to observe plumes, and/or (iii) a probe laser and associated detector.

18. A method of producing hyperpolarized $^{129}$Xe, comprising: electronically detecting and/or monitoring for a presence of alkali nanoclusters within a flow optical cell.

19. A method for producing hyperpolarized $^{129}$Xe using any features or combinations of features in claims 1-14, claims 15-17 or claims 37 and 38, comprising: generating hyperpolarized $^{129}$Xe gas using spin-exchange optical pumping with a continuous flow through an optical pumping cell over a defined production period of at least 30 minutes; and suppressing generation of alkali nanoclusters below $1 \times 10^9$ per cm$^3$.

20. The method of claim 19, where the alkali nanocluster suppression is carried out to suppress at least one of Rb, Cs, Na, and K nanoclusters, and/or any combination thereof.

21. The method of claim 19, further comprising pre-saturating a noble gas mixture with vaporized alkali metal in a pre-saturation chamber having an Area Ratio (AR) of between 20 and about 500, optionally between 20 and 200 (such as about 100), residing outside a laser exposure region of an optical pumping laser associated with the optical pumping cell, then flowing the noble gas mixture with the vaporized alkali metal into the optical pumping cell for the generating step.

22. The method of claim 19 or any of the system claims 1-17, wherein the pre-saturation chamber comprises a silica wick.

23. The method of claim 21 or the system claims 1-17, further comprising interchanbeably sealably attaching a new (previously unused) pre-saturation chamber with alkali metal in an amount between 0.5 grams and 5 grams, to a manifold upstream of the optical pumping cell to replace a used pre-saturation chamber having reduced amount of alkali metal therein relative to the new pre-saturation chamber.

24. The method of claim 19, further comprising during the generating step, electronically monitoring for nanocluster generation in the optical pumping cell.

25. The method of claim 19, further comprising filtering nanoclusters from the generated hyperpolarized gas.

26. A pre-saturation device for a flow-through spin-exchange hyperpolarizer, comprising: a pre-saturation member having an internal pre-saturation chamber, wherein the per-saturation member is sealably attachable to a manifold of a spin-exchange hyperpolarizer upstream of an optical pumping cell, wherein the pre-saturation member has opposing first and second ends and alkali metal held in the pre-saturation chamber, prior to first use and/or prior to attachment to the manifold, in an amount between 0.5 grams and 5 grams.

27. The device of claim 26, wherein the alkali metal comprises at least one of Rb, Cs, Na, and K and/or any combination thereof with a cumulative amount, for a new and unused pre-saturation member, being between 1-3 grams.

28. The device of claim 26 or 27, wherein the pre-saturation member is configured for attachment to a hyperpolarizer in a sealed state to inhibit the alkali metal from being exposed to air.

29. The device of any of claims 26-28, wherein the pre-saturation member has longitudinally spaced apart end portions comprising one or more of: (i) metal seals, (ii) valves, and/or (iii) threaded attachment segments for sealably and releasably attaching to a pressurized fluid flow manifold on the hyperpolarizer.

30. The device of any of claims 26-29, wherein the pre-saturation chamber has an Area Ratio of between 20 and 500.

31. The device of claim 30, wherein the AR is between 20 and 500, 20 and 200 or optionally about 100, and optionally wherein the pre-saturation chamber comprises a silica wick.

32. An optical pumping cell that can be used with any of the system claims 1-17, the hyperpolarizer claims 37 and 38 or the method claims 18-25 that has an internal coating comprising one or more of polydimethylsiloxanes, paraffins, or a coating selected to hold up to alkalis metals and provide ballistic impact reduction or control to suppress cluster formation, wherein the coating comprises one or more of: a siloxane, a fluorinated and/or deuterated siloxane, a silane, a fluorinated and/or deuterated silane, a polydialkylsiloxane, a fluorinated and/or deuterated polydialkylsiloxane, a polyalkylarylsiloxane, a fluorinated and/or deuterated polyalkylarylsiloxane, a polydiarylsiloxane, a fluorinated and/or deuterated polydiarylsiloxane, a polyheteroorganosiloxane, a fluorinated and/or deuterated polyheteroorganosiloxane, a paraffin, a deuterated and/or fluorinated paraffin, a hydrocarbon wax, a deuterated and/or fluorinated hydrocarbon wax, and any combination thereof.

33. A method of suppressing alkali nanoclusters that can be used alone or with any of the system claims 1-17 or the method claims 18-25, comprising applying electrostatic potentials to attract alkali nanoclusters to an optical pumping cell to remove alkali nanoclusters from noble gas during optical spin-exchange used to produce hyperpolarized gas.

34. A method of increasing hyperpolarized gas yields comprising: detecting and/or monitoring for the presence of alkali nanoclusters within a flow optical pumping cell.

35. The method of claim 34, wherein the detecting is carried out using one or more of: (a) fluorescence spectroscopy, (b) imaging with an IR camera to observe plumes, or (c) a probe beam that is attenuated by the nanoclusters but not by atomic alkali metal in the optical pumping cell.

36. The method of claim 34 or 35, further comprising using a nanocluster filter in fluid communication with the optical pumping cell to filter nanoclusters from a polarized gas flow.

37. A hyperpolarizer comprising: a pressurized gas flow manifold in communication with an optical pumping cell; and a voltage source configured to apply an electric field across the optical pumping cell to thereby attract alkali nanoclusters.

38. The hyperpolarizer of claim 37, wherein the electric field is in a range of about 2 kV/cm to about 20 kV/cm.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

CITED REFERENCES

Incorporated by Reference as if Recited in Full Herein

Atutov S, Plekhanov A, Shalagin A, et al Explosive evaporation of Rb or K fractal clusters by low power CW radiation in the presence of excited atoms. The European Physical Journal D 2012; 66(5):1-6.

Bhaskar N D, Happer W, McClelland T. Efficiency of Spin Exchange between Rubidium Spins and ^{129}Xe Nuclei in a Gas. Physical Review Letters 1982; 49(1):25-28.

Couture A H, Clegg T B, Driehuys B. Pressure Shifts and Broadening of the Cs D1 and D2 Lines by He, N2 and Xe at Densities used for Optical Pumping and Spin Exchange Polarization. Journal of Applied Physics 2008; 104(14): 094912.

Driehuys B, Cates G, Miron E, et al High volume production of laser polarized 129 Xe. Appl Phys Lett 1996; 69(12): 1668-1670.

Driehuys B, Pollaro J, Cofer GP. In vivo MRI using real-time production of hyperpolarized 129Xe. Magn Reson Med 2008; 60(1):14-20.

Goodson B M. Nuclear Magnetic Resonance of Laser-Polarized Noble Gases in Molecules, Materials, and Organisms. J Magn Reson 2002; 155(2):157-216.

Hersman F W, Ruset I C, Ketel S, et al Large production system for hyperpolarized Xe-129 for human lung imaging studies. Acad Radiol 2008; 15(6):683-692.

Imai H, Fukutomi J, Kimura A, Fujiwara H. Effect of reduced pressure on the polarization of 129Xe in the production of hyperpolarized 129Xe gas: Development of a simple continuous flow mode hyperpolarizing system working at pressures as low as 0.15 atm. Concepts in Magnetic Resonance Part B: Magnetic Resonance Engineering 2008; 33(3):192-200.

Korchak S E, Kilian W, Mitschang L. Configuration and Performance of a Mobile 129Xe Polarizer. Applied magnetic resonance 2013; 44 (1-2):65-80.

Lowery T J, Rubin S M, Ruiz E J, et al Applications of laser-polarized 129xe to biomolecular assays. Magn Reson Imaging 2003; 21(10):1235-1239.

Mortuza M G, Anala S, Pavlovskaya G E, Dieken T J, Meersmann T. Spin-exchange optical pumping of high-density xenon-129. The Journal of chemical physics 2003; 118:1581.

Mugler J P, Altes T A. Hyperpolarized 129Xe MRI of the human lung. J Magn Reson Imaging 2013; 37(2):313-331.

Navon G, Song Y Q, Room T, et al Enhancement of solution NMR and MRI with laser-polarized xenon. Science 1996; 271(5257):1848-1851.

Nelson I A, Walker T G. Rb—Xe spin relaxation in dilute Xe mixtures. Phys Rev A 2001; 65(1):012712.

Nikolaou P, Whiting N, Eschmann N A, et al Generation of laser-polarized xenon using fiber-coupled laser-diode arrays narrowed with integrated volume holographic gratings. J Magn Reson 2009; 197(2):249-254.

Norquay G, Parnell S R, Xu X, Parra-Robles J, Wild J M. Optimized production of hyperpolarized 129 Xe at 2 bars for in vivo lung magnetic resonance imaging. Journal of Applied Physics 2013; 113(4):044908-044908-044909.

Romalis M, Ledbetter M. Transverse Spin Relaxation in Liquid^{129} Xe in the Presence of Large Dipolar Fields. Physical Review Letters 2001; 87(6):067601.

Rosen M, Chupp T, Coulter K, Welsh R, Swanson S. Polarized Xe optical pumping/spin exchange and delivery system for magnetic resonance spectroscopy and imaging studies. Rev Sci Instrum 1999; 70:1546.

Ruset I C, Ketel S, Hersman F W. Optical pumping system design for large production of hyperpolarized Xe-129. Physical Review Letters 2006; 96 (5).

Schrank G, Ma Z, Schoeck A, Saam B. Characterization of a low-pressure high-capacity^{129} Xe flow-through polarizer. Physical Review A 2009; 80(6):063424.

Schröder L, Lowery T J, Hilty C, Wemmer D E, Pines A. Molecular Imaging Using a Targeted Magnetic Resonance Hyperpolarized Biosensor. Science 2006; 314 (5798):446-449.

Shukla Y, Wheatly A, Kirby M, et al Hyperpolarized 129Xe Magnetic Resonance Imaging: Tolerability in Healthy Volunteers and Subjects with Pulmonary Disease. Acad Radiol 2012; 19(8):941-951.

Spence M M, Rubin S M, Dimitrov I E, et al Functionalized Xenon as a Biosensor. Proc Natl Acad Sci USA 2001; 98(19):10654-10657.

Springuel-Huet M-A, Bonardet J-L, Gédéon A, Fraissard J. 129Xe NMR overview of xenon physisorbed in porous solids. Magnetic Resonance in Chemistry 1999; 37 (13): S1-S13.

Wagshul M E, Chupp T E. Optical pumping of high-density Rb with a broadband dye laser and GaAlAs diode laser arrays: Application to ˆ{3}He polarization. Physical Review A 1989; 40(8):4447-4454.

Walker T G, Happer W. Spin-exchange optical pumping of noble-gas nuclei. Reviews of Modern Physics 1997; 69(2):629-642.

Walter D, Griffith W, Happer W. Energy transport in high-density spin-exchange optical pumping cells. Physical Review Letters 2001; 86(15):3264-3267.

Wolber J, Cherubini A, Leach M O, Bifone A. Hyperpolarized 129Xe NMR as a probe for blood oxygenation. Magn Reson Med 2000; 43(4):491-496.

Zook A L, Adhyaru B B, Bowers C R. High capacity production of >65% spin polarized xenon-129 for NMR spectroscopy and imaging. J Magn Reson 2002; 159(2):175-182.

That which is claimed is:

1. A flow-through optical spin exchange hyperpolarized gas production system for producing hyperpolarized gas comprising:
    a pre-saturation chamber comprising an Area Ratio (AR) of between 20 and 500, wherein the pre-saturation chamber comprises alkali metal therein;
    a heat source in communication with the pre-saturation chamber configured to heat the pre-saturation chamber to between 140 Celsius and 300 Celsius;
    a flow-through optical pumping cell in fluid communication with the pre-saturation chamber;
    a gas mixture comprising $^{129}$Xe gas in the optical pumping cell; and
    a heat source in communication with the optical pumping cell, wherein the heat source is configured to heat the optical pumping cell to a temperature that is less than the pre-saturation chamber,
    wherein the system hyperpolarizes the $^{129}$Xe gas in the optical pumping cell and provides at least one bolus amount of the hyperpolarized $^{129}$Xe gas for inhalation delivery to a patient.

2. The system of claim 1, further comprising an accumulator in fluid communication with the optical pumping and located downstream of the optical pumping cell, wherein the accumulator collects the at least one bolus amount of the hyperpolarized $^{129}$Xe gas.

3. The system of claim 2, further comprising a bag that is releasably coupled to the accumulator and that holds the at least one bolus amount of the hyperpolarized gas for inhalation delivery to the patient.

4. The system of claim 3, wherein the at least one bolus amount of hyperpolarized $^{129}$Xe gas in the bag has sufficient hyperpolarization level when dispensed to the patient in an MRI scanner to obtain MR spectroscopy data and/or MRI image data of at least one of pulmonary ventilation or gas exchange in one or more lungs of the patient.

5. The system of claim 1, wherein the AR of the pre-saturation chamber is between 20 and 200.

6. The system of claim 1, wherein a new and/or previously unused pre-saturation chamber comprises rubidium (Rb) in an amount between 0.5 and 5 grams.

7. The system of claim 1, wherein the pre-saturation chamber is a first pre-saturation chamber and has axially spaced apart first and second end portions that releasably and sealably engage a flow manifold that resides upstream of the optical pumping cell, wherein the first and second end portions are detachable from the flow manifold of the hyperpolarized gas production system, wherein the flow manifold releasably and sealably engages first and second end portions of a second pre-saturation chamber having a common size and shape as the first pre-saturation chamber, wherein the second pre-saturation chamber is filled with alkali metal to thereby allow for a plurality of pre-saturation chambers to be used with the same optical pumping cell over production cycles to provide at least one bolus amount of the hyperpolarized $^{129}$Xe gas.

8. The system of claim 1, further comprising a pressurized flow manifold that resides upstream of the optical pumping cell and maintains a gas flow path into the optical pumping cell at a defined pressure, wherein the pre-saturation chamber is a detachable pre-saturation chamber that, in operation, is interchangeably, sealably attached to the pressurized flow manifold with at least one quick connect and/or valve.

9. The system of claim 1, further comprising a voltage source that is configured to generate an electrical field between about 2 kV/cm to about 20 kV/cm in or about the optical pumping cell, wherein the electrical field is configured to attract charged nanoclusters.

10. The system of claim 1, further comprising:
    a control circuit in communication with the optical pumping cell;
    a probe laser configured to project an off-resonance probe beam across the optical pumping cell; and
    a detector in communication with the probe laser and control circuit, positioned across from the probe laser on an opposing side of the optical pumping cell, wherein the control circuit is configured to identify attenuation of a signal from the probe beam that is associated with production of nanoclusters in the gas flow stream in the optical pumping cell.

11. The system of claim 1, wherein the pre-saturation chamber is external to the optical pumping cell and is upstream of an inlet port of the optical pumping cell.

12. The system of claim 8, wherein the pre-saturation chamber comprises threads, a valve and/or a nozzle and is detachably, sealably attached to the flow manifold.

13. The system of claim 1, further comprising an accumulator in fluid communication with and downstream of the optical pumping cell, wherein, in operation, the hyperpolarized $^{129}$Xe gas is exposed to temperatures below its freezing point and collected as a frozen product at the accumulator.

14. The system of claim 13, further comprising a magnetic yoke of permanent magnets surrounding a portion of a cold finger of the accumulator.

15. The system of claim 1, wherein the system further comprises a probe laser positioned along one long side of the optical pumping cell, wherein the probe laser directs a probe beam across the optical cell in a direction that is orthogonal to a direction of a spin-exchange optical pumping laser beam.

16. The system of claim 15, further comprising regional heat sources for defining an optical window on each side of the optical pumping cell for the probe laser to project across without attenuation due to alkali metal deposited onto an inner surface of the cell under the optical window.

17. A flow-through optical spin exchange hyperpolarized gas production system for producing hyperpolarized gas comprising:
    a pre-saturation chamber comprising an Area Ratio (AR) of between 20 and 500, wherein the pre-saturation chamber comprises alkali metal therein;

a heat source in communication with the pre-saturation chamber configured to heat the pre-saturation chamber to between 140 Celsius and 300 Celsius;

a flow-through optical pumping cell in fluid communication with the pre-saturation chamber;

a gas mixture comprising $^{129}$Xe gas in the optical pumping cell;

a heat source in communication with the optical pumping cell, wherein the heat source is configured to heat the optical pumping cell to a temperature that is less than the pre-saturation chamber;

a control circuit in communication with the optical pumping cell;

a probe laser configured to project an off-resonance probe beam across the optical pumping cell, wherein the probe laser has a wavelength that generates a blue laser beam; and a detector in communication with the probe laser and control circuit, positioned across from the probe laser on an opposing side of the optical pumping cell, wherein attenuation of a signal from the probe beam is associated with production of nanoclusters in the gas flow stream in the optical pumping cell, wherein the system hyperpolarizes the $^{129}$Xe gas in the optical pumping cell and provides at least one bolus amount of the hyperpolarized $^{129}$Xe gas for inhalation delivery to a patient.

18. The system of claim 17, wherein the probe laser has a wavelength of about 450 nm.

19. The system of claim 17, wherein the pre-saturation chamber is external to the optical pumping cell and is upstream of an inlet port of the optical pumping cell.

20. The system of claim 17, wherein the at least one bolus amount of hyperpolarized $^{129}$Xe gas has sufficient hyperpolarization level when dispensed to the patient in an MRI scanner to obtain MR spectroscopy data and/or MRI image data of at least one of pulmonary ventilation or gas exchange in one or more lungs of the patient.

21. The system of claim 17, further comprising an accumulator in fluid communication with the optical pumping and located downstream of the optical pumping cell, wherein the accumulator collects the at least one bolus amount of the hyperpolarized $^{129}$Xe gas.

22. The system of claim 21, further comprising a bag that is releasably coupled to the accumulator and that holds the at least one bolus amount of the hyperpolarized gas for inhalation delivery to the patient.

23. The system of claim 21, wherein, in operation, the hyperpolarized $^{129}$Xe gas is exposed to temperatures below its freezing point and collected as a frozen product at the accumulator, and wherein the system further comprises a magnetic yoke of permanent magnets surrounding a portion of a cold finger of the accumulator.

24. An optical spin exchange hyperpolarized gas production system for producing hyperpolarized gas comprising:

a pre-saturation chamber comprising alkali metal;

a heat source in communication with the pre-saturation chamber configured to heat the pre-saturation chamber to between 140 Celsius and 300 Celsius;

an optical pumping cell in fluid communication with the pre-saturation chamber;

a gas mixture comprising $^{129}$Xe gas in the optical pumping cell; and a nanocluster detection system in communication with the optical pumping cell, wherein the nanocluster detection system comprises one or more of: (i) a fluorescence spectroscopy detector, (ii) an IR (infrared) camera to observe plumes, and/or (iii) a probe laser and associated detector, wherein the system hyperpolarizes the $^{129}$Xe gas in the optical pumping cell and provides at least one bolus amount of the hyperpolarized $^{129}$Xe gas for inhalation delivery to a patient.

25. The system of claim 24, wherein the pre-saturation chamber is external to and upstream of an inlet port of the optical pumping cell.

26. The system of claim 24, wherein the pre-saturation chamber comprises threads, a valve and/or a nozzle and is detachably, sealably attached to the flow manifold.

27. The system of claim 24, wherein the at least one bolus amount of hyperpolarized $^{129}$Xe gas has sufficient hyperpolarization level when dispensed to the patient in an MRI scanner to obtain MR spectroscopy data and/or MRI image data of at least one of pulmonary ventilation or gas exchange in one or more lungs of the patient.

28. The system of claim 24, further comprising an accumulator in fluid communication with the optical pumping and located downstream of the optical pumping cell, wherein the accumulator collects the at least one bolus amount of the hyperpolarized $^{129}$Xe gas.

29. The system of claim 28, further comprising a bag that is releasably coupled to the accumulator and that holds the at least one bolus amount of the hyperpolarized gas for inhalation delivery to the patient.

30. The system of claim 28, wherein, in operation, the hyperpolarized $^{129}$Xe gas is exposed to temperatures below its freezing point and collected as a frozen product at the accumulator, and wherein the system further comprises a magnetic yoke of permanent magnets surrounding a portion of a cold finger of the accumulator.

* * * * *

UNITED STATES PATENT AND TRADEMARK OFFICE
CERTIFICATE OF CORRECTION

PATENT NO. : 10,583,205 B2
APPLICATION NO. : 16/653082
DATED : March 10, 2020
INVENTOR(S) : Freeman et al.

Page 1 of 1

It is certified that error appears in the above-identified patent and that said Letters Patent is hereby corrected as shown below:

In the Specification

Column 19, Lines 7-8: Please correct "$\approx 10^{-13}$" to read -- $\approx 3 \times 10^{-13}$ --

Column 20, Line 41: Please correct "SN" to read -- S/V --

Column 29, Lines 30-34: Please correct "
$$\frac{\mu_{He} @ 150\ °C \quad V \quad R}{2.5 \times 10^{-5}\ kg\ m^{-1}\ s^{-1} \quad 0.02\ m\ s^{-1} \quad 3 \times 10^{-7}\ m}$$
"

to read --
$$\frac{\mu_{He} @ 150\ °C \quad V \quad R}{2.5 \times 10^{-5}\ kg\ m^{-1}\ s^{-1} \quad 0.02\ m\ s^{-1} \quad 3 \times 10^{-7}\ m}$$
--

Column 41, Line 52: Please correct "a is the cluster" to read -- σ is the cluster --

Signed and Sealed this
Twenty-eighth Day of July, 2020

Andrei Iancu
*Director of the United States Patent and Trademark Office*